(12) United States Patent
Schafer et al.

(10) Patent No.: US 11,555,107 B2
(45) Date of Patent: Jan. 17, 2023

(54) AMINE FUNCTIONALIZED POLYMERS AND METHODS OF PREPARATION

(71) Applicant: The University of British Columbia, Vancouver (CA)

(72) Inventors: Laurel L. Schafer, Vancouver (CA);
Savvas G. Hatzikiriakos, Surrey (CA);
Mitchell R. Perry, Vancouver (CA);
Damon J. Gilmour, Vancouver (CA);
Tanja Tomkovic, Vancouver (CA)

( * ) Notice: Subject to any disclaimer, the term of this patent is extended or adjusted under 35 U.S.C. 154(b) by 0 days.

(21) Appl. No.: 17/056,529

(22) PCT Filed: May 23, 2019

(86) PCT No.: PCT/CA2019/050704
§ 371 (c)(1),
(2) Date: Nov. 18, 2020

(87) PCT Pub. No.: WO2019/222852
PCT Pub. Date: Nov. 28, 2019

(65) Prior Publication Data
US 2021/0214542 A1    Jul. 15, 2021

Related U.S. Application Data

(60) Provisional application No. 62/675,465, filed on May 23, 2018.

(51) Int. Cl.
*C08F 8/32*      (2006.01)
*C08L 23/36*     (2006.01)
(Continued)

(52) U.S. Cl.
CPC ........... *C08L 23/36* (2013.01); *B01J 31/1616* (2013.01); *C08F 8/32* (2013.01); *C08F 210/16* (2013.01);
(Continued)

(58) Field of Classification Search
CPC ........... C08L 23/36; C08L 23/26; C08F 8/32; C08F 2810/40; C08F 210/16; C08F 110/06;
(Continued)

(56) References Cited

U.S. PATENT DOCUMENTS 4,217,914 A * 8/1980 Jacquet .............. C08G 73/0253
424/47
10,738,008 B2   8/2020 Anthis et al.
(Continued)

FOREIGN PATENT DOCUMENTS

EP      0768321 A2 * 4/1997 ................ C08F 8/00
WO   2005063834 A1     7/2005
(Continued)

OTHER PUBLICATIONS

International Search Report and Written Opinion of the International Searching Authority for International Patent Application No. PCT/CA2019/050704, dated Jul. 24, 2019, 9 pages.
(Continued)

*Primary Examiner* — Robert C Boyle
(74) *Attorney, Agent, or Firm* — Todd Lorenz; Todd A. Ostomel

(57) ABSTRACT

This application pertains to amine-functionalized polymers by ring-opening metathesis (ROMP) of amine functionalized cycloalkenes.

20 Claims, 30 Drawing Sheets

(51) Int. Cl.
*B01J 31/16* (2006.01)
*C08F 210/16* (2006.01)

(52) U.S. Cl.
CPC ....... *B01J 2531/58* (2013.01); *C08F 2810/40* (2013.01)

(58) Field of Classification Search
CPC ................ B01J 31/2243; B01J 31/2404; B01J 2231/4211; B01J 2531/56; B01J 2531/57; B01J 2531/58; B01J 2531/824; B01J 2540/40; C07C 209/60; C07C 275/28; C07D 233/32; C09D 5/14; C09D 123/26; C09J 123/26

See application file for complete search history.

(56) References Cited

U.S. PATENT DOCUMENTS

| | | | |
|---|---|---|---|
| 2005/0137369 A1 | 6/2005 | Baugh et al. | |
| 2006/0102895 A1 | 5/2006 | Hendrix et al. | |
| 2016/0195814 A1* | 7/2016 | Enomoto | G03F 7/322 430/311 |
| 2020/0283459 A1 | 9/2020 | Schafer et al. | |

FOREIGN PATENT DOCUMENTS

| | | |
|---|---|---|
| WO | 2012040853 A1 | 4/2012 |
| WO | 2012089617 A1 | 7/2012 |
| WO | 2018213938 A1 | 11/2018 |
| WO | 2019222834 A1 | 11/2019 |

OTHER PUBLICATIONS

Ackermann Lutz (Jun. 8, 2010) "Metal-Catalyzed Direct Alkylations of (Hetero)arenes Via C—H Bond Cleavages with Unactivated Alkyl Halides", Chemical Communications, 46:4866-4877.
Alfred et al. (Oct. 2008) "Water-Soluble Romp Polymers from Amine-Functionalized Norbornenes", Journal of Polymer Science Part A Polymer Chemistry, 46(19):6672-6676.
Aresta et al. (Aug. 14, 2010) "The Solid State Structure and Reactivity of NbCI(5) X (N.N'-Dicyclohexylurea) In Solution: Evidence for Co-ordinated Urea Dehydration to the Relevant Carbodiimide", Dalton Transactions, 39(30):6985-6992.
Bornand et al. (Jun. 9, 2007) "Mechanistically Designed Dual-Site Catalysts for the Alternating ROMP of Norbornene and Cyclooctene", Organometallics, 26(14):3585-3596.
Brandt et al. (Aug. 22, 2017) "Ligand Effects and Kinetic Investigations of Sterically Accessible 2-Pyridonate Tantalum Complexes for Hydroaminoalkylation", ACS Catalysis, 7(9):6323-6330.
Chen et al. (Jun. 29, 2009) "Palladium(II)-Catalyzed C—H Activation/C C Cross-Coupling Reactions: Versatility and Practicality", Angewandte Chemie International Edition, 48(28):5094-5115.
Chisholm et al. (Jun. 1, 1981) "Chloro(dimethylamido) Compounds of Tantalum(V): Preparations, Properties, and Structures of [Ta(NMe2)3CI2]2, TaCI3(NMe2)2(HNMe2), Ta(NMe2)3CI2(HNMe2), and [TaCI2(NMe2)2(HNMe2)]2O", Inorganic Chemistry, 20(6):1859-1866.
Chong et al. (Jul. 20, 2014) "2-Pyridonate Tantalum Complexes for the Intermolecular Hydroaminoalkylation of Sterically Demanding Alkenes", Journal of the American Chemical Society, 136(31):10898-10901.
Chong et al. (2014) "Hydroaminoalkylation: Early-Transition-Metal-Catalyzed alpha-Alkylation of Amines", Synthesis—Stuttgart, 46:2884-2896.
Clarkson et al. (Apr. 26, 2017) "Bis(tert-butylimido)bis(N,O-chelate)tungsten(VI) Complexes: Probing Amidate and Pyridonate Hemilability", Inorganic Chemistry, 56(10):5553-5566.
Clerici et al. (1980) "Catalytic C-Alkylation of Secondary Amines with Alkenes", Synthesis, 305-306.

Colby et al. (Dec. 8, 2011) "Rhodium Catalyzed Chelation-Assisted C—H Bond Functionalization Reactions", Accounts of Chemical Research, 45(6):814-825.
Dipucchio et al. (Mar. 19, 2018) "Catalytic and Atom-Economic Csp3—Csp3 Bond Formation: Alkyl Tantalum Ureates for Hydroaminoalkylation", Angewandte Chemie International Edition England, 57(13):3469-3472.
Dorfler et al. (May 2014, 2014) "A Commercially Available Tantalum Catalyst for the Highly Regioselective Intermolecular Hydroaminoalkylation of Styrenes", European Journal of Organic Chemistry, (13): 2790-2797.
Drew et al. (1975) "Crystal and Molecular Structure of Two Seven-co-ordinate Distorted Pentagonal Bipyramidal Complexes of Tantalum(V)", Journal of the Chemical Society, Dalton Transactions, 2611-2617.
Edwards et al. (Oct. 18, 2017) "In Situ Generation of a Regio- and Diastereoselective Hydroaminoalkylation Catalyst Using Commercially Available Starting Materials", Organic Letters, 19(21):5720-5723.
Eisenberger et al. (May 30, 2010) "Catalytic Synthesis of Amines and N-containing Heterocycles: Amidate Complexes for Selective C—N And C—C Bond-Forming Reactions", Pure and Applied Chemistry, 82:1503-1515.
Eisenberger et al. (2009) "Tantalum-Amidate Complexes for the Hydroaminoalkylation of Secondary Amines: Enhanced Substrate Scope and Enantioselective Chiral Amine Synthesis", Angewandte Chemie International Edition, 48:8361-8365.
Franssen et al. (2013) "Synthesis of Functional 'Polyolefins': State of the Art and Remaining Challenges", Chemical Society Reviews, 42:5809-5832.
Garcia et al. (2013) "Easily Assembled, Modular N,O-chelating Ligands ForTA(V) Complexation: A Comparative Study of Ligand Effects in Hydroaminoalkylation with N-methylaniline and 4-Methoxy-N-Methylaniline", Tetrahedron, 69:5737-5743.
Garcia et al. (2013) "Phosphoramidate Tantalum Complexes for Room-Temperature C—H Functionalization: Hydroaminoalkylation Catalysis", Angewandte Chemie International Edition, 52:9144-9148.
Goldmann et al. (May 27, 2013) "Post-Functionalization of Polymers via Orthogonal Ligation Chemistry", Macromolecular Rapid Communications, 34(10):810-849.
Hamzaoui et al. (Feb. 24, 2016) "Solid-State NMR and DFT Studies on the Formation of Well-Defined Silica-Supported Tantallaaziridines: From Synthesis to Catalytic Application", Chemistry, 22(9):3000-3008.
Herzon et al. (May 3, 2007) "Direct, Catalytic Hydroaminoalkylation of Unactivated Olefins with N-Alkyl Arylamines", Journal of the American Chemical Society, 29(21):6690-6691.
Herzon et al. (Nov. 12, 2008) "Hydroaminoalkylation of Unactivated Olefins with Dialkylamines", Journal of the American Chemical Society, 130(45):14940-14941.
Hilf et al. (2009) "Functional End Groups for Polymers Prepared Using Ring-opening Metathesis Polymerization", Nature Chemistry, 1:537-546.
Ireland et al. (Jun. 30, 2015) "Decomposition of a Phosphine-Free Metathesis Catalyst by Amines and Other Bronsted Bases: Metallacyclobutane Deprotonation as a Major Deactivation Pathway", ACS Catalysis, 5(8):4690-4698.
Kobayashi et al. (Mar. 16, 2016) "Regioselective Ring-Opening Metathesis Polymerization of 3-Substituted Cyclooctenes with Ether Side Chains", Macromolecules, 49(7):2493-2501.
Lau Ying Y. (Dec. 2016) "Catalytic Synthesis of N-heterocycles and Alpha-Alkylated Amines by Hydroamination and Hydroaminoalkylation", The University of British Columbia, 319 pages.
Lauzon et al. (Aug. 9, 2017) "Amidate Complexes of Tantalum and Niobium for the Hydroaminoalkylation of Unactivated Alkenes", ACS Catalysis, 7(9):5921-5931.
Lauzon Jean M. (May 2013) "Development of Group 4 and 5 Complexes with N,O Chelating Supporting Ligands as Catalysts for the A-alkylation of Amines", The University of British Columbia, 316 pages.

(56) References Cited

OTHER PUBLICATIONS

Le et al. (Jun. 21, 2017) "Selective sp3 C—H Alkylation via Polarity-Match-Based Cross-Coupling", Nature, 547:79-83.
Lienkamp et al. (Nov. 2, 2009) "Antimicrobial Polymers Prepared by Ring-Opening Metathesis Polymerization: Manipulating Antimicrobial Properties by Organic Counterion and Charge Density Variation", Chemistry—A European Journal, 15(43):11715-11722.
Lienkamp et al. (Jul. 1, 2008) "Antimicrobial Polymers Prepared by ROMP with Unprecedented Selectivity: A Molecular Construction Kit Approach", Journal of the American Chemical Society, 130(30):9836-9843.
Lummiss et al. (Nov. 19, 2014) "Donor-Induced Decomposition of the Grubbs Catalysts: An Intercepted Intermediate", Organometallics, 33(23):6738-6741.
Lyons et al. (2010) "Palladium-Catalyzed Ligand-Directed C—H Functionalization Reactions", Chemical Reviews, 110(2):1147-1169.
Mango et al. (Jan. 1973) "Hydrogenation of Unsaturated Polymers With Diimide", Die Makromolekulare Chemie, 163(1):13-36.
Martinez et al. (2015) "Functionalized Regio-Regular Linear Polyethylenes from the ROMP of 3-Substituted Cyclooctenes", Applied Petrochemical Research, 5:19-25.
Mcclennan et al. (Oct. 13, 2016) "A General Decomposition Pathway for Phosphine-Stabilized Metathesis Catalysts: Lewis Donors Accelerate Methylidene Abstraction", Journal of the American Chemical Society, 138(44):14668-14677.
Moorhouse et al. (1974) "Bis[(trimethylsilyl)methyl]- and bis(neopentyl)-zinc, and tris[(trimethylsilyl)methyl] aluminium-diethyl ether (1/1); their use as alkylating agents in forming niobium and tantalum alkyls", Journal of the Chemical Society, Dalton Transactions, 2187-2190.
Nugent et al. (Jan. 1, 1983) "Catalytic C—H Activation in Early Transition-Metal Dialkylamides and Alkoxides", Organometallics, 2(1):161-162.
Oda et al. (2016) "Diene Hydroaminomethylation via Ruthenium-Catalyzed C—C Bond Forming Transfer Hydrogenation: Beyond Carbonylation", Chemical Science, 7:136-141.
Payne et al. (Apr. 19, 2013) "Tantalum Catalyzed Hydroaminoalkylation for the Synthesis of $\alpha$- and $\beta$-Substituted N-Heterocycles", Organic Letters, 15(9):2182-2185.
Pelletier et al. (Mar. 9, 2016) "Catalysis by Design: Well-Defined Single-Site Heterogeneous Catalysts", Accounts of Chemical Research, 49(4):664-677.
Perez et al. (Jun. 2016) "Ruthenium-Catalyzed Transfer Hydrogenation for C—C Bond Formation: Hydrohydroxyalkylation and Hydroaminoalkylation via Reactant Redox Pairs", Topics in Current Chemistry, 374(3): 34 pages.
Perry Mitchell R. (Sep. 2017) "Catalytic Synthesis of Amines : From Small Molecules to Nitrogen-Containing Polymers", The University of British Columbia, 373 pages.
Perry et al. (Jun. 13, 2016) "Catalytic Synthesis of Secondary Amine-Containing Polymers: Variable Hydrogen Bonding for Tunable Rheological Properties", Macromolecules, 49(12):4423-4430.
Pitet et al. (Jan. 8, 2013) "Sequential ROMP of Cyclooctenes as a Route To Linear Polyethylene Block Copolymers", Dalton Transactions, 42:9079-9088.
Reznichenko et al. (Jan. 12, 2011) "Group 5 Metal Binaphtholate Complexes for Catalytic Asymmetric Hydroaminoalkylation and Hydroamination/Cyclization", Organometallics, 30(5):921-924.
Reznichenko et al. (Jan. 19, 2012) "The Mechanism of Hydroaminoalkylation Catalyzed by Group 5 Metal Binaphtholate Complexes", Journal of the American Chemical Society, 134(6):3300-3311.
Roesky et al. (2009) "Catalytic Hydroaminoalkylation", Angewandte Chemie International Edition, 48:4892-4894.
Ryken et al. (Aug. 6, 2015) "N,O-Chelating Four-Membered Metallacyclic Titanium(IV) Complexes for Atom-Economic Catalytic Reactions", Accounts of Chemical Research, 48(9):2576-2586.
Ryken et al. (2016) "Tight Bite Angle N,O-Chelates. Amidates, Ureates and BeyondLigand Design in Metal Chemistry: Reactivity and Catalysis", First Edition. Edited by Mark Stradiotto 2016 John Wiley and Sons, 364-405.
Sarkar et al. (2000) "Insulin Mimetic Peroxo Complexes of Vanadium Containing Uracil or Cytosine as Ligand", Metal-Based Drugs, 7(3):157-164.
Sattler et al. (Aug. 14, 2011) "Structural Characterization of TaMe3CI2 and Ta(PMe3)2Me3CI2, a Pair of five and Seven-Coordinate d0 Tantalum Methyl Compounds", Dalton Translation, 40(30):7777-7782.
Schrock et al. (1978) "Multiple Metal-Carbon Bonds. 7. Preparation and characterization of Ta(.eta.5-C5H5)2(CH2)(CH3), a study of its decomposition, and some simple reactions", Journal of the American Chemical Society, 100(8):2389-2399.
Schrock et al. (May 1, 1978) "Multiple Metal-Carbon Bonds. 8. Preparation, Characterization, and Mechanism of Formation of the Tantalum and Niobium Neopentylidene Complexes, M(CH2CMe3)3(CHCMe3)", Journal of the American Chemical Society, 100(11):3359-3370.
Sutthasupa et al. (Oct. 13, 2010) "Recent Advances in Ring-Opening Metathesis Polymerization, and Application to Synthesis of Functional Materials", Polymer Synthesis and Reactions, 42:905-915.
Sutthasupa et al. (Feb. 12, 2009) "Romp of Norbornene Monomers Carrying Nonprotected Amino Groups with Ruthenium Catalyst", Macromolecules, 42(5):1519-1525.
Thullen et al. (2017) "A Mild Hydroaminoalkylation of Conjugated Dienes Using a Unified Cobalt and Photoredox Catalytic System", Journal of the American Chemical Society, 139(43):15504-15508.
Tran et al. (Aug. 21, 2017) "Practical Alkoxythiocarbonyl Auxiliaries for Iridium(I)-Catalyzed C—H Alkylation of Azacycles", Angewandte Chemie International Edition, 56(35):10530-10534.
Yamauchi et al. (May 11, 2017) "Hydroxoiridium-Catalyzed Hydroalkylation of Terminal Alkenes with Ureas by C(sp3)—H Bond Activation", Angewandte Chemie International Edition, 56(25):7200-7204.
Zhang et al. (Jan. 10, 2011) "Synthesis and Catalytic Activity of Group 5 Metal Amides with Chiral Biaryldiamine-Based Ligands", Dalton Transactions, 40:1547-1566.
Zhang et al. (Jul. 1, 2013) "TaMe3CI2-Catalyzed Intermolecular Hydroaminoalkylation: A Simple Complex for Enhanced Reactivity and Expanded Substrate Scope", Chemistry—A European Journal, 19(27):8751-8754.
Zi et al. (2010) "Highly Enantioselective Hydroaminoalkylation of Secondary Amines Catalyzed by Group 5 Metal Amides with Chiral Biarylamidate Ligands", Chemical Communications, 46:6296-6298.
U.S. Appl. No. 17/056,903, filed Nov. 19, 2020, Schafer et al.
Yang et al., "Ring-Opening Metathesis Polymerization as a Route to Controlled Copolymers of Ethylene and Polar Monomers: Synthesis of Ethylene-Vinyl Chloride-Like Copolymers", Journal of Polymer Science Part A: Polymer Chemistry, vol. 41:13, pp. 2107-2116 (2003).

* cited by examiner

Post-polymerization modification

ADMET followed by hydrogenation

Radical/catalytic copolymerization

ROMP followed by hydrogenation

AMINE FUNCTIONALIZED POLYMERS AND METHODS OF PREPARATION

RELATED APPLICATIONS

This application is a national phase entry of PCT/CA2019/050704 filed on May 23, 2019 which claims priority to U.S. patent application No. 62/675,465 filed on May 23, 2018, the contents of each of which are incorporated herein by reference in their entirety.

FIELD OF THE INVENTION

This disclosure relates to amine functionalized polymers. More particularly, this application relates to novel amine functionalized polymers that can be produced by ring-opening metathesis (ROMP) of amine functionalized cycloalkenes.

BACKGROUND

The catalytic functionalization of alkenes represents a sustainable and efficient method for the synthesis of molecules that are relevant for the chemical, pharmaceutical, and agrochemical industry. Such organic transformations are attractive as valuable building blocks, which are obtained economically from relatively inexpensive starting materials. Notably, the direct C—H functionalization of amines with alkenes, or hydroaminoalkylation, has gained notoriety due to the fact that polysubstituted amines can now be easily obtained in the absence of any protecting/directing groups or photoinitiators.[i]

It is known in the art that group 3 (Sc), 4 (Ti, Zr), and 5 (Nb, Ta) metal complexes may serve as powerful precatalysts in hydroaminoalkylation reactions. For example, N,O-chelated pyridonate tantalum based complexes were shown capable of reacting with sterically demanding internal alkenes and facilitate their reaction with secondary anilines. These reactions occurred in a 100% regioselective manner to give the branched products.

Despite the high demand of simple and economical methods for synthesis of amine building blocks in the chemical, pharmaceutical, and agrochemical industry, there are known issues with the catalytic systems presently in use. For instance, hydroaminoalkylation often requires high reaction temperatures (>110° C.) and quite long reaction times (>20 h), which many catalysts are not robust enough to tolerate. Moreover, substrate compatibility of these catalysts is known to be problematic, especially for internal alkenes such as cyclohexene and cyclooctene. The fact that excess alkene (at least 1.5 equivalents excess) is needed to achieve full substrate conversion remains a challenge as well.

In the case of the catalytic systems, where the active species have a Ta—NMe$_2$ moiety, the excess alkene is often justified by the deleterious side reactions between the released HNMe$_2$ and the alkene reagents, thereby affecting the stoichiometry of the reaction. The use of TaMe$_3$Cl$_2$ proved to be successful, as hydroaminoalkylations of amine and alkene substrates was achieved using this catalyst in stoichiometric amounts, but with the caveat that TaMe$_3$Cl$_2$ is light and temperature sensitive and therewith not suitable for large scale industrial processes. Using a similar approach, the addition of 1-octene to 4-methoxy-N-methyl-aniline at room temperature was achieved with a phosphoramidate supported Ta-Me complex as the catalyst. Although this catalyst demonstrated high reactivity, the phosphoramidate Ta-Me complex actually required excess alkene in order to fully convert the substrates. To improve the stability of early transition metal complexes, steric bulk in the form of e.g. bulky alkyl groups, such as for example CH$_2$SiMe$_3$ and CH$_2$CMe$_3$, may be complexed to the metal centre. Earlier, Wilkinson and Schrock have described the alkyl tantalum complexes Ta(CH$_2$SiMe$_3$)$_3$Cl$_2$ and Ta(CH$_2$CMe$_3$)$_3$Cl$_2$. However, their activity in hydroaminoalkylation reactions has not been reported in the art.

Martinez et al. (Applied Petrochemical Research, 5: 19-25) have adopted a strategy that utilizes ring-opening metathesis polymerization (ROMP) of amine functionalized, strained cylooctene monomers, followed by hydrogenation, to obtain linear polymers analogous to polyethylene with the key introduction of a covalently bound functional group to the backbone. However, the often observed incompatibility of the commercially available Grubbs Catalyst to monomers bearing unprotected amine functional groups limits the usefulness of this approach, as the Grubbs metathesis catalyst is deactivated during ROMP with amine containing cycloalkene monomers.

Thus, the efficient preparation of amine-containing polyolefinic materials remains a synthetic challenge.

SUMMARY OF THE INVENTION

This disclosure is based in part on the discovery that hydroaminoalkylation of a cycloalkene followed by ring-opening polymerization and optionally hydrogenation leads to functionalized polymers comprising at least one amine group. In various embodiments, said amine group introduces useful properties, such as self-healing, adhesive, and/or antimicrobial properties.

Aspects of the disclosure pertain to an amine-functionalized compound of Formula 2:

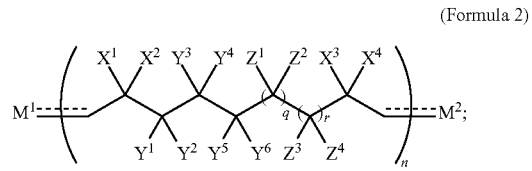
(Formula 2)

wherein --- indicates an optional double bond;
wherein each of M$^1$ and M$^2$ is independently —OH, a substituted or unsubstituted C$_{1-15}$ alkyl, a substituted or unsubstituted aromatic cycle, a substituted or unsubstituted heterocycle, or a functional end-group suitable for ring opening metathesis polymerization;
wherein each X$^1$, X$^2$, X$^3$, and X$^4$ is independently H or CH$_3$;
wherein each Y$^1$, Y$^2$, Y$^3$, Y$^4$, Y$^5$, Y$^6$, Z$^1$, Z$^2$, Z$^3$, and Z$^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R'', and wherein at least one of Y$^1$, Y$^2$, Y$^3$, Y$^4$, Y$^5$, Y$^6$, Z$^1$, Z$^2$, Z$^3$, and Z$^4$ is —CR$^1$R$^2$—NR$^3$R$^4$;

wherein each of R' and R" is independently H, a substituted or unsubstituted linear or cyclic alkyl or alkenyl, a substituted or unsubstituted aryl, a substituted or unsubstituted heterocycle, or an amine-compatible protection group;

wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group, or wherein $R^3$ and $R^4$ are linked to form a cyclic moiety, or wherein one of $R^3$ and $R^4$ is linked with one of $R^1$ and $R^2$ to form a cyclic moiety;

wherein r=0 or 1 and q=0 or 1, wherein r+q=0, 1, or 2; and wherein n is a natural number greater than 1.

In various embodiments, the monomers forming the amine-functionalized compound of Formula 2 are connected head to tail, head to head, tail to tail, or any combination thereof.

Aspects of the disclosure pertain to block copolymers comprising: an amine functionalized compound as described above; and a polymer formed by radical or anionic polymerization, for which the functional end-groups M1 and M2 of the amine functionalized compound serves as an initiation point.

A block copolymer prepared comprising: an amine functionalized compound as described above; and at least one additional polymer.

Aspects of the disclosure pertain to a polymer comprising an oligomer of Formula 3:

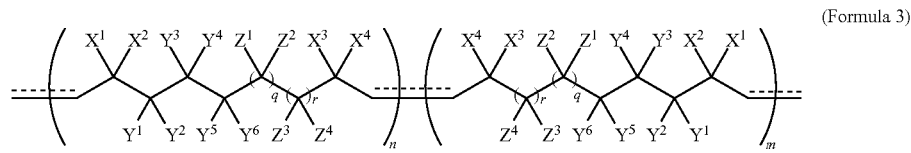

(Formula 3)

wherein --- indicates an optional double bond;

wherein each $X^1$, $X^2$, $X^3$, and $X^4$ is independently H or $CH_3$;

wherein each $Y^1$, $Y^2$, $Y^3$, $Y^4$, $Y^5$, $Y^6$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R", and wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;

wherein each of R' and R" is independently H, a substituted or unsubstituted linear or cyclic alkyl or alkenyl, a substituted or unsubstituted aryl, a substituted or unsubstituted heterocycle, or an amine-compatible protection group;

wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group, or wherein $R^3$ and $R^4$ are linked to form a cyclic moiety, or wherein one of $R^3$ and $R^4$ is linked with one of $R^1$ and $R^2$ to form a cyclic moiety;

wherein r=0 or 1 and q=0 or 1, wherein r+q=0, 1, or 2;

wherein n and m are natural numbers; and wherein the monomers are connected in a head to head fashion.

Aspects of the disclosure pertain to a polymer comprising an oligomer of Formula 4:

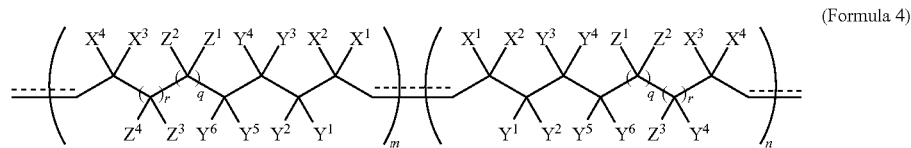

(Formula 4)

wherein --- indicates an optional double bond;
wherein each $X^1$, $X^2$, $X^3$, and $X^4$ is independently H or $CH_3$;
wherein each $Y^1$, $Y^2$, $Y^3$, $Y^4$, $Y^5$, $Y^6$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R", and wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;
wherein each of R' and R" is independently H, a substituted or unsubstituted linear or cyclic alkyl or alkenyl, a substituted or unsubstituted aryl, a substituted or unsubstituted heterocycle, or an amine-compatible protection group;
wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group, or wherein $R^3$ and $R^4$ are linked to form a cyclic moiety, or wherein one of $R^3$ and $R^4$ is linked with one of $R^1$ and $R^2$ to form a cyclic moiety;
wherein r=0 or 1 and q=0 or 1, wherein r+q=0, 1, or 2;
wherein n and m are natural numbers; and
wherein the monomers are connected in a tail to tail fashion.

Aspects of the disclosure pertain to a polymer comprising an oligomer of Formula 7:

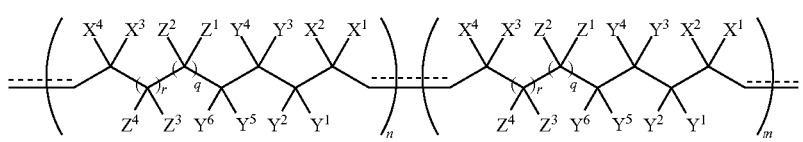

(Formula 7)

wherein --- indicates an optional double bond;
wherein each $X^1$, $X^2$, $X^3$, and $X^4$ is independently H or $CH_3$;
wherein each $Y^1$, $Y^2$, $Y^3$, $Y^4$, $Y^5$, $Y^6$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R", and wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;
wherein each of R' and R" is independently H, a substituted or unsubstituted linear or cyclic alkyl or alkenyl, a substituted or unsubstituted aryl, a substituted or unsubstituted heterocycle, or an amine-compatible protection group;
wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group, or wherein $R^3$ and $R^4$ are linked to form a cyclic moiety, or wherein one of $R^3$ and $R^4$ is linked with one of $R^1$ and $R^2$ to form a cyclic moiety;
wherein r=0 or 1 and q=0 or 1, wherein r+q=0, 1, or 2;
wherein n and m are natural numbers; and
wherein the monomers are connected in a head to tail fashion.

Aspects of the disclosure pertain to polymers of Formula X:

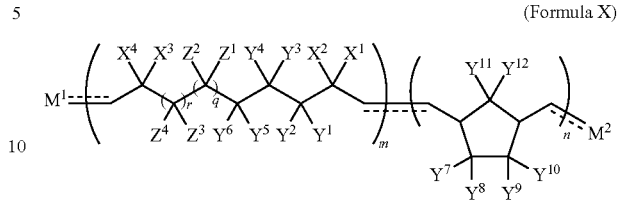

(Formula X)

wherein --- indicates an optional double bond;
wherein each of $M^1$ and $M^2$ is independently —OH, a substituted or unsubstituted $C_{1-15}$ alkyl, a substituted or unsubstituted aromatic cycle, a substituted or unsubstituted heterocycle, or a functional end-group suitable for ring opening metathesis polymerization;
wherein each $X^1$, $X^2$, $X^3$, and $X^4$ is independently H or $CH_3$;
wherein each $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R", and wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;
wherein each of R' and R" is independently H, a substituted or unsubstituted linear or cyclic alkyl or alkenyl, a substituted or unsubstituted aryl, a substituted or unsubstituted heterocycle, or an amine-compatible protection group;
wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group, or wherein $R^3$ and $R^4$ are linked to form a cyclic moiety, or wherein one of $R^3$ and $R^4$ is linked with one of $R^1$ and $R^2$ to form a cyclic moiety;
wherein r=0 or 1 and q=0 or 1, wherein r+q=0, 1, or 2;
wherein n and m are natural numbers; and
wherein the monomers are connected in a head to head fashion.

Aspects of the disclosure pertain to polymers comprising an oligomer of Formula XI:

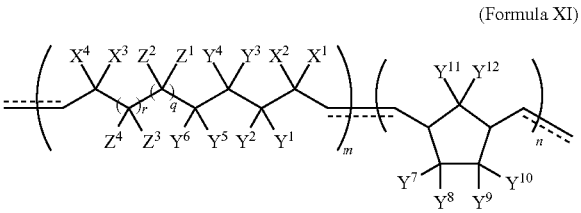

(Formula XI)

wherein --- indicates an optional double bond;
wherein each $X^1$, $X^2$, $X^3$, and $X^4$ is independently H or $CH_3$;
wherein each $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R", and wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;
wherein each of R' and R" is independently H, a substituted or unsubstituted linear or cyclic alkyl or alkenyl, a substituted or unsubstituted aryl, a substituted or unsubstituted heterocycle, or an amine-compatible protection group;
wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group, or wherein $R^3$ and $R^4$ are linked to form a cyclic moiety, or wherein one of $R^3$ and $R^4$ is linked with one of $R^1$ and $R^2$ to form a cyclic moiety;
wherein r=0 or 1 and q=0 or 1, wherein r+q=0, 1, or 2;
wherein n and m are natural numbers; and
wherein the monomers are connected in a head to head fashion.

Aspects of the disclosure pertain to co-polymers comprising a mixture of different amine-functionalized monomer units of Formula 6:

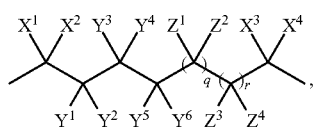

(Formula 6)

wherein --- indicates an optional double bond;
wherein each $X^1$, $X^2$, $X^3$, and $X^4$ is independently H or $CH_3$;
wherein each $Y^1$, $Y^2$, $Y^3$, $Y^4$, $Y^5$, $Y^6$, $Y^7$, $Y^8$, $Y^9$, $Y^{10}$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R", and wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;
wherein each of R' and R" is independently H, a substituted or unsubstituted linear or cyclic alkyl or alkenyl, a substituted or unsubstituted aryl, a substituted or unsubstituted heterocycle, or an amine-compatible protection group;
wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group, or wherein $R^3$ and $R^4$ are linked to form a cyclic moiety, or wherein one of $R^3$ and $R^4$ is linked with one of $R^1$ and $R^2$ to form a cyclic moiety;
wherein r=0 or 1 and q=0 or 1, wherein r+q=0, 1, or 2; and
wherein the monomer units are connected in a head to head fashion, head to tail fashion, tail to tail fashion, or any combination thereof.

Aspects of the disclosure pertain to a brush copolymer comprising a polymer as described above and polymeric bristles or brushes, wherein at least one of $X^1$, $X^2$, $X^3$, $X^4$, $Y^1$, $Y^2$, $Y^3$, $Y^4$, $Y^5$, $Y^6$, $Z^1$, $Z^2$, $Z^3$, $Z^4$, R', R", $R^1$, $R^2$, $R^3$, and $R^4$ serves as an initiation point for subsequent synthesis of polymeric bristles or brushes.

Aspects of the disclosure pertain to an amine functionalized polyalkene or polyalkane, wherein the polyalkene or polyalkane comprises:

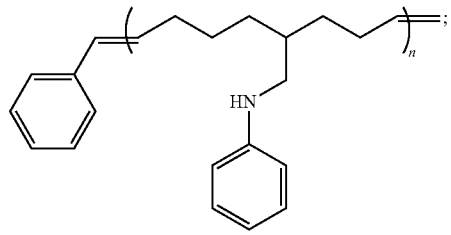

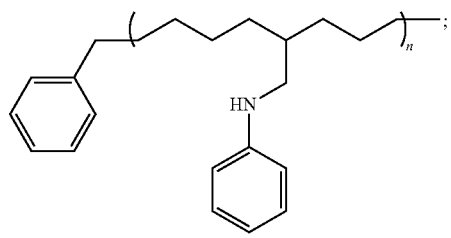

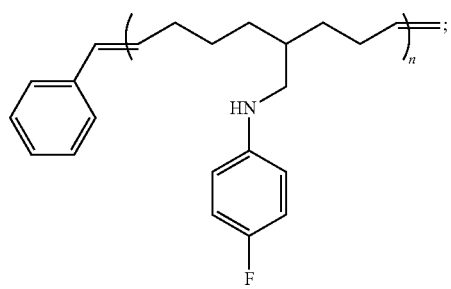

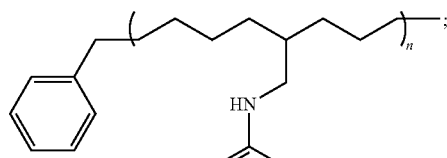

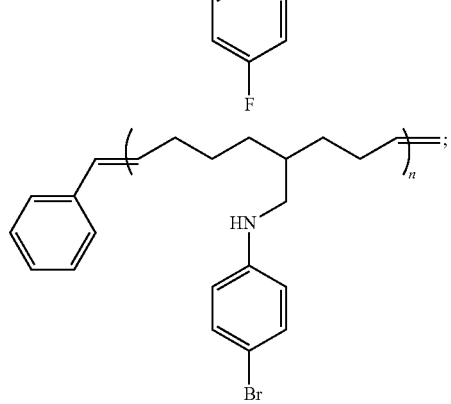

-continued

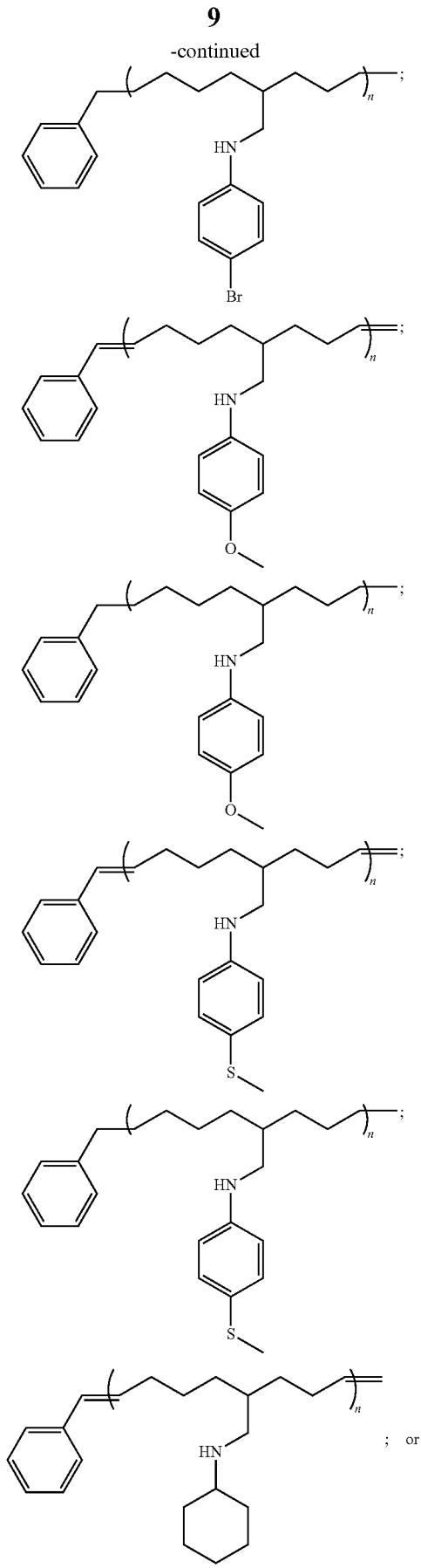

; or

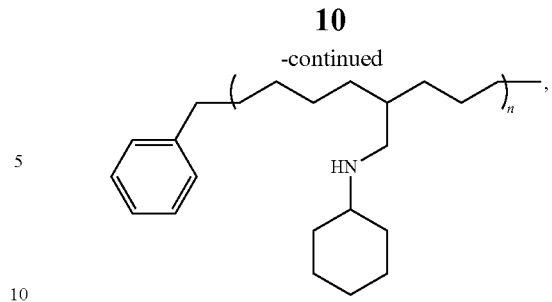

wherein n is a natural number greater than 1.

Aspects of the disclosure pertain to a polyalkane of Formula 5:

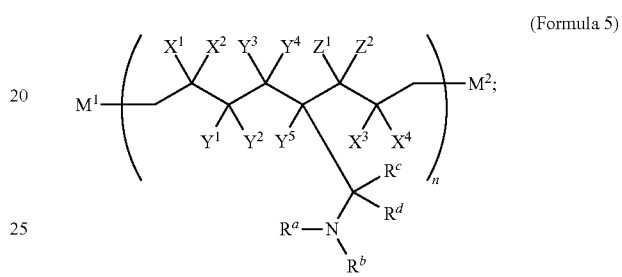

(Formula 5)

wherein each of $M^1$ and $M^2$ is independently —OH, a substituted or unsubstituted $C_{1-15}$ alkyl, a substituted or unsubstituted aromatic cycle, a substituted or unsubstituted heterocycle, or a functional end-group suitable for ring opening metathesis polymerization;

wherein each of $X^1$, $X^2$, $X^3$, and $X^4$ is independently H or $CH_3$;

wherein each of $Y^1$, $Y^2$, $Y^3$, $Y^4$, $Y^5$, $Z^1$, and $Z^2$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R";

wherein each of R' and R" is independently H, a substituted or unsubstituted linear or cyclic alkyl or alkenyl, a substituted or unsubstituted aryl, a substituted or unsubstituted heterocycle, or an amine-compatible protection group;

wherein each of $R^a$, $R^b$, $R^c$, and $R^d$ is independently H, a substituted or unsubstituted linear or cyclic alkyl or alkenyl, a substituted or unsubstituted aryl, a substituted or unsubstituted heterocycle, or an amine-compatible protection group, or wherein $R^b$ and $R^a$ are linked to form a cyclic moiety, or wherein one of $R^a$ and $R^b$ is linked with one of $R^c$ and $R^d$ to form a cyclic moiety;

wherein r=0 or 1 and q=0 or 1, wherein r+q=0, 1, or 2; and wherein n is a natural number greater than 1.

In various embodiments, the monomers are connected head to tail, head to head, tail to tail, or any combination thereof.

Polymers, polyalkanes, polyalkenes, and amine-functionalized compounds as described above may be useful as antimicrobial agents. Polymers, polyalkanes, polyalkenes, and amine-functionalized compounds as described above may be useful for reducing fouling. Fouling may include biofouling. Polymers as described above may be useful as adhesive agents. The adhesive agent may for adhering to a substrate. The substrate may be Teflon, glass, or metal.

Polymers, polyalkanes, polyalkenes, and amine-functionalized compounds as described above may be useful as a coating, a compatibilizer, a stabilizer, metal scavenger, a membrane a gasket, an anticoagulant, a drug delivery agent, or a scavenger agent. In various embodiments, the scavenger agent is for binding pollutants during environmental remediation in marine environments. In various embodiments, the pollutants include oil, plastic particles, or a combination thereof. In various embodiments the membrane is an electrolyte membrane or a filtering membrane for water purification.

Aspects of the disclosure pertain to substrates coated with polymers, polyalkanes, polyalkenes, and amine-functionalized compounds as described above.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Definitions

Figure 1:
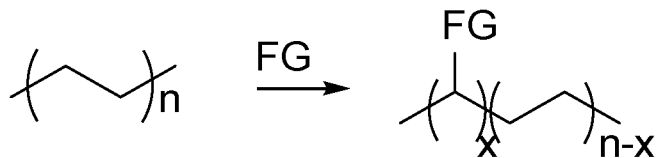
FIG. 1 is a schematic diagram of general strategy for synthesis of functionalized linear polyethylenes according to embodiments of the disclosure.
Figure 1:
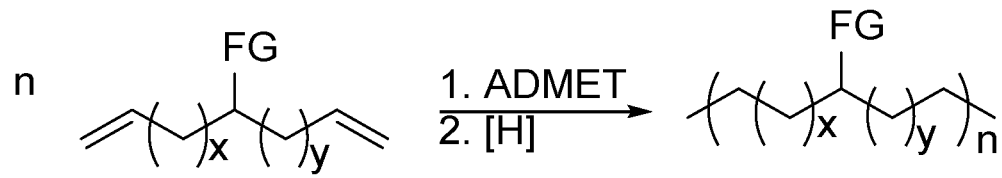
Figure 1:
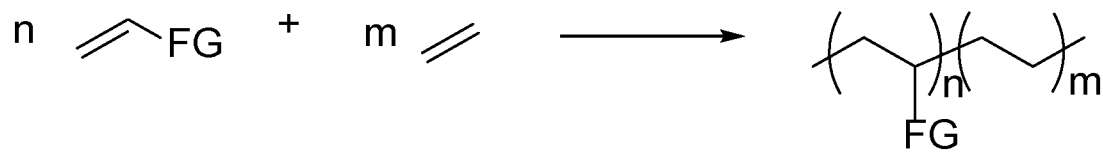
Figure 1:
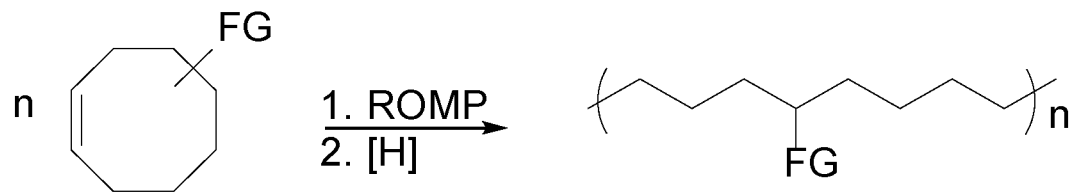

"Catalyst", as used herein, refers to a chemical compound that accelerates a chemical reaction without itself being affected. "Catalyst" may be used interchangeably with terms such as "pre-catalyst", "catalyst system", or "catalytic system". "Catalyst", as used herein, includes catalytic intermediates or species formed in situ.

"Group 5 metal" as used herein, refers to the d-electron comprising transition metals listed in the periodic table of the elements as group 5, including transition metals vanadium (V), niobium (Nb), tantalum (Ta), and dubnium (Db).

"Hydroaminoalkylation", as used herein, refers to a reaction between a secondary amine containing moiety and an olefin. A catalyst may often be used to promote such reaction.

"Secondary amine", as used herein, refers to an amine in which the amino group is directly bonded to two C-atoms of any hybridization. The two C-atoms in α-position to the N-atom may be sp$^3$ hybridized.

"Olefin" or "alkene", as used herein, refers to an unsaturated hydrocarbon containing one or more pairs of C-atoms linked by a double bond.

"TOF", as used herein, refers to "turnover frequency".

Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings. Titles, headings, or the like are provided to enhance the reader's comprehension of this document, and should not be read as limiting the scope of the present invention.

Amine-Functionalized Cycloalkenes

This disclosure pertains to amine-functionalized cycloalkenes of Formula 1:

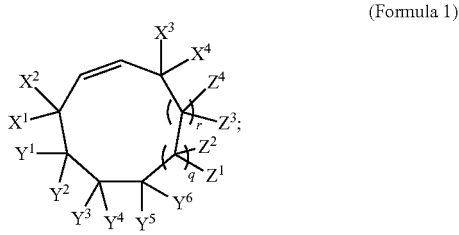

(Formula 1)

wherein:

$X^1$, $X^2$, $X^3$, and $X^4$ independently are H or $CH_3$;

$Y^1$, $Y^2$, $Y^3$, $Y^4$, $Y^5$, $Y^6$, $Z^1$, $Z^2$, $Z^3$, and $Z^4$ are each independently: H; a substituted or unsubstituted linear or cyclic alkyl or alkenyl; a substituted or unsubstituted aryl; a substituted or unsubstituted heterocycle; an amine-compatible protection group; —C(=O)R'; or —C(OR')R"; wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;

wherein each of R' and R" is independently H, a substituted or unsubstituted linear or cyclic alkyl or alkenyl, a substituted or unsubstituted aryl, a substituted or unsubstituted heterocycle, or an amine-compatible protection group; and wherein r=0 or 1 and q=0 or 1, wherein r+q=0, 1, or 2.

Each of $R^1$, $R^2$, $R^3$, and $R^4$ is independently H, a substituted or unsubstituted linear or cyclic alkyl or alkenyl, a substituted or unsubstituted aryl, a substituted or unsubstituted heterocycle, or an amine-compatible protection group. Alternatively, $R^3$ and $R^4$ are linked to form a cyclic moiety, wherein each of $R^1$ and $R^2$ is independently H, a substituted or unsubstituted linear or cyclic alkyl or alkenyl, a substituted or unsubstituted aryl, a substituted or unsubstituted heterocycle, or an amine-compatible protection group. Yet alternatively, one of $R^3$ and $R^4$ is linked with one of $R^1$ and $R^2$ to form a cyclic moiety in which case each of remaining groups of $R^1$, $R^2$, $R^3$, and $R^4$, as the case may be, is independently H, a substituted or unsubstituted linear or cyclic alkyl or alkenyl, a substituted or unsubstituted aryl, a substituted or unsubstituted heterocycle, or an amine-compatible protection group.

In various embodiments of the amine-functionalized cycloalkenes, each of $X^1$, $X^2$, $X^3$, and $X^4$ is H. In various embodiments of the amine-functionalized cycloalkenes, only one of $X^1$, $X^2$, $X^3$, and $X^4$ is $CH_3$. In various embodiments of the amine-functionalized cycloalkenes, each of $X^1$ and $X^3$ is H and each of $X^2$ and $X^4$ is $CH_3$. In various embodiments of the amine-functionalized cycloalkenes, at least one of $R^1$ and $R^2$ is H. In various embodiments of the amine-functionalized cycloalkenes, at least one of $R^3$ and $R^4$ is H.

In various embodiments of the amine-functionalized cycloalkenes, when $Y^1$, $Y^2$, $Y^3$, $Y^4$, $Y^5$, $Y^6$, $Z^1$, $Z^2$, $Z^3$, or $Z^4$ is —$CR^1R^2$—$NR^3R^4$, at least one ring-carbon atom adjacent to the ring-carbon atom substituted with —$CR^1R^2$—$NR^3R^4$ is substituted with two H atoms. In various embodiments, $Y^3$ is —$CR^1R^2$—$NR^3R^4$, and: each $Y^1$ and $Y^2$ is H; each of $Y^5$ and $Y^6$ is H; or each of each $Y^1$, $Y^2$, $Y^5$, and $Y^6$ is H.

In various embodiments of the amine-functionalized cycloalkenes, when $Y^1$, $Y^2$, $Y^3$, $Y^4$, $Y^5$, $Y^6$, $Z^1$, $Z^2$, $Z^3$, or $Z^4$ is —$CR^1R^2$—$NR^3R^4$, the ring-carbon atom substituted with —$CR^1R^2$—$NR^3R^4$ is further substituted with a hydrogen atom. In various embodiments, $Y^3$ is —$CR^1R^2$—$NR^3R^4$ and $Y^4$ is H.

This disclosure further pertains to polymers prepared by the ring opening metathesis polymerization (ROMP) of an amine-functionalized cycloalkene as described above.

This disclosure further pertains to polymers prepared by the ring opening metathesis polymerization (ROMP) of a mixture of different amine-functionalized cycloalkenes as described above. In various embodiments, the mixture comprises amine-functionalized cycloalkenes that are regioisomers. In various embodiments, the position of —$CR^1R^2$—$NR^3R^4$ groups on adjacent carbons is swapped between regioisomers.

In various embodiments, the monomer units are polymerized head-to-head, head-to-tail, tail-to-tail, or any combination thereof.

In various embodiments, the polymer is hydrogenated to remove double bonds in the polymer.

In various embodiments, the polymer has self-healing properties. In various embodiments, the polymer has adhesive properties. In various embodiments, the polymer has antimicrobial activity.

Polymers as described above may be useful as antimicrobial agents. Polymers as described above may be useful for reducing fouling. Fouling may include biofouling. Polymers as described above may be useful as adhesive agents. The adhesive agent may for adhering to a substrate. The substrate may be Teflon, glass, or metal.

Polymers as described above may be useful as a coating, a compatibilizer, a stabilizer, metal scavenger, a membrane a gasket, an anticoagulant, a drug delivery agent, or a scavenger agent. In various embodiments, the scavenger agent is for binding pollutants during environmental remediation in marine environments. In various embodiments, the pollutants include oil, plastic particles, or a combination thereof. In various embodiments the membrane is an electrolyte membrane or a filtering membrane for water purification.

Amine-Functionalized Compounds

This disclosure further pertains to amine-functionalized compounds of Formula 2:

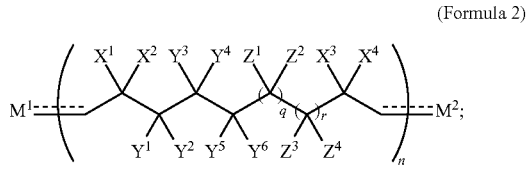

(Formula 2)

wherein --- indicates an optional double bond;
wherein each of $M^1$ and $M^2$ is independently —OH, a substituted or unsubstituted $C_{1-15}$ alkyl, a substituted or unsubstituted aromatic cycle, a substituted or unsubstituted heterocycle, or a functional end-group suitable for ring opening metathesis polymerization;
wherein each $X^1$, $X^2$, $X^3$, and $X^4$ is independently H or $CH_3$;
wherein each $Y^1$, $Y^2$, $Y^3$, $Y^4$, $Y^5$, $Y^6$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R'', and wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;
wherein each of R' and R'' is independently H, a substituted or unsubstituted linear or cyclic alkyl or alkenyl, a substituted or unsubstituted aryl, a substituted or unsubstituted heterocycle, or an amine-compatible protection group;
wherein r=0 or 1 and q=0 or 1, wherein r+q=0, 1, or 2; and wherein n is a natural number.

Each of $R^1$, $R^2$, $R^3$, and $R^4$ is independently H, a substituted or unsubstituted linear or cyclic alkyl or alkenyl, a substituted or unsubstituted aryl, a substituted or unsubstituted heterocycle, or an amine-compatible protection group. Alternatively, $R^3$ and $R^4$ are linked to form a cyclic moiety, wherein each of $R^1$ and $R^2$ is independently H, a substituted or unsubstituted linear or cyclic alkyl or alkenyl, a substituted or unsubstituted aryl, a substituted or unsubstituted heterocycle, or an amine-compatible protection group. Yet alternatively, one of $R^3$ and $R^4$ is linked with one of $R^1$ and $R^2$ to form a cyclic moiety in which case each of remaining groups of $R^1$, $R^2$, $R^3$, and $R^4$, as the case may be, is independently H, a substituted or unsubstituted linear or cyclic alkyl or alkenyl, a substituted or unsubstituted aryl, a substituted or unsubstituted heterocycle, or an amine-compatible protection group.

In various embodiments, the monomer units forming the amine-functionalized compound of Formula 2 are connected head to tail, head to head, tail to tail, or any combination thereof.

In various embodiments, n is in the range of 3 to 1000. In various embodiments, n is in the range of 3 to 1000. In various embodiments, n is in the range of 3 to 600. In various embodiments, n is in the range of 5 to 400.

In various embodiments, each of $X^1$, $X^2$, $X^3$, and $X^4$ is H. In various embodiments, only one of $X^1$, $X^2$, $X^3$, and $X^4$ is $CH_3$. In various embodiments, each of $X^1$ and $X^3$ is H and each of $X^2$ and $X^4$ is $CH_3$. In various embodiments, at least one of $R^1$ and $R^2$ is H. In various embodiments, at least one of $R^3$ and $R^4$ is H.

In various embodiments, when $Y^1$, $Y^2$, $Y^3$, $Y^4$, $Y^5$, $Y^6$, $Z^1$, $Z^2$, $Z^3$, or $Z^4$ is —$CR^1R^2$—NR3R4, at least one ring-carbon atom adjacent to the ring-carbon atom substituted with —$CR^1R^2$—$NR^3R^4$ is substituted with two H atoms. For example, where $Y^3$ is —$CR^1R^2$—$NR^3R^4$: each $Y^1$ and $Y^2$ is H; each of $Y^5$ and $Y^6$ is H; or each of each $Y^1$, $Y^2$, $Y^5$, and $Y^6$ is H.

In various embodiments, when $Y^1$, $Y^2$, $Y^3$, $Y^4$, $Y^5$, $Y^6$, $Z^1$, $Z^2$, $Z^3$, or $Z^4$ is —$CR^1R^2$—$NR^3R^4$, the ring-carbon atom substituted with —$CR^1R^2$—$NR^3R^4$ is further substituted with a hydrogen atom. For example, where $Y^3$ is —$CR^1R^2$—$NR^3R^4$, $Y^4$ is H.

Amine-functionalized compounds as described above may be useful as antimicrobial agents. Amine-functionalized compounds as described above may be useful for reducing fouling. Fouling may include biofouling. Amine-functionalized compounds as described above may be useful as adhesive agents. The adhesive agent may for adhering to a substrate. The substrate may be Teflon, glass, or metal.

Amine-functionalized compounds as described above may be useful as a coating, a compatibilizer, a stabilizer, metal scavenger, a membrane a gasket, an anticoagulant, a drug delivery agent, or a scavenger agent. In various embodiments, the scavenger agent is for binding pollutants during environmental remediation in marine environments. In various embodiments, the pollutants include oil, plastic particles, or a combination thereof. In various embodiments the membrane is an electrolyte membrane or a filtering membrane for water purification.

Polymers of Formulae 3, 4, and 7

This disclosure further pertains to polymers comprising an oligomer of Formula 3:

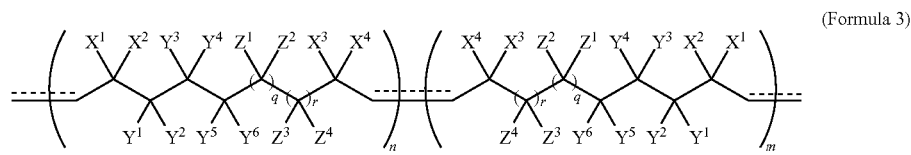

(Formula 3)

wherein --- indicates an optional double bond;
wherein each $X^1$, $X^2$, $X^3$, and $X^4$ is independently H or $CH_3$;
wherein each $Y^1$, $Y^2$, $Y^3$, $Y^4$, $Y^5$, $Y^6$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R'', and wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;
wherein each of R' and R'' is independently H, a substituted or unsubstituted linear or cyclic alkyl or alkenyl, a substituted or unsubstituted aryl, a substituted or unsubstituted heterocycle, or an amine-compatible protection group;
wherein r=0 or 1 and q=0 or 1, wherein r+q=0, 1, or 2;
wherein n and m are natural numbers; and
wherein the monomers are connected in a head to head fashion.

This disclosure further pertains to polymers comprising an oligomer of Formula 4:

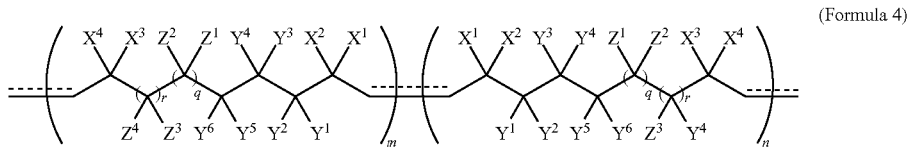

(Formula 4)

wherein --- indicates an optional double bond;
wherein each $X^1$, $X^2$, $X^3$, and $X^4$ is independently H or $CH_3$;
wherein each $Y^1$, $Y^2$, $Y^3$, $Y^4$, $Y^5$, $Y^6$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R", and wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;
wherein each of R' and R" is independently H, a substituted or unsubstituted linear or cyclic alkyl or alkenyl, a substituted or unsubstituted aryl, a substituted or unsubstituted heterocycle, or an amine-compatible protection group;
wherein r=0 or 1 and q=0 or 1, wherein r+q=0, 1, or 2;
wherein n and m are natural numbers; and
wherein the monomers are connected in a tail to tail fashion.

This disclosure further pertains to polymers comprising an oligomer of Formula 7:

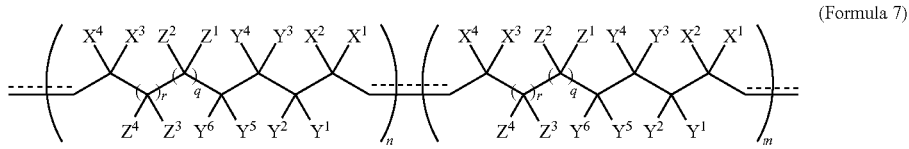

(Formula 7)

wherein --- indicates an optional double bond;
wherein each $X^1$, $X^2$, $X^3$, and $X^4$ is independently H or $CH_3$;
wherein each $Y^1$, $Y^2$, $Y^3$, $Y^4$, $Y^5$, $Y^6$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R", and wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$;
wherein each of R' and R" is independently H, a substituted or unsubstituted linear or cyclic alkyl or alkenyl, a substituted or unsubstituted aryl, a substituted or unsubstituted heterocycle, or an amine-compatible protection group;
wherein r=0 or 1 and q=0 or 1, wherein r+q=0, 1, or 2;
wherein n and m are natural numbers; and
wherein the monomers are connected in a head to tail fashion.

For oligomers of Formulae 3, 4, and 7, each of $R^1$, $R^2$, $R^3$, and $R^4$ is independently H, a substituted or unsubstituted linear or cyclic alkyl or alkenyl, a substituted or unsubstituted aryl, a substituted or unsubstituted heterocycle, or an amine-compatible protection group. Alternatively, $R^3$ and $R^4$ are linked to form a cyclic moiety, wherein each of $R^1$ and $R^2$ is independently H, a substituted or unsubstituted linear or cyclic alkyl or alkenyl, a substituted or unsubstituted aryl, a substituted or unsubstituted heterocycle, or an amine-compatible protection group. Yet alternatively, one of $R^3$ and $R^4$ is linked with one of $R^1$ and $R^2$ to form a cyclic moiety in which case each of remaining groups of $R^1$, $R^2$, $R^3$, and $R^4$, as the case may be, is independently H, a substituted or unsubstituted linear or cyclic alkyl or alkenyl, a substituted or unsubstituted aryl, a substituted or unsubstituted heterocycle, or an amine-compatible protection group.

While Formulae 3, 4, and 7 currently specify that the monomers are connected in a head to tail fashion, head to head fashion, or a tail to tail fashion, as the case may be, the skilled person will understand that the monomers could be connected in any combination thereof.

In various embodiments of polymers comprising an oligomer of Formulae 3, 4, and 7, n+m is in the range of 3 to 1000. In various embodiments, n is in the range of 3 to 1000. In various embodiments, n+m is in the range of 3 to 600. In various embodiments, n+m is in the range of 5 to 400.

In various embodiments of polymers comprising an oligomer of Formulae 3, 4, and 7, the polymer is capped with —OH, a substituted or unsubstituted $C_{1-15}$ alkyl, a substituted or unsubstituted aromatic cycle, a substituted or unsubstituted heterocycle, a functional end-group suitable for ring opening metathesis polymerization, or any combination thereof.

In various embodiments of polymers comprising an oligomer of Formulae 3, 4, and 7, each of $X^1$, $X^2$, $X^3$, and $X^4$ is H. In various embodiments of polymers of Formulae 3 and 4, only one of $X^1$, $X^2$, $X^3$, and $X^4$ is $CH_3$. In various embodiments of polymers of Formulae 3 and 4, each of $X^1$ and $X^3$ is H and each of $X^2$ and $X^4$ is $CH_3$. In various embodiments of polymers of Formulae 3 and 4, at least one of $R^1$ and $R^2$ is H. In various embodiments of polymers of Formulae 3 and 4, at least one of $R^3$ and $R^4$ is H.

In various embodiments of polymers comprising an oligomer of Formulae 3, 4, and 7, when $Y^1$, $Y^2$, $Y^3$, $Y^4$, $Y^5$, $Y^6$, $Z^1$, $Z^2$, $Z^3$, or $Z^4$ is —$CR^1R^2$—$NR^3R^4$, at least one ring-carbon atom adjacent to the ring-carbon atom substituted with —$CR^1R^2$—$NR^3R^4$ is substituted with two H atoms. For example, when $Y^3$ is —$CR^1R^2$—$NR^3R^4$: each $Y^1$ and $Y^2$ is H; each of $Y^5$ and $Y^6$ is H; or each of each $Y^1$, $Y^2$, $Y^5$, and $Y^6$ is H.

In various embodiments of polymers comprising an oligomer of Formulae 3, 4, and 7, when $Y^1$, $Y^2$, $Y^3$, $Y^4$, $Y^5$, $Y^6$, $Z^1$, $Z^2$, $Z^3$, or $Z^4$ is —$CR^1R^2$—$NR^3R^4$, the ring-carbon atom substituted with —$CR^1R^2$—$NR^3R^4$ is further substituted with a hydrogen atom. For example, where $Y^3$ is —$CR^1R^2$—$NR^3R^4$, $Y^4$ is H.

In various embodiments, the polymer has self-healing properties. In various embodiments, the polymer has adhesive properties. In various embodiments, the polymer has antimicrobial activity.

Aspects of the disclosure also pertain to block copolymers prepared by ring opening metathesis polymerization of: an amine-functionalized cycloalkene as described above; and at least one additional cycloalkene. The at least one additional cycloalkene includes norbornene or an arylamine substituted norbornene.

Aspects of the disclosure also pertain to block copolymers comprising: an amine functionalized compound as described above; and a polymer formed by radical or anionic polymerization, for which the functional end-group M of the amine functionalized compound serves as an initiation point.

Aspects of the disclosure also pertain to brush copolymers comprising a polymer as described above and polymeric bristles or brushes, wherein at least one of $X^1$, $X^2$, $X^3$, $X^4$, $Y^1$, $Y^2$, $Y^3$, $Y^4$, $Y^5$, $Y^6$, $Z^1$, $Z^2$, $Z^3$, $Z^4$, R', R'', $R^1$, $R^2$, $R^3$, and $R^4$ serves as an initiation point for subsequent synthesis of polymeric bristles or brushes.

Aspects of the disclosure also pertain to random copolymers prepared by ring opening metathesis polymerization of: an amine-functionalized cycloalkene as described above; and at least one additional cycloalkene. The at least one additional cycloalkene includes norbornene or an arylamine substituted norbornene.

Polymers as described above may be useful as antimicrobial agents. Polymers as described above may be useful for reducing fouling. Fouling may include biofouling. Polymers as described above may be useful as adhesive agents. The adhesive agent may for adhering to a substrate. The substrate may be Teflon, glass, or metal.

Polymers as described above as described above may be useful as a coating, a compatibilizer, a stabilizer, metal scavenger, a membrane a gasket, an anticoagulant, a drug delivery agent, or a scavenger agent. In various embodiments, the scavenger agent is for binding pollutants during environmental remediation in marine environments. In various embodiments, the pollutants include oil, plastic particles, or a combination thereof. In various embodiments the membrane is an electrolyte membrane or a filtering membrane for water purification.

Amine Functionalized Polyalkenes and Polyalkanes

Aspects of the disclosure also pertain to an amine functionalized polyalkene or polyalkane, wherein the polyalkene or polyalkane comprises:

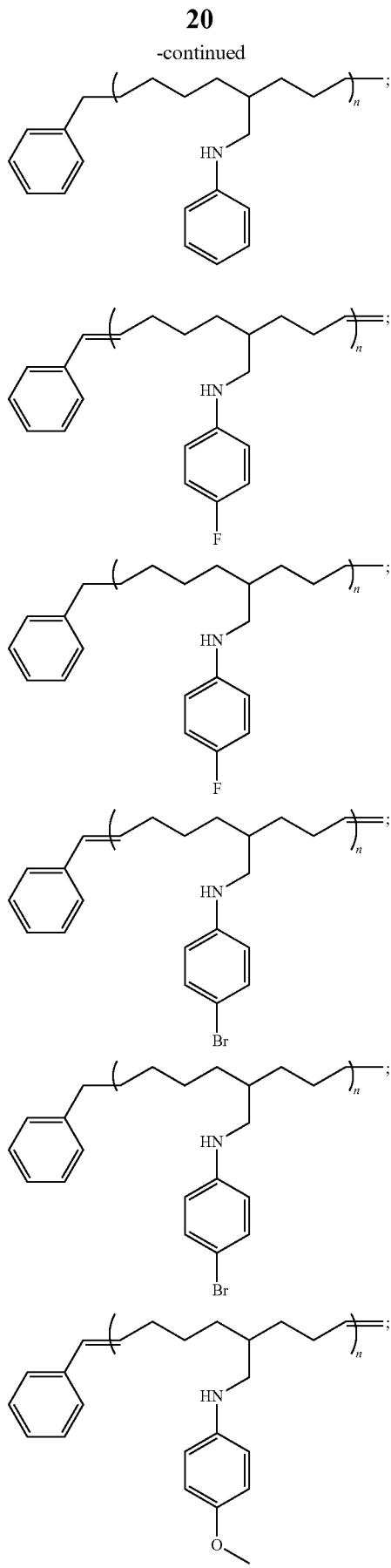

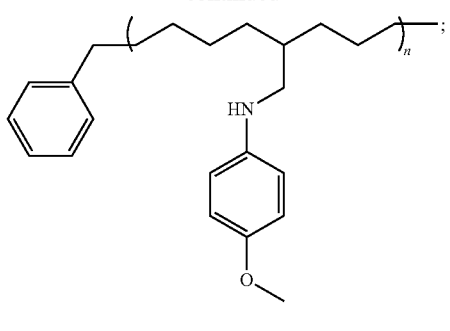

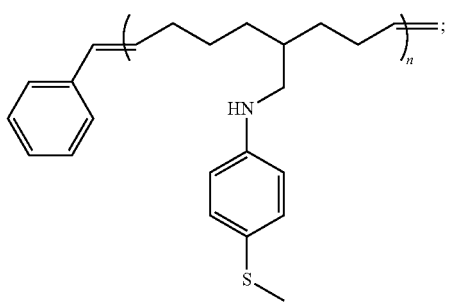

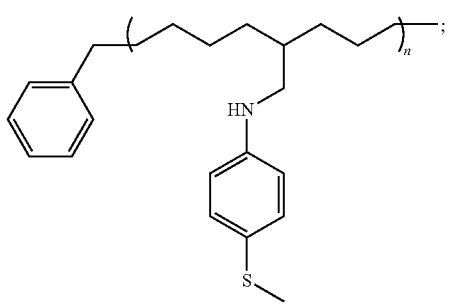

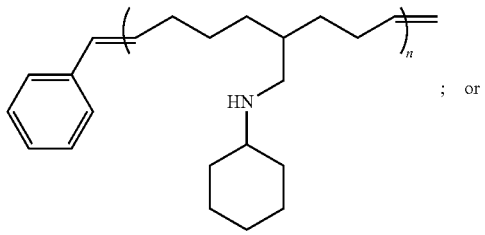

; or

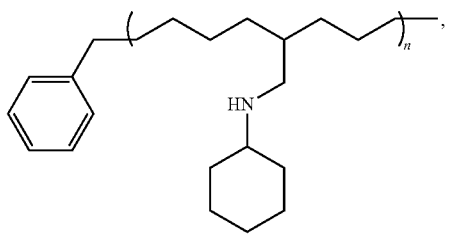

wherein n is a natural number greater than 1.

In various embodiments, n is in the range of 3 to 1000. In various embodiments, n is in the range of 3 to 600. In various embodiments, n is in the range of 5 to 400.

Aspects of the disclosure also pertain to polyalkanes of Formula 5:

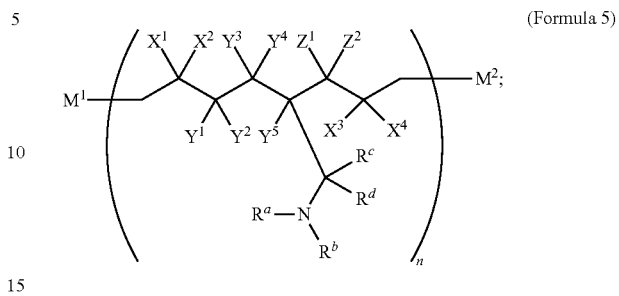

(Formula 5)

wherein each of $M^1$ and $M^2$ independently is —OH, a substituted or unsubstituted $C_{1\text{-}15}$ alkyl, a substituted or unsubstituted aromatic cycle, a substituted or unsubstituted heterocycle, or a functional end-group suitable for ring opening metathesis polymerization;

wherein each of $X^1$, $X^2$, $X^3$, and $X^4$ is independently H or $CH_3$;

wherein each of $Y^1$, $Y^2$, $Y^3$, $Y^4$, $Y^5$, $Z^1$, and $Z^2$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R";

wherein each of R' and R" is independently H, a substituted or unsubstituted linear or cyclic alkyl or alkenyl, a substituted or unsubstituted aryl, a substituted or unsubstituted heterocycle, or an amine-compatible protection group;

wherein r=0 or 1 and q=0 or 1, wherein r+q=0, 1, or 2; and wherein n is a natural greater than 1.

Each of $R^a$, $R^b$, $R^c$, and $R^d$ is independently H, a substituted or unsubstituted linear or cyclic alkyl or alkenyl, a substituted or unsubstituted aryl, a substituted or unsubstituted heterocycle, or an amine-compatible protection group. Alternatively, $R^b$ and $R^a$ are linked to form a cyclic moiety, wherein each of $R^c$, and $R^d$ is independently H, a substituted or unsubstituted linear or cyclic alkyl or alkenyl, a substituted or unsubstituted aryl, a substituted or unsubstituted heterocycle, or an amine-compatible protection group. Yet alternatively, one of $R^a$ and $R^b$ is linked with one of $R^c$ and $R^d$ to form a cyclic moiety in which case each of remaining groups of $R^a$, $R^b$, $R^c$, and $R^d$, as the case may be, is independently H, a substituted or unsubstituted linear or cyclic alkyl or alkenyl, a substituted or unsubstituted aryl, a substituted or unsubstituted heterocycle, or an amine-compatible protection group.

In various embodiments, at least one of $R^b$ and $R^a$ is H. In various embodiments, one of $R^b$ and $R^a$ is H. In various embodiments, $R^b$ is —$CR^1R^2$—$NR^3R^4$, wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group.

In various embodiments, the monomer units forming the polyalkanes of Formula 5 are connected head to tail, head to head, tail to tail, or any combination thereof.

In various embodiments, n is in the range of 3 to 1000. In various embodiments, n is in the range of 3 to 600. In various embodiments, n is in the range of 5 to 400.

In various embodiments, each of $X^1$, $X^2$, $X^3$, and $X^4$ is H. In various embodiments, only one of $X^1$, $X^2$, $X^3$, and $X^4$ is CH₃. In various embodiments, only one of $X^1$, $X^2$, $X^3$, and $X^4$ is CH₃. In various embodiments, each of $X^1$ and $X^3$ is H and each of $X^2$ and $X^4$ is CH₃. In various embodiments, at least one of $R^1$ and $R^2$ is H. In various embodiments, at least one of $R^3$ and $R^4$ is H.

Aspects of the disclosure pertain to co-polymers of Formula X:

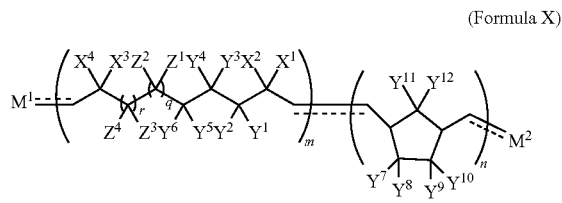

(Formula X)

wherein --- indicates an optional double bond;
wherein each of $M^1$ and $M^2$ is independently —OH, a substituted or unsubstituted $C_{1-15}$ alkyl, a substituted or unsubstituted aromatic cycle, a substituted or unsubstituted heterocycle, or a functional end-group suitable for ring opening metathesis polymerization;
wherein each $X^1$, $X^2$, $X^3$, and $X^4$ is independently H or CH₃;
wherein each $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R", and wherein at least one of $Y^1$, $Y^2$, $Y^3$, $Y^4$, $Y^5$, $Y^6$, $Z^1$, $Z^2$, $Z^3$, and $Z^4$ is —CR¹R²—NR³R⁴;
wherein each of R' and R" is independently H, a substituted or unsubstituted linear or cyclic alkyl or alkenyl, a substituted or unsubstituted aryl, a substituted or unsubstituted heterocycle, or an amine-compatible protection group;
wherein r=0 or 1 and q=0 or 1, wherein r+q=0, 1, or 2; and
wherein n and m are natural numbers; and
Each of $R^1$, $R^2$, $R^3$, and $R^4$ is independently H, a substituted or unsubstituted linear or cyclic alkyl or alkenyl, a substituted or unsubstituted aryl, a substituted or unsubstituted heterocycle, or an amine-compatible protection group. Alternatively, $R^3$ and $R^4$ are linked to form a cyclic moiety, wherein each of $R^1$ and $R^2$ is independently H, a substituted or unsubstituted linear or cyclic alkyl or alkenyl, a substituted or unsubstituted aryl, a substituted or unsubstituted heterocycle, or an amine-compatible protection group. Yet alternatively, one of $R^3$ and $R^4$ is linked with one of $R^1$ and $R^2$ to form a cyclic moiety in which case each of remaining groups of $R^1$, $R^2$, $R^3$, and $R^4$, as the case may be, is independently H, a substituted or unsubstituted linear or cyclic alkyl or alkenyl, a substituted or unsubstituted aryl, a substituted or unsubstituted heterocycle, or an amine-compatible protection group.

In various embodiments, the monomer units forming the co-polymers of Formula X are connected head to tail, head to head, tail to tail, or any combination thereof. In various embodiments, the monomer units are connected in a head to head fashion.

In various embodiments of polymers of Formulae X, n+m is in the range of 3 to 1000. In various embodiments, n+m is in the range of 3 to 600. In various embodiments, n+m is in the range of 5 to 400.

In various embodiments, each of $X^1$, $X^2$, $X^3$, and $X^4$ is H. In various embodiments, only one of $X^1$, $X^2$, $X^3$, and $X^4$ is CH₃. In various embodiments, each of $X^1$ and $X^3$ is H and each of $X^2$ and $X^4$ is CH₃. In various embodiments, at least one of $R^1$ and $R^2$ is H. In various embodiments, at least one of $R^3$ and $R^4$ is H. In various embodiments, when $Y^1$, $Y^2$, $Y^3$, $Y^4$, $Y^5$, $Y^6$, $Z^1$, $Z^2$, $Z^3$, or $Z^4$ is —CR¹R²—NR³R⁴, at least one ring-carbon atom adjacent to the ring-carbon atom substituted with —CR¹R²—NR³R⁴ is substituted with two H atoms. In various embodiments, when $Y^1$, $Y^2$, $Y^3$, $Y^4$, $Y^5$, $Y^6$, $Z^1$, $Z^2$, $Z^3$, or $Z^4$ is —CR¹R²—NR³R⁴, the ring-carbon atom substituted with —CR¹R²—NR³R⁴ is further substituted with a hydrogen atom.

Aspects of the disclosure pertain to co-polymers comprising a mixture of different amine-functionalized monomer units of Formula 6:

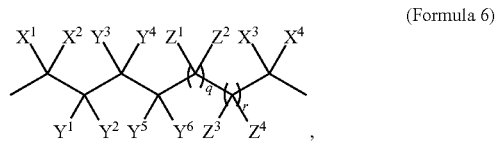

(Formula 6)

wherein --- indicates an optional double bond;
wherein each $X^1$, $X^2$, $X^3$, and $X^4$ is independently H or CH₃;
wherein each $Y^1$, $Y^2$, $Y^3$, $Y^4$, $Y^5$, $Y^6$, $Z^1$, $Z^2$, $Z^3$, and $Z^4$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R", and wherein at least one of $Y^1$, $Y^2$, $Y^3$, $Y^4$, $Y^5$, $Y^6$, $Z^1$, $Z^2$, $Z^3$, and $Z^4$ is —CR¹R²—NR³R⁴;
wherein each of R' and R" is independently H, a substituted or unsubstituted linear or cyclic alkyl or alkenyl, a substituted or unsubstituted aryl, a substituted or unsubstituted heterocycle, or an amine-compatible protection group; and
wherein r=0 or 1 and q=0 or 1, wherein r+q=0, 1, or 2.

Each of $R^1$, $R^2$, $R^3$, and $R^4$ is independently H, a substituted or unsubstituted linear or cyclic alkyl or alkenyl, a substituted or unsubstituted aryl, a substituted or unsubstituted heterocycle, or an amine-compatible protection group. Alternatively, $R^3$ and $R^4$ are linked to form a cyclic moiety, wherein each of $R^1$ and $R^2$ is independently H, a substituted or unsubstituted linear or cyclic alkyl or alkenyl, a substituted or unsubstituted aryl, a substituted or unsubstituted heterocycle, or an amine-compatible protection group. Yet alternatively, one of $R^3$ and $R^4$ is linked with one of $R^1$ and $R^2$ to form a cyclic moiety in which case each of remaining groups of $R^1$, $R^2$, $R^3$, and $R^4$, as the case may be, is independently H, a substituted or unsubstituted linear or cyclic alkyl or alkenyl, a substituted or unsubstituted aryl, a substituted or unsubstituted heterocycle, or an amine-compatible protection group.

In various embodiments, the monomer units of formula 6 forming the co-polymer are connected head to tail, head to head, tail to tail, or any combination thereof.

In various embodiments the number of monomer units of formula 6 forming the polymer is in the range of 3 to 1000. In various embodiments the number of monomer units of formula 6 forming the polymer is in the range of 3 to 600. In various embodiments, n+m is in the range of 5 to 400.

In various embodiments, each of $X^1$, $X^2$, $X^3$, and $X^4$ is H. In various embodiments, only one of $X^1$, $X^2$, $X^3$, and $X^4$ is CH₃. In various embodiments, each of $X^1$ and $X^3$ is H and each of $X^2$ and $X^4$ is CH₃. In various embodiments, at least one of $R^1$ and $R^2$ is H. In various embodiments, at least one of $R^3$ and $R^4$ is H. In various embodiments, when $Y^1$, $Y^2$, $Y^3$, $Y^4$, $Y^5$, $Y^6$, $Z^1$, $Z^2$, $Z^3$, or $Z^4$ is —CR¹R²—NR³R⁴, at least one ring-carbon atom adjacent to the ring-carbon atom substituted with —CR¹R²—NR³R⁴ is substituted with two H atoms. In various embodiments, when $Y^1$, $Y^2$, $Y^3$, $Y^4$, $Y^5$, $Y^6$, $Z^1$, $Z^2$, $Z^3$, or $Z^4$ is —CR¹R²—NR³R⁴, the ring-carbon atom substituted with —CR¹R²—NR³R⁴ is further substituted with a hydrogen atom.

Various polyalkene or polyalkanes as described above may be useful as an antimicrobial agent. Various polyalkene or polyalkanes as described above may be useful for reducing fouling. Fouling may include biofouling. Various polyalkene or polyalkanes as described above may be useful as an adhesive agent. The adhesive agent may for adhering to a substrate. The substrate may be Teflon, glass, or metal.

Various polyalkene or polyalkanes as described above may be useful as a coating, a compatibilizer, a stabilizer, metal scavenger, a membrane a gasket, an anticoagulant, a drug delivery agent, or a scavenger agent. In various embodiments, the scavenger agent is for binding pollutants during environmental remediation in marine environments. In various embodiments, the pollutants include oil, plastic particles, or a combination thereof. In various embodiments the membrane is an electrolyte membrane or a filtering membrane for water purification.

Substrates

Aspects of the disclosure pertain to a substrate coated with a polyalkene or polyalkane, amine-functionalized compound, or polymer as described above.

In various embodiments, the substrate reduces biofouling.

Methods of Preparing Polymers

The novel amine-containing polymers disclosed herein are enabled by the presently developed and disclosed catalytic synthesis using a combination of hydroaminoalkylation and ring-opening metathesis polymerization (ROMP) using Grubbs second generation catalyst ("G2"). This preparation transforms commercially available starting materials to a rich and diverse class of novel polymers without the use of additives or directing/protecting groups, thereby minimizing waste generation. The development of this atom-economic, gram-scale preparation was conducted for a series of secondary aryl-amine containing cyclooctene derivatives. The preparation of such amine-functionalized polyethylene analogs comprises two, and optionally three, steps. First, monomers are synthesized by the catalytic hydroaminoalkylation of a cycloalkene, e.g. cyclooctadiene, an alkene aminoalkylation reaction that proceeds in an atom-economic fashion. This methodology avoids amine directing or protecting groups (see FIG. 2). Secondly, these amine-containing monomers are then polymerized using ROMP to provide linear poly(cyclooctene) with pendant secondary amines (see FIG. 3). Thirdly and optionally, subsequent alkene hydrogenative reduction then furnished amine functionalized polyethylene in which every eighth carbon contains a secondary amine functional group.

Aspects of the disclosure pertain to methods of preparing polyalkanes of Formula 5 as defined above, methods of preparing amine-functionalized compounds as defined above, methods of preparing a polyalkene or polyalkane of as defined above, or methods of preparing a polymer comprising an oligomer of Formula 3, Formula 4, or Formula 7 as defined above. These methods comprise: (i) contacting a cycloalkene with a secondary amine containing moiety in the presence of a group 5 metal based catalytic complex to obtain a hydroaminoalkyl-substituted cycloalkene; (ii) performing ring-opening metastasis polymerization of said hydroaminoalkyl-substituted cycloalkene to obtain an amine-functionalized polyalkene; and, optionally, (iii) hydrogenating said amine-functionalized polyalkene from step (ii) to obtain the amine-functionalized polyalkane of Formula 5, the polyalkene, polyalkane, or polymer as the case may be.

Aspects of the disclosure further pertain to a method of preparing an amine-functionalized cycloalkene of Formula 1, said method comprising: (i) contacting a cycloalkene with a secondary amine containing moiety in the presence of a group 5 metal based catalytic complex to obtain a hydroaminoalkyl-substituted cycloalkene.

In various embodiments of the methods described above, the secondary amine-containing moiety comprises at least two α-sp³ hybridized C—H bonds. In various embodiments, the secondary amine-containing moiety is a $C_4$-$C_{100}$ linear, branched, or cyclic alkyl, optionally substituted and/or comprising heterotaoms. In various embodiments, the secondary amine-containing moiety is substituted with a halogen, an ether, another amine, an alkyl, an alkene, an acetal, a phosphine, an amide, an alkyne, an imine, a nitrile, an isocyanide, an epoxide, a boronic acid ester; a phenyl that optionally may be substituted and/or part of a condensed ring system, or any combination thereof. In various embodiments, the secondary amine-containing moiety is: pyrrolidine; piperidine;

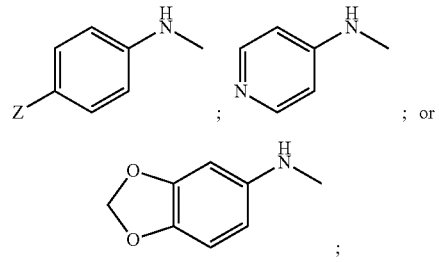

wherein Z is H, OCF₃, F, Cl, Br, I, or OCH₃. In various embodiments, the secondary amine-containing moiety is:

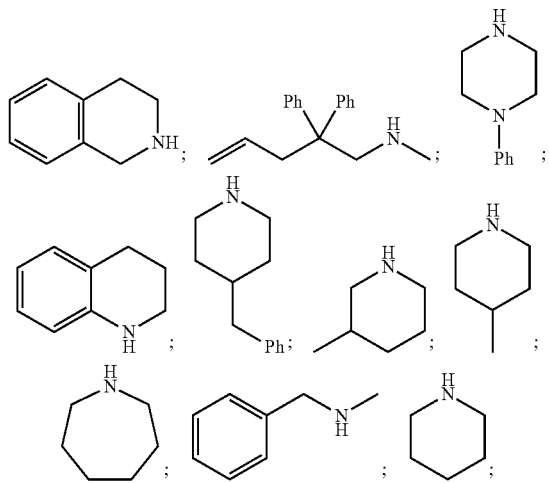

27

-continued

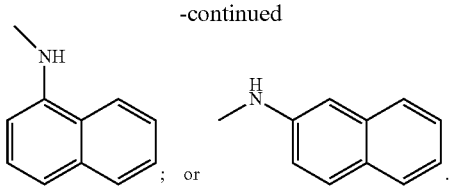
; or .

Cycloalkenes

In various embodiments of the methods disclosed above, the cycloalkene contacted with the secondary amine containing moiety is cyclooctadiene. However, the skilled person would understand other cycloalkenes could be used in the context of this disclosure.

Catalyst Complexes

In various embodiments of the methods disclosed above, the group 5 metal based catalytic complex has the structure of Formula I:

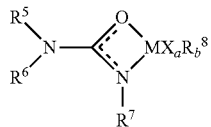

(Formula I)

wherein:

$R^5$ and $R^6$ are:
    each independently: H; a $C_1$-$C_{40}$ substituted or unsubstituted linear, branched or cyclic alkyl or alkenyl or alkynyl; a substituted or unsubstituted aryl; or a substituted or unsubstituted heterocyclic group; or bonded together thereby forming, together with the nitrogen atom they are both bound to, a heterocycle;

$R^7$:
    is H; a $C_1$-$C_{40}$ substituted or unsubstituted linear, branched or cyclic alkyl or alkenyl or alkynyl; or a substituted or unsubstituted aryl; or a substituted or unsubstituted heterocyclic group; or bonded together with $R^5$ and/or $R^6$ to form a heterocycle.

M is a group 5 metal;

a=0 to 4 and b=0 to 4, wherein the sum of a and b is 4;

each X is a halogen substituent;

each $R^8$ is independently: H; or a $C_1$-$C_{20}$ substituted or unsubstituted, linear, branched or cyclic alkyl, optionally comprising heteroatoms. In various embodiments, each X is independently Cl or Br. In various embodiments, a=1 or a=2.

In various embodiments, $R^5$ and $R^6$ are each independently: methyl; ethyl; isopropyl; cyclohexyl; phenyl; 2,6-dimethyl phenyl; 2,4,6-trimethyl phenyl; 4-methyl phenyl; optionally substituted piperidine; optionally substituted pyrrolidine; or substituted morpholine.

In various embodiments, $R^5$ and $R^6$ are bonded together to form, together with the nitrogen atom they are both bound to, a 6-membered ring, which optionally may be substituted.

In various embodiments: $R^5$ and $R^6$ are each phenyl; $R^5$ is phenyl and $R^6$ is isopropyl; $R^5$ and $R^6$ are bonded together to form, together with the nitrogen atom they are both bound to, piperidinyl; $R^5$ is phenyl and $R^6$ is methyl; $R^5$ is methyl and $R^6$ is 1-phenylethyl; $R^5$ is methyl and $R^6$ is isopropyl; or $R^5$ is phenyl and $R^6$ is diphenylmethyl.

28

In various embodiments, $R^7$ is: phenyl; 2,6-dimethyl phenyl; 2,6-di(isopropyl) phenyl; or

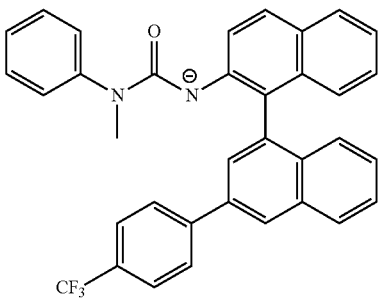

In various embodiments, $R^7$ is bonded together with $R^5$ and/or $R^6$ to form, together with each of the nitrogen atoms they are bound to, a 5-membered ring, which optionally may be substituted. $R^7$ is bonded together with $R^5$ and/or $R^6$, and each of the nitrogen atoms they are bound to, to form:

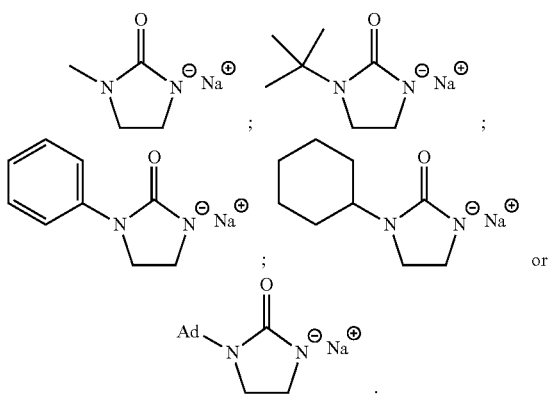

or

In various embodiments, $R^8$ is —$CH_3$, —$NMe_2$, —$CH_2C(CH_3)_3$, or —$CH_2Si(CH_3)_3$.

In various embodiments, M is tantalum (Ta), niobium (Nb), or vanadium (V).

In various embodiments of the methods disclosed above, the group 5 metal based catalytic complex has the structure of Formula II

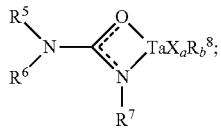

(Formula II)

wherein:

$R^5$ and $R^6$ are:
    each independently: methyl; ethyl; isopropyl; cyclohexyl; phenyl; 2,6-dimethyl phenyl; 2,4,6-trimethyl phenyl; 4-methyl phenyl; optionally substituted piperidine; optionally substituted pyrrolidine; or substituted morpholine; or
    bonded together to form, together with the nitrogen atom they are both bound to, a 6-membered ring, which optionally may be substituted;

R[7] is:
 phenyl; 2,6-dimethyl phenyl; or 2,6-di(isopropyl) phenyl; or bonded together with R[5] and/or R[6] to form, together with each of the nitrogen atoms they are bound to, a 5-membered ring, which optionally may be substituted;

each X is independently Cl or Br;

a=1 or 2 and b=(4−a); and

R[8] is —CH$_3$, —NMe$_2$, —CH$_2$C(CH$_3$)$_3$, or —CH$_2$Si(CH$_3$)$_3$.

In various embodiments, the group 5 metal based catalytic complex is:

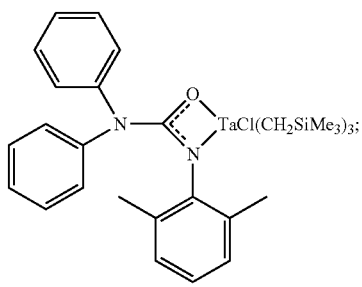

(Formula III)

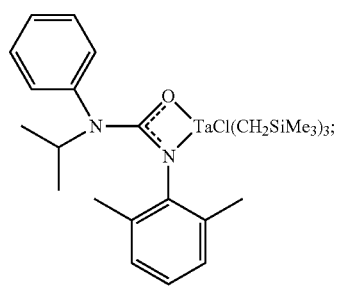

(Formula IV)

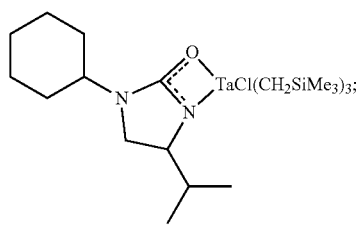

(Formula V)

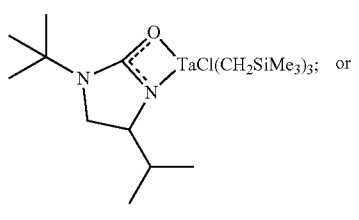

(Formula VI)

Chlorotris(dimethylamido)(κ$^2$-N,O-3-methyl-2-pyridonato)tantalum. (V)

The reaction conditions may include a reaction temperature in the range from 50° C. to 200° C., a reaction temperature in the range from 75° C. to 165° C., a reaction temperature in the range from 90° C. to 150° C., a reaction temperature in the range from range from 110° C. to 130° C., a reaction temperature of about 110° C., or a reaction temperature of about 130° C.

The reaction conditions may include a solvent. The solvent may be non-protic. The solvent may be toluene, benzene, or a mixture thereof.

The secondary amine-containing moiety and said cycloalkene may be provided in a stoichiometric ratio from 0.1 to 1.5. The secondary amine-containing moiety and said cycloalkene may be provided in a stoichiometric ratio of about 1:1.

EXAMPLES

Various alternative embodiments and examples are described herein. These embodiments and examples are illustrative and should not be construed as limiting the scope of the invention. In particular, while tantalum was used as the representative group 5 metal for these studies, the skilled person will expect other group 5 metals, and especially niobium, to perform similarly.

Materials and Methods

The procedures described herein are given for the purposes of example and illustration only and should not be considered to limit the spirit or scope of the invention.

1. General

All reactions were performed under an inert atmosphere using a Schlenk double manifold equipped with N$_2$ and high vacuum (10$^{-3}$ mbar) or a glovebox filled with N$_2$. All glassware used was heated above 160° C. in an oven prior to use. Reactions were performed in threaded 20 mL scintillation vials equipped with a Teflon-coated magnetic stir bar and a Teflon-lined polypropylene screw-cap. Toluene and hexane were purified by passing over activated alumina columns prior to collection and storage in the glovebox. Thin layer chromatography (TLC) was performed on EMD Silica gel 60 F254 plates and visualized under a 254 nm UV light. Flash chromatography was performed using an automated Biotage purification system using SilicaFlash F60 silica gel (230-400 mesh) (Silicycle) as a stationary phase and ACS grade Flexanes/Ethyl Acetate as a mobile phase.

2. Reagents

All reagents were purchased from commercial sources. 3-methyl 2-pyridone (Combi-blocks) was purified by sublimation. Cyclooctadiene (Aldrich), N-methyl aniline (Aldrich), 4-fluoro N-methyl aniline (Aldrich), and 4-bromo N-methyl aniline (Oakwood) were stirred over CaH$_2$ for a minimum of 2 h, separated by distillation, then manipulated using standard Schlenk techniques. 4-methoxy N-methyl aniline was prepared as according to literature and purified via sublimation. [TaCl$_2$(NMe$_2$)$_3$] and Chlorotris(dimethylamido)(κ$^2$-N,O-3-methyl-2-pyridonato)tantalum(V) were prepared as per literature precedent. Grubbs Catalyst™ 2nd Generation (Sigma-Aldrich) was purchased and used without further purification.

3. Instrumentation

NMR Spectroscopy. $^1$H NMR spectra were recorded on Bruker 300 MHz, or 400 MHz, Avance spectrometers at ambient temperature at 293 K. $^{13}$C and $^{19}$F NMR spectra were recorded on a Bruker Avance 300 instrument at 293 K. Chemical shifts (δ) are reported in parts per million (ppm). Coupling constants J are given in Hertz (Hz). The following abbreviations are used to indicate signal multiplicity: s=singlet; d=doublet; dd=doublet of doublets; t=triplet;

q=quartet; m=multiplet; br=broad; appt=apparent. Assignment of the signals was carried out using 1D ($^1$H, $^{13}$C{$^1$H}) and 2D (COSY, HSQC and HMBC) NMR experiments.

Infrared (IR) Spectroscopy. Spectra were recorded at room temperature on a Perkin Elmer FTIR equipped with an ATR accessory for direct measurement on oils and polymeric materials. Bands are reported in wavenumbers (cm$^{-1}$) and assigned with the abbreviations s=strong, m=medium, w=weak, sh=shoulder, br=broad.

Gel Permeation Chromatography. Polymer $M_n$, $M_w$ and dispersity (Đ) were obtained using triple detection gel permeation chromatography (GPC) using a Waters liquid chromatograph equipped with an Agilent 1200 series isocratic pump and autosampler, Phenomenex Phenogel 5 μm narrow bore columns, Wyatt OptilabEx differential refractometer, Wyatt tristar miniDAWN (laser light scattering detector) and a Wyatt ViscoStar viscometer. A flow rate of 0.5 ml·min-1 was used and samples were dissolved in THF (~2 mg·ml$^{-1}$). The measurements were carried out at a laser wavelength of 690 nm, at 25° C. The data was analyzed using the Astra® processing program provided by Wyatt Technology Corp.

Differential Scanning Calorimetry (DSC). DSC was done on a TA Instruments DSC Q2000 equipped with a TA Instruments Refrigerated Cooling System 90. A heating/cooling rate of 5° C./min was used for each run in the range of −90° C. to 120° C. Duplicate runs were measured after the completion of one heating/cooling cycle to remove thermal history.

Thermogravimetric Analysis (TGA). A thermogravimetric analyzer, model Shimadzu TGA-60, was used for TG measurements of the samples. A small amount (3-5 mg) was analyzed using the alumina crucible. The samples were pre-heated at 105° C. for 15 min in the TGA furnace to remove moisture. Then, the samples were tested from 30° C. to 600° C. at a rate of 10° C./min under the nitrogen atmosphere.

Rheological Measurements. Rheological characterization was conducted using the Anton Paar MCR 702 rotational rheometer, equipped with a cone-partitioned-plate geometry. The main advantage of this geometry is the elimination of the edge fracture[29]. The top part of this type of geometry contains an 8 mm in diameter plate attached to the transducer (center plate), and a coaxial stationary ring (partitioned plate, 25 mm in diameter), which acts as a shield and prevents edge fracture of the sample. The bottom plate is 25 mm in diameter with an angle of 0.07 rad. The experiments were performed at distance gap of 51 μm.

The thermal stability of the samples was monitored isothermally for 2 hrs by applying the frequency of 0.1 Hz and shear strain of 0.01. An initial strain sweep test at the frequency of 0.1 Hz was used to determine the threshold of the linear viscoelastic region. Frequency sweep experiments (0.01-100 Hz) at a fixed shear strain of 0.01 were performed at different temperatures, which allows using the time-temperature superposition principle (tTS) and generating the master curve for each sample at the reference temperatures. Experiments were conducted in triplicate, and representative data is presented.

4. Synthesis and Results

General methods of synthesizing Group V metal catalyst complexes useful in the context of the present disclosure, including Chlorotris(dimethylamido)(κ2-N,O-3-methyl-2-pyridonato)tantalum(V), are described in international patent application no. PCT/CA2018/050619, which published as WO 2018/213938, the contents of which are incorporated herein by reference.

4.1 Chlorotris(dimethylamido)(κ$^2$-N,O-3-methyl-2-pyridonato) tantalum(V)

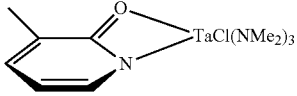

To a suspension of [TaCl$_2$(NMe$_2$)$_3$]$_2$ (0.23 g, 0.3 mmol) in toluene (~2 mL) was added a suspension of sodium 3-methyl-2-pyridonate (0.075 g, 0.6 mmol) in toluene (~2 mL) at room temperature. Upon stirring overnight, the initially yellow, cloudy mixture became an orange, clear solution. Volatiles were removed in vacuo to give 0.250 g orange-brown oil (90%). The crude residue was dissolved in 1.0 g toluene solvent (0.25 w/w %) and used for hydroaminoalkylation (HAA). $^1$H NMR (400 MHz, d$_8$-tol): δ 8.23 (d of d, 1H, ArH), δ 6.83 (d, 1H, ArH), δ 6.20 (t, 1H, ArH), δ 3.75-3.53 (br s, 18H, (NCH$_3$)$_2$)$_3$) δ 2.10 (s, 3H, CH$_3$). Characterization was consistent with previously reported values.

4.2 Hydroaminoalkylation Reaction

Figure 2:
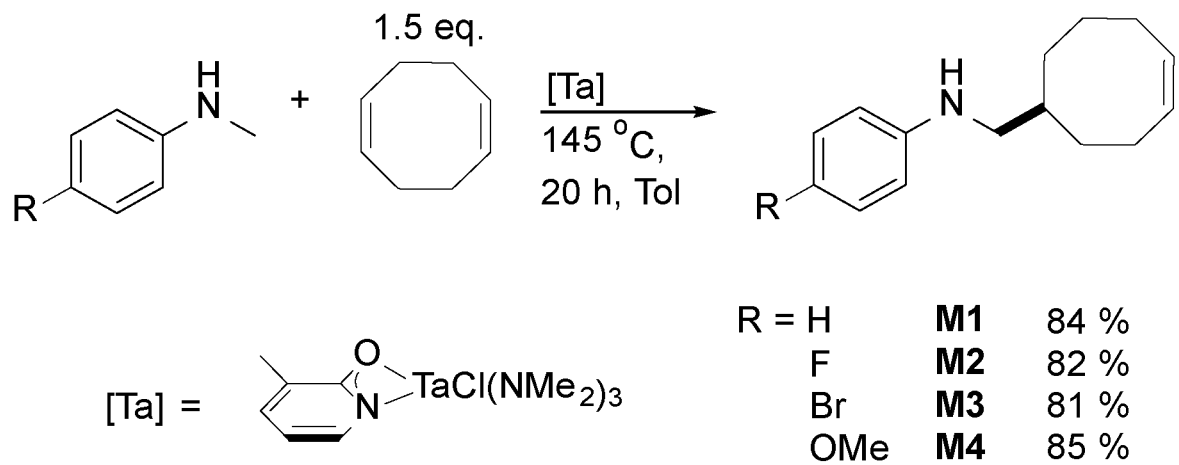
FIG. 2 is a diagram depicting hydroaminoalkylation of cyclooctadiene to access amine-functionalized cyclooctadiene derivatives according to embodiment of the disclosure. Gravimetric yields reported post-chromatography (%).

FIG. 2 depicts the general scheme for hydroaminoalkylation of cycloalkenes according to the present disclosure. Hydroaminoalkylated monomers derived from cyclooctadiene were prepared by hydroaminoalkylation using catalyst Chlorotris(dimethylamido)(κ$^2$-N,O-3-methyl-2-pyridonato) tantalum(V). While Chlorotris(dimethylamido)(κ$^2$-N,O-3-methyl-2-pyridonato)tantalum(V) was used exclusively in the embodiments exemplified herein for simplicity, the skilled person will understand that other group 5 metal based catalytic complexes as described herein may be useful in the production of the amine-functionalized cycloalkenes and polymers disclosed herein. Similarly, the skilled person will understand that although cyclooctadience was used exclusively in the embodiments exemplified herein, additional cycloalkenes may be useful in the production of the amine-functionalized cycloalkenes and polymers disclosed herein. All reported yields are calculated post-column chromatography.

Referring to FIG. 2, the catalyst complex demonstrated yielding and multigram scale reactivity (see FIG. 2). Using this catalytic system, a variety of para-substituted N-methyl anilines were used to access 4 different amine functionalized monomers (M1-M4), including halides and methoxy functionalized aniline substituents. By using a slight excess of cyclooctadiene (1.5 equivalent), only small amounts of b/s-alkylated product were formed as a minor by-product (<15%), and then removed by column chromatography to give high yields of the desired aminated cyclooctene monomers in high yield (>81%).

(Z)—N-(cyclooct-4-en-1-ylmethyl)aniline (amine-functionalized cycloalkene "M1"). To a solution of Chlorotris(dimethylamido)(κ$^2$-N,O-3-methyl-2-pyridonato)tantalum (V) (200 mg, 5 mol %) in toluene (~3 mL) was added N-methyl aniline (1 g, 9.34 mmol) followed by cyclooctadiene (1.54 g, 14 mmol). The initially orange, cloudy solution was equipped with a stirring bar, capped, removed from the glovebox, and heated to 145° C. in an oil-bath.

Figure 7A:
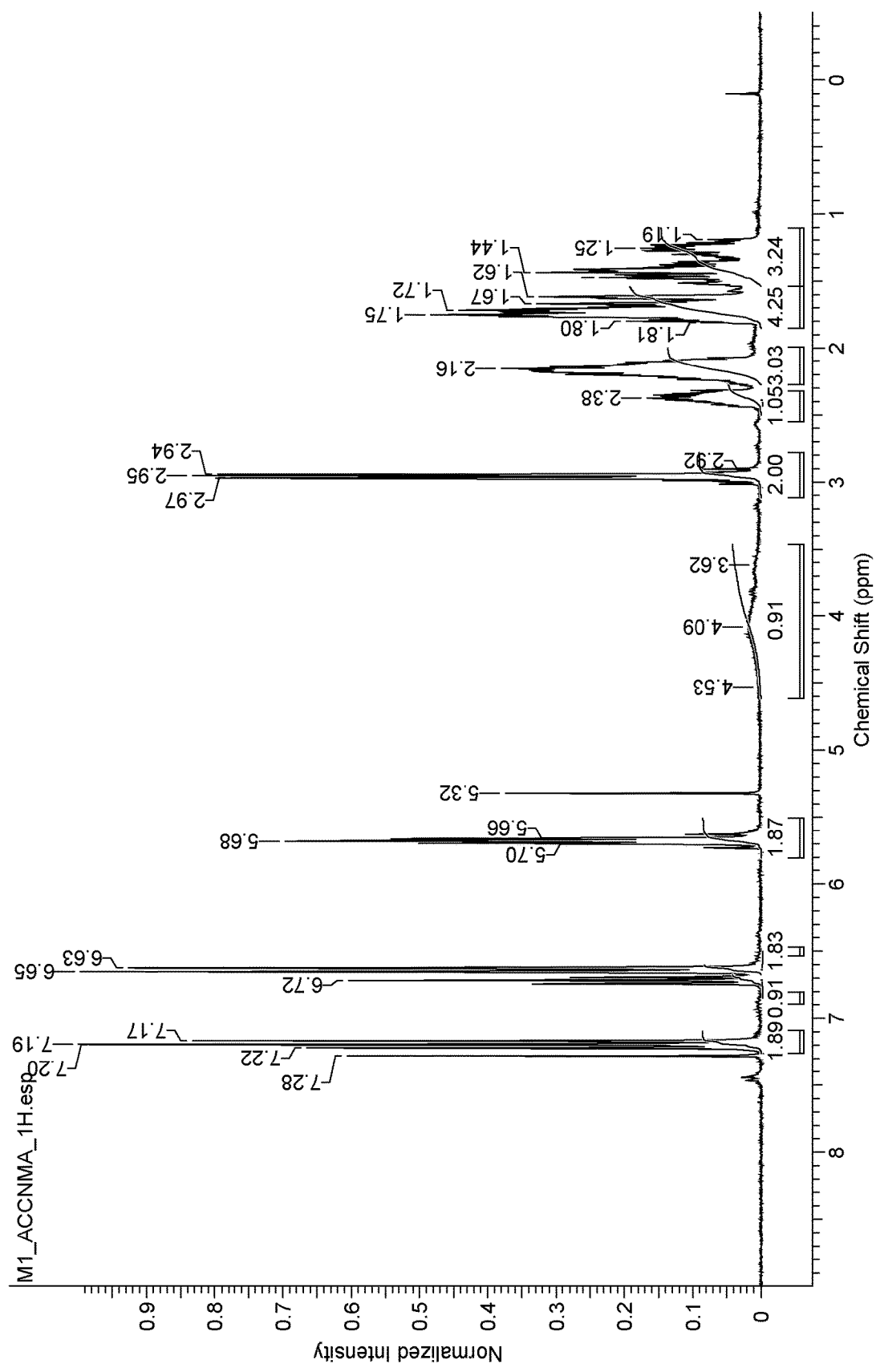
FIG. 7a is a $^1$H-NMR spectrum (300 MHz) of amine-functionalized cycloalkene "M1" of the present disclosure in CDCl$_3$ at 293 K.
Figure 7B:
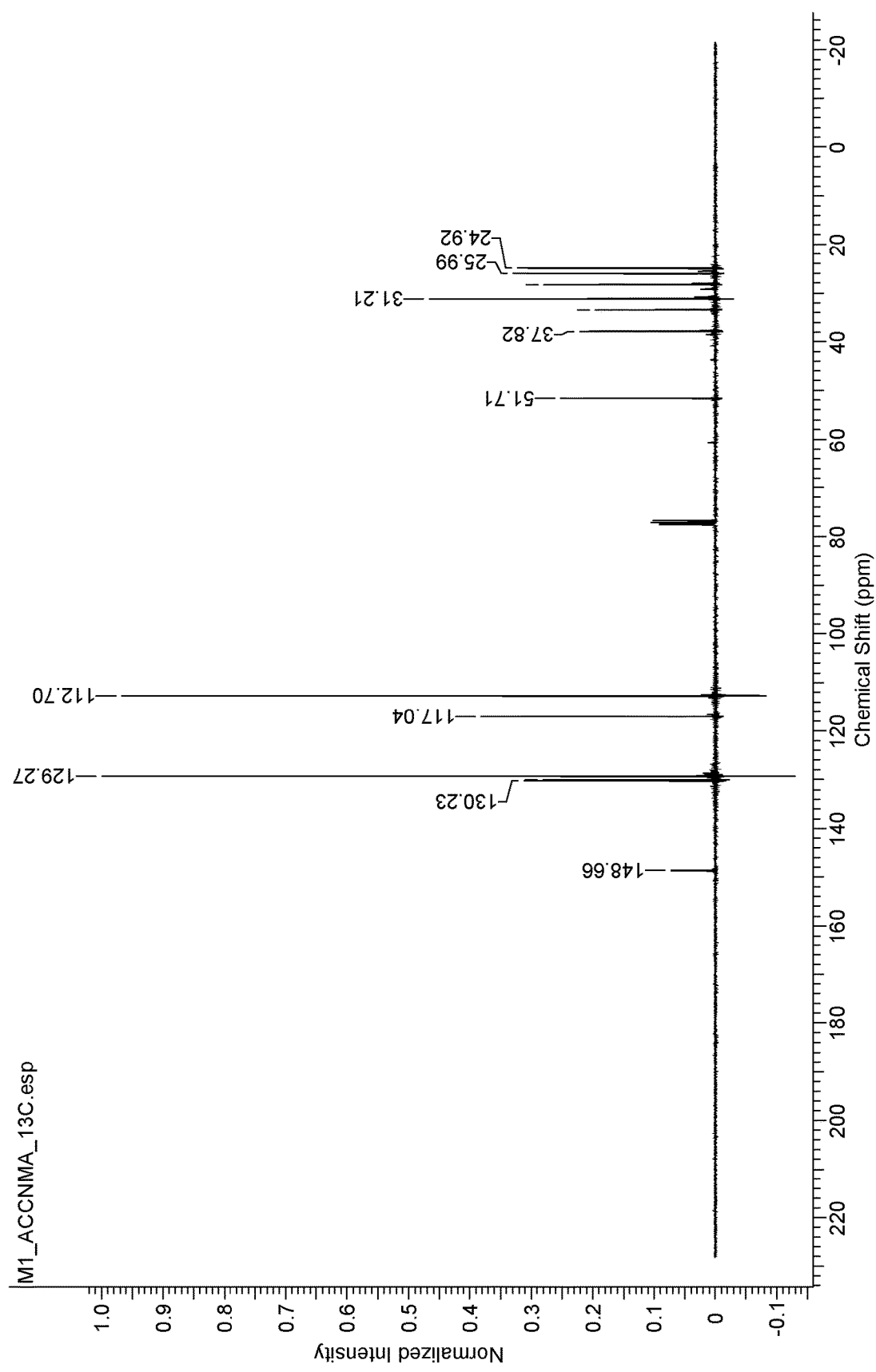
FIG. 7b is a $^{13}$C-NMR spectrum (75 MHz) of amine-functionalized cycloalkene "M1" of the present disclosure in CDCl$_3$ at 293 K.

Upon reaching temperature the reaction mixture goes dark red and was then heated with stirring for 20 h. After this time, the reaction was quenched with exposure to ambient atmosphere and the addition of 1 mL methanol. Purification was completed via automated column chromatography (0 to 20% gradient of ethyl acetate/hexanes) to afford 1.68 g of pale-yellow oil (84.0%). $^1$H NMR (300 MHz, CDCl$_3$, FIG. 7a): δ 7.20 (d of d, $^3J_{AB}$=7.35 Hz, $^3J_{AC}$=8.53 Hz, 2H, 2×ArH), δ 6.72 (t, $^3J_{AB}$=7.39 Hz, 1H, ArH), δ 6.64 (d, $^3J_{AC}$=8.79 Hz, 2H, 2×ArH), δ 5.68 (m, 2H, 2×RHC=CHR), δ 4.09 (br s, 1H, NH), δ 2.96 (m, 2H, CH$_2$), δ 2.38 (m, 1H, CH), δ 2.16 (m, 3H, CH$_2$), δ 1.81-1.19 (m, 7H, CH$_2$) $^{13}$C{1H} NMR (75 MHz, CDCl$_3$, FIG. 7b): δ 148.7 (C), δ 130.2 (CH), δ 130.1 (CH), δ 129.3 (CH), δ 117.0 (CH), δ 112.7 (CH), δ 51.7 (CH$_2$), δ 37.8 (CH$_2$), δ 33.5 (CH$_2$), δ 31.2 (CH$_2$), δ 28.3 (CH), δ 26.0 (CH), δ 24.9 (CH) IR (neat oil, cm$^{-1}$, int): 3428br, 3019w, 2924s, 2856sh, 1600s, 1506s, 1314m, 1252w, 1125br, 994br, 749s, 689s HRMS-ESI (m/z) Calcd: 216.1752; found: 216.748.

Figure 8A:
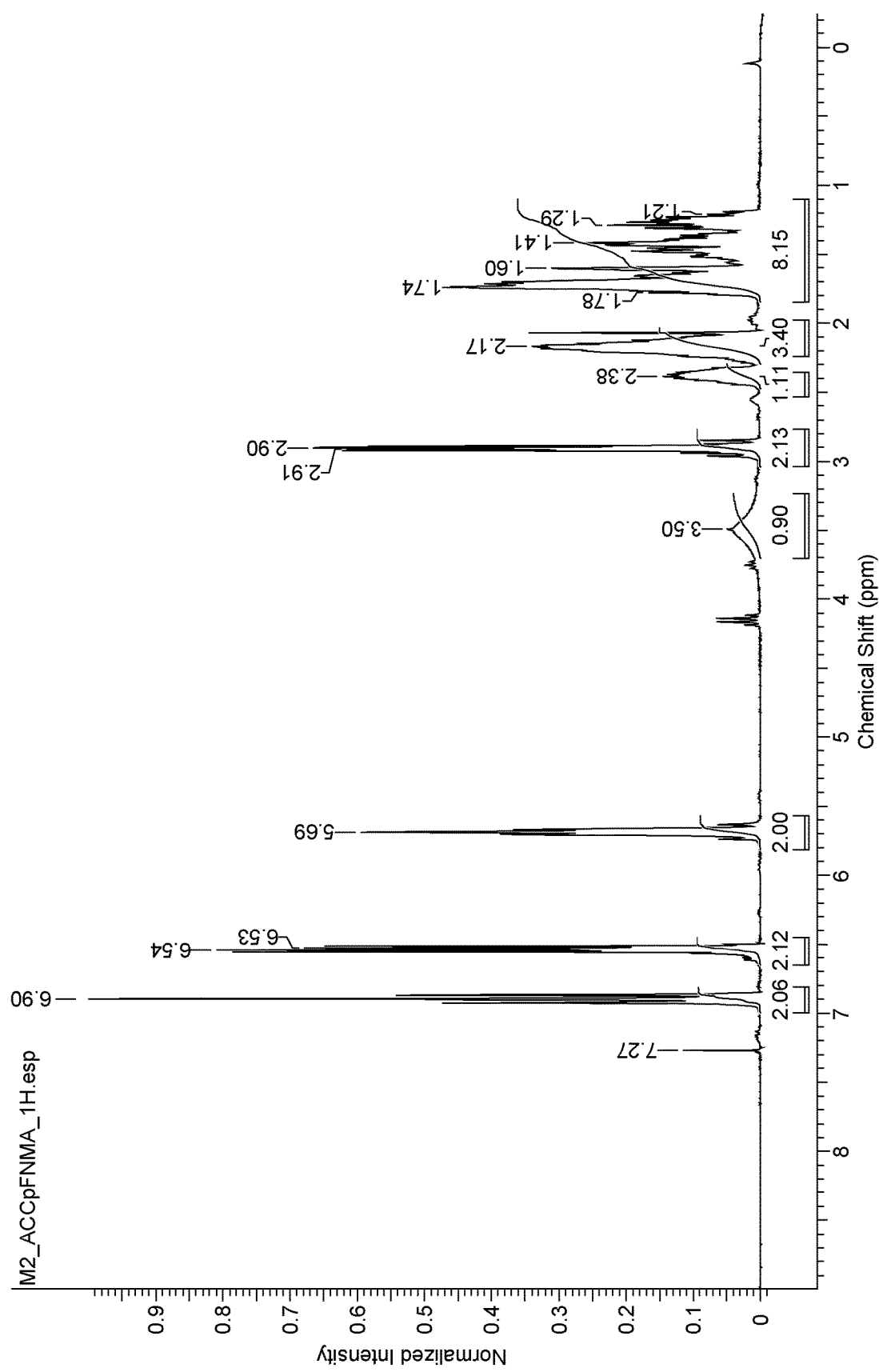
FIG. 8a is a $^1$H-NMR spectrum (300 MHz) of amine-functionalized cycloalkene "M2" of the present disclosure in CDCl$_3$ at 293 K.
Figure 8B:
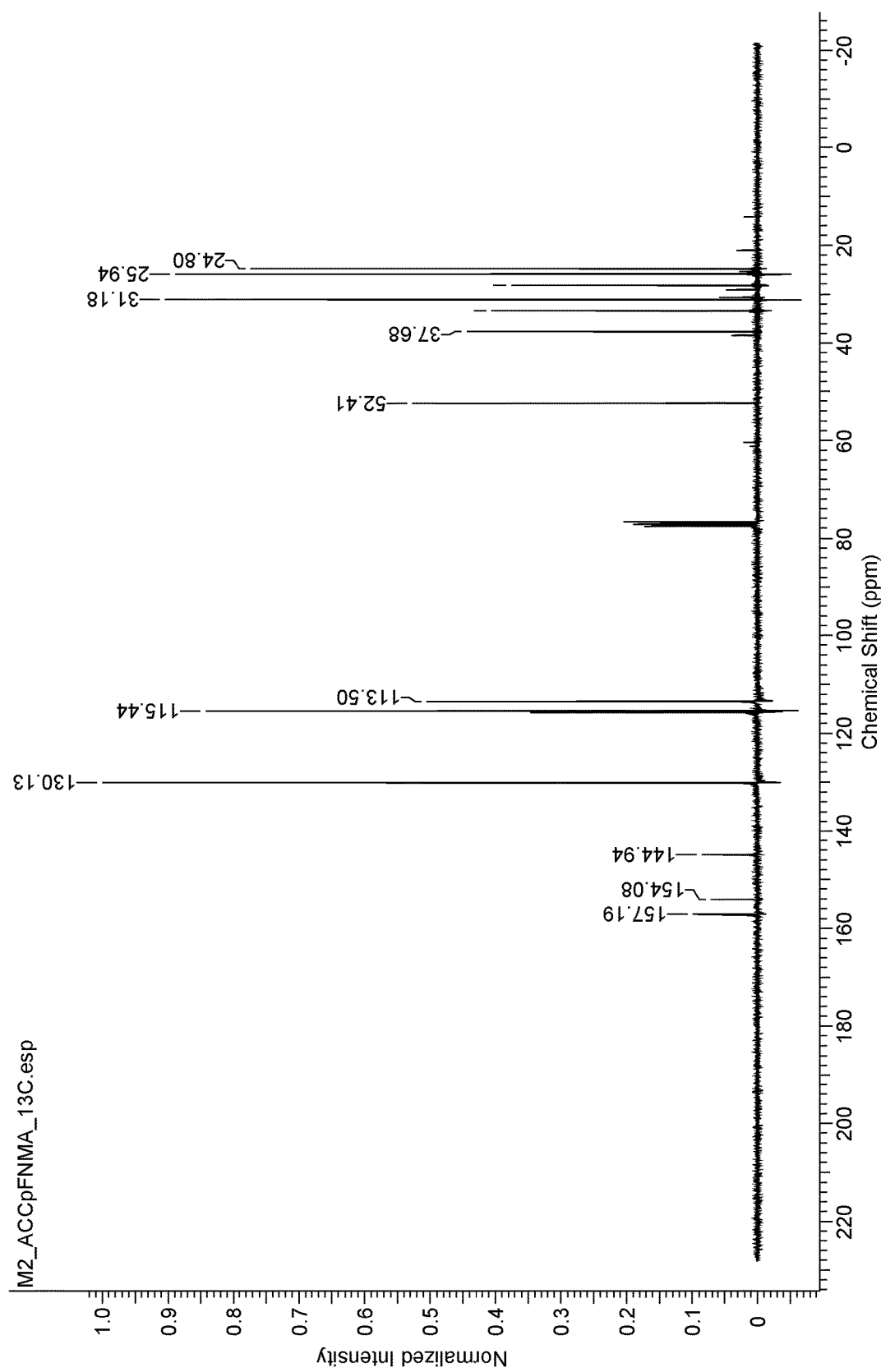
FIG. 8b is a $^{13}$C-NMR spectrum (75 MHz) of amine-functionalized cycloalkene "M2" of the present disclosure in CDCl$_3$ at 293 K.
Figure 8C:
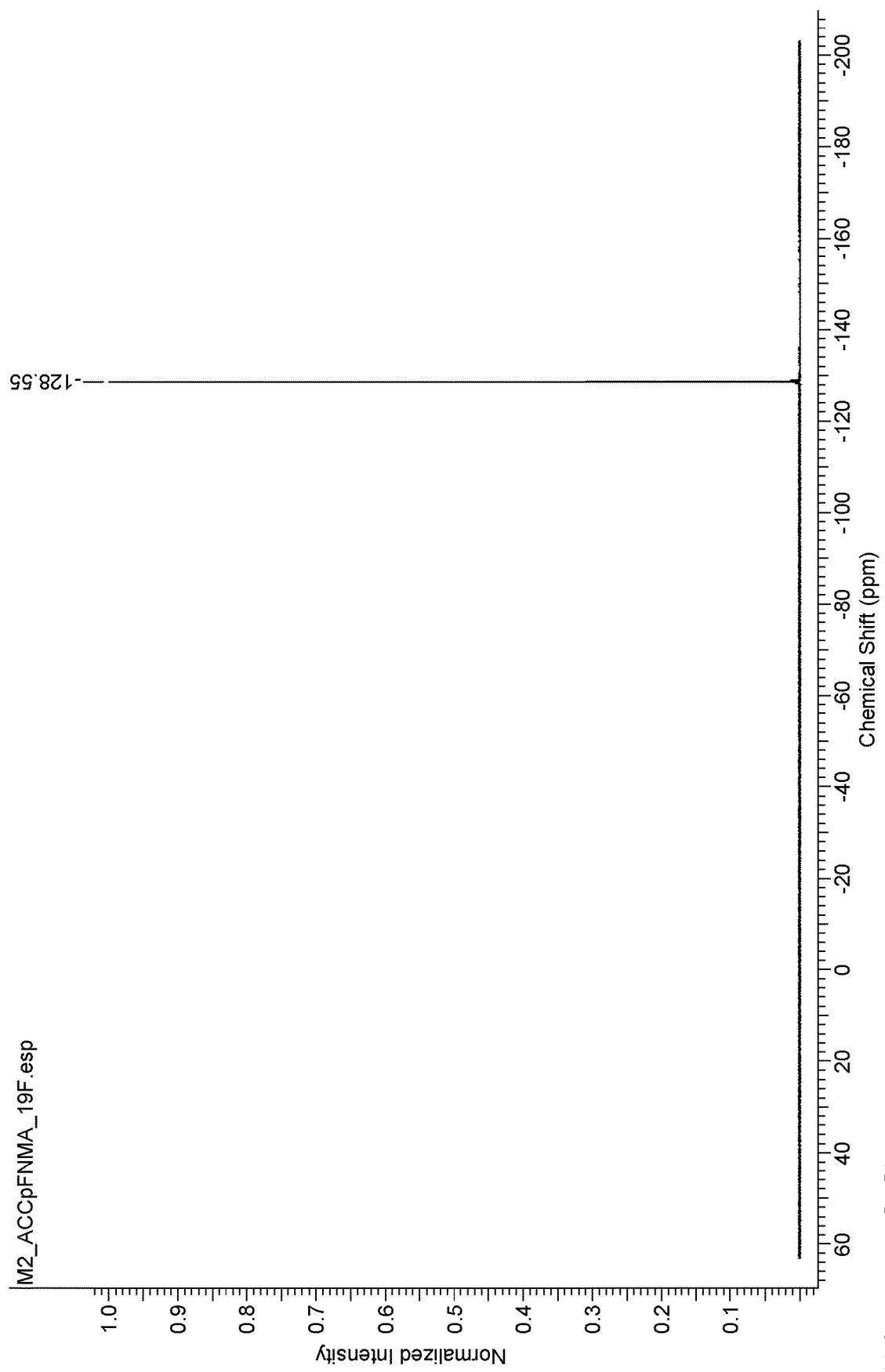
FIG. 8c is a $^{19}$F-NMR spectrum (282 MHz) of amine-functionalized cycloalkene "M2" of the present disclosure in CDCl$_3$ at 293 K.

(Z)—N-(cyclooct-4-en-1-ylmethyl)-4-fluoroaniline (amine-functionalized cycloalkene "M2"). Prepared as per M1 using 4-fluoro-N-methylaniline as the amine substrate to afford 1.53 g of pale-yellow oil (81.7%). $^1$H NMR (300 MHz, CDCl$_3$, FIG. 8a): δ 6.90 (t, 2H, 2×ArH), δ 6.72 (m, 2H, 2×ArH), δ 5.69 (m, 2H, 2×RHC=CHR), δ 3.50 (br s, 1H, NH), δ 2.91 (m, 2H, CH$_2$), δ 2.38 (m, 1H, CH), δ 2.17 (m, 3H, CH$_2$), δ 1.79-1.19 (m, 7H, CH$_2$) $^{13}$C{1H} NMR (75 MHz, CDCl$_3$, FIG. 8b): δ 157.2 (C), δ 154.1 (CH), δ 145.0 (CH), δ 130.1 (CH), δ 115.4 (CH), δ 113.5 (CH), δ 52.4 (CH$_2$), δ 37.7 (CH$_2$), δ 33.4 (CH$_2$), δ 31.2 (CH$_2$), δ 28.2 (CH), δ 25.9 (CH), δ 24.8 (CH) $^{19}$F{1H} NMR (282 MHz, CDCl$_3$, FIG. 8c): δ −128.6 IR (neat oil, cm$^{-1}$, int): 3428br, 3010w, 2909m, 2856sh, 1615w, 1513s, 1470sh, 1320w, 1221s, 814s, 720m HRMS-EI (m/z) Calcd: 233.15798; found: 233.15817.

Figure 9A:
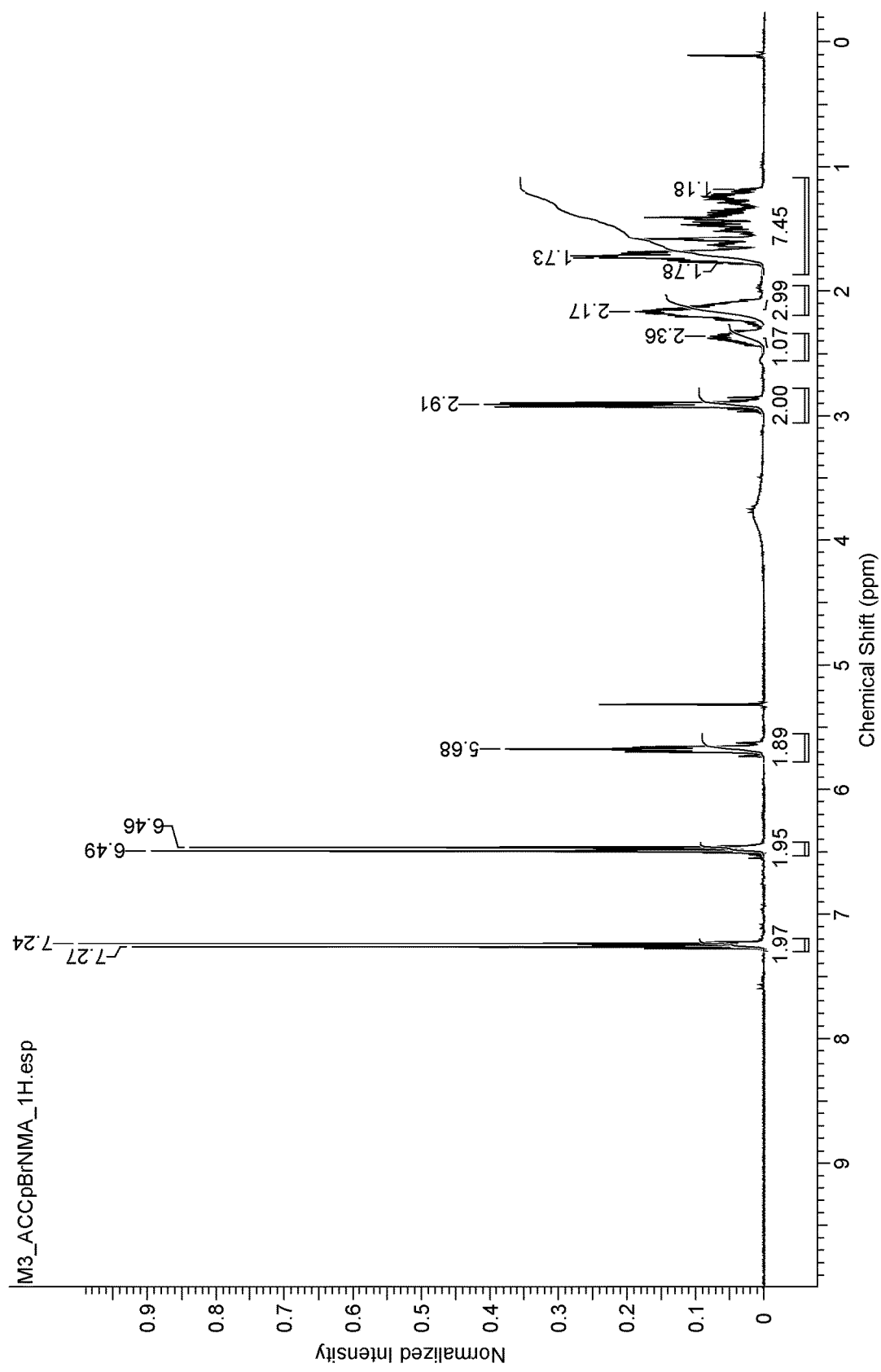
FIG. 9a is a $^1$H-NMR spectrum (300 MHz) of amine-functionalized cycloalkene "M3" of the present disclosure in CDCl$_3$ at 293 K.
Figure 9B:
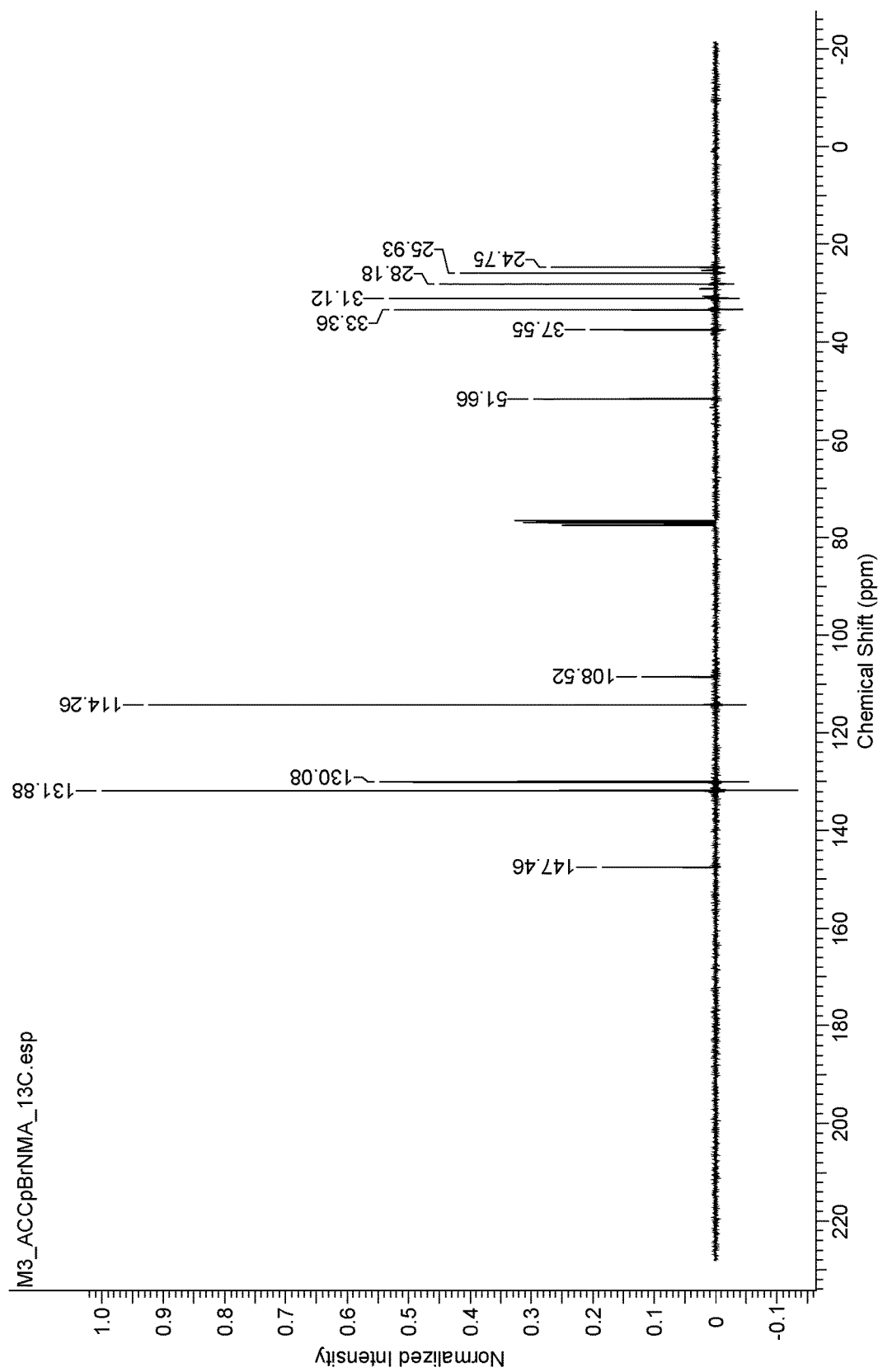
FIG. 9b is a $^{13}$C-NMR spectrum (75 MHz) of amine-functionalized cycloalkene "M3" of the present disclosure in CDCl$_3$ at 293 K.

(Z)—N-(cyclooct-4-en-1-ylmethyl)-4-bromoaniline (amine-functionalized cycloalkene "M3"). Prepared as per M1 using 4-bromo-N-methyl aniline as the amine substrate to afford 1.29 g of pale-yellow oil (81.3%). $^1$H NMR (300 MHz, CDCl$_3$, FIG. 9a): δ 7.25 (d, $^3J_{AB}$=8.77 Hz, 2H, 2×ArH), δ 6.48 (d, $^3J_{AB}$=8.77 Hz, 2H, 2×ArH), δ 5.68 (m, 2H, 2×RHC=CHR), δ 3.78 (br s, 1H, NH), δ 2.91 (m, 2H, CH$_2$), δ 2.36 (m, 1H, CH), δ 2.17 (m, 3H, CH$_2$), δ 1.78-1.18 (m, 7H, CH$_2$) $^{13}$C{1H} NMR (75 MHz, CDCl$_3$, FIG. 9b): δ 147.5 (C), δ 131.9 (CH), δ 130.1 (CH), δ 114.3 (CH), δ 108.5 (CH), δ 51.7 (CH$_2$), δ 37.6 (CH$_2$), δ 33.4 (CH$_2$), δ 31.1 (CH$_2$), δ 28.2 (CH), δ 26.0 (CH), δ 24.8 (CH)) IR (neat oil, cm$^{-1}$, int): 3422br, 3015w, 2922s, 2854sh, 1593s, 1497s, 1313m, 1249m, 1175w, 1073w, 999w, 808s, 723m HRMS-ESI (m/z) Calcd: 293.07791; found: 293.07770.

Figure 10A:
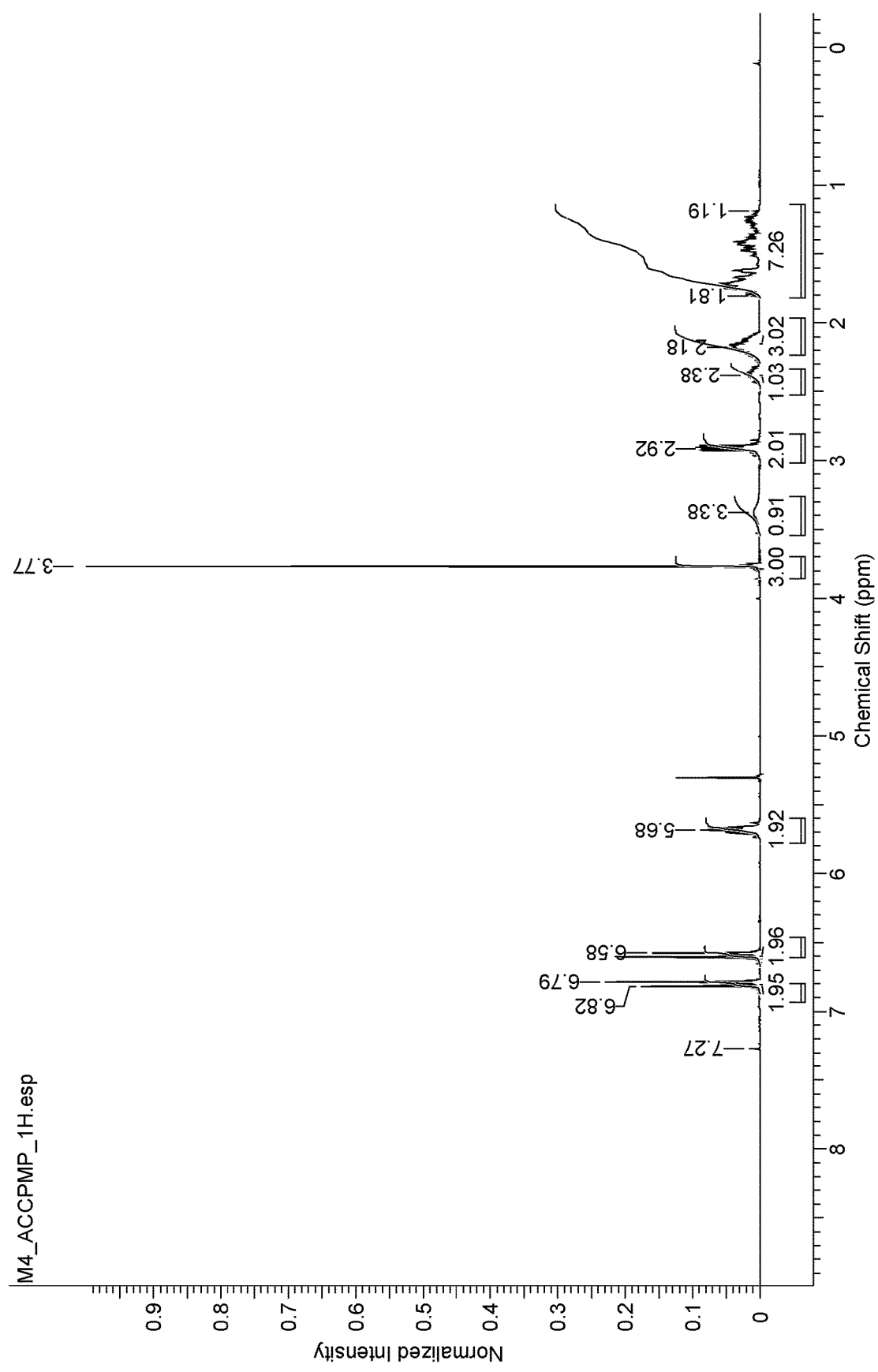
FIG. 10a is a $^1$H-NMR spectrum (300 MHz) of amine-functionalized cycloalkene "M4" of the present disclosure in CDCl$_3$ at 293 K.
Figure 10B:
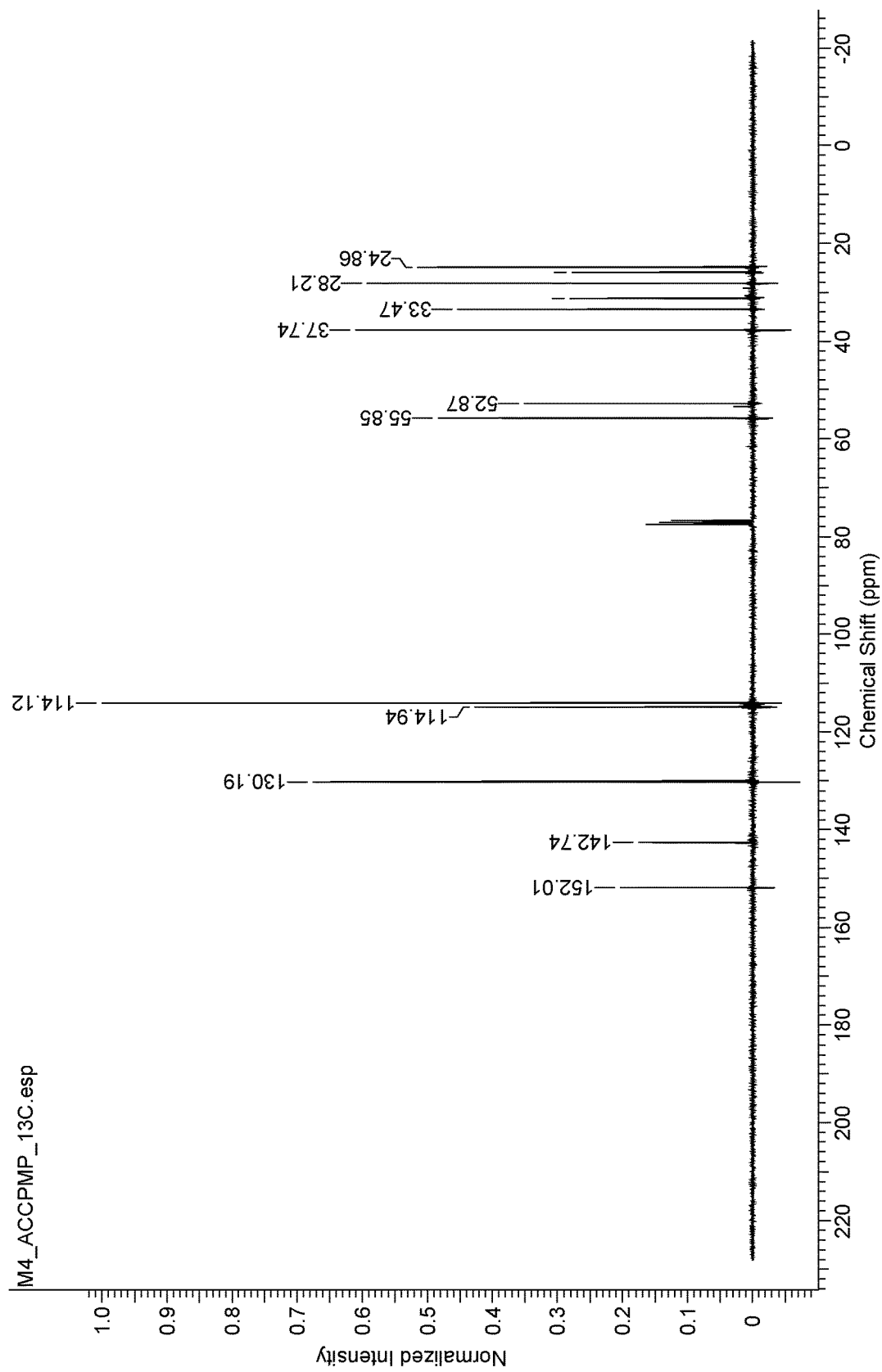
FIG. 10b is a $^{13}$C-NMR spectrum (75 MHz) of amine-functionalized cycloalkene "M4" of the present disclosure in CDCl$_3$ at 293 K.

(Z)—N-(cyclooct-4-en-1-ylmethyl)-4-methoxyaniline (amine-functionalized cycloalkene "M4"). Prepared as per M1 using 4-methoxy N-methyl aniline as the amine substrate to afford 1.52 g of yellow oil (85.0%). $^1$H NMR (300 MHz, CDCl$_3$, FIG. 10a): δ 6.81 (d, $^3J_{AB}$=9.24 Hz, 2H, 2×ArH), δ 6.60 (d, $^3J_{AB}$=8.79 Hz, 2H, 2×ArH), δ 5.68 (m, 2H, 2×RHC=CHR), δ 3.77 (s, 3H, OCH$_3$), δ 3.38 (br s, 1H, NH), δ 2.91 (m, 2H, CH$_2$), δ 2.38 (m, 1H, CH), δ 2.18 (m, 3H, CH$_2$), δ 1.81-1.19 (m, 7H, CH$_2$) $^{13}$C{1H}NMR (75 MHz, CDCl$_3$, FIG. 10b): δ 152.0 (C), δ 142.7 (CH), δ 130.2 (CH), δ 115.0 (CH), δ 114.1 (CH), δ 55.9 (CH$_3$), 52.9 (CH$_2$) δ 37.7 (CH$_2$), δ 33.5 (CH$_2$), δ 31.2 (CH$_2$), δ 28.2 (CH), δ 26.0 (CH), δ 24.9 (CH). IR (neat oil, cm$^{-1}$): 3415br, 3014w, 2919s, 2854sh, 1620w, 1506s, 1463m, 1228s, 1125w, 1035m, 818s, 724w HRMS-EI (m/z) Calcd: 245.17796; found: 245.17794.

(Z)—N-(cyclooct-4-en-1-ylmethyl)-4-(methylthio)aniline (amine-functionalized cycloalkene "M5"). Prepared as per M1 using N-methyl-4-(methylthio)aniline (2.5 g) as the amine substrate to afford 1.52 g of yellow oil (71%) $^1$H NMR (300 MHz, CDCl$_3$): δ 7.22 (d of d, $^3$J=8.7 Hz, $^3$J=2.5 Hz, 2H, 2×ArH), δ 6.54 (t, $^3$J=8.7 Hz, 1H, ArH), δ 5.67 (m, 2H, 2×RHC=CHR), δ 3.88 (br s, 1H, NH), δ 2.93 (m, 2H, CH$_2$), δ 2.42 (s, 3H, CH$_3$), δ 2.38 (m, 1H, CH), δ 2.16 (m, 3H), δ 1.77-1.19 (m, 7H) $^{13}$C{1H} NMR (75 MHz, CDCl$_3$): δ 146.9 (C), δ 131.5 (CH), δ 130.1 (CH), δ 124.2 (C), δ 113.6 (CH), δ 51.9 (CH$_2$), δ 37.5 (CH$_2$), δ 33.3 (CH$_2$), δ 31.1 (CH$_2$), δ 28.1 (CH), δ 25.9 (CH), δ 24.7 (CH), δ 19.2 (CH$_3$) IR (neat oil, cm$^{-1}$, int): 3417br, 3013w, 2915vs, 2850s, 1598vs, 1500vs, 1466m, 1437w, 1400w, 1367w, 1312m, 1289m, 1248m, 1201w, 1181w, 1128w, 1103w, 966w, 884w, 812m, 756w, 722m HRMS-ESI (m/z) Calcd: 262.1629; found: 262.1637.

(Z)—N-(cyclooct-4-en-1-ylmethyl)-cyclohexanamine (amine-functionalized cycloalkene "M6"). Prepared as per M1 using N-methylcyclohexylamine (0.45 g) as the amine substrate to afford 0.6 g of yellow oil (53%) $^1$H NMR (300 MHz, CDCl$_3$): δ 5.64 (m, 2H, 2×RHC=CHR), δ 2.44 (m, 3H, N—CH$_2$, N—CH), δ 2.34 (m, 1H, CH), δ 2.12 (m, 3H), δ 1.88-1.00 (m, 18H) $^{13}$C{1H} NMR (75 MHz, CDCl$_3$): δ 130.2 (CH), δ 129.9 (CH), δ 56.9 (CH), δ 54.9 (CH$_2$), δ 38.1 (CH), δ 33.7 (CH$_2$), δ 33.6 (CH$_2$), δ 31.6 (CH$_2$), δ 28.2 (CH), δ 26.2 (CH$_2$), δ 25.9 (CH$_2$), δ 25.1 (CH$_2$), δ 24.9 (CH$_2$) IR (neat oil, cm$^{-1}$, int): 3014w, 2923vs, 2851s, 1651m, 1612w, 1570w, 1463s, 1449s, 1374w, 1348w, 1258w, 1228w, 1131m, 1028w, 989w, 972w, 941 w, 886m, 844w, 775m, 754m, 721vs HRMS-ESI (m/z) Calcd: 222.2222; found: 222.2228.

Table 1 provides a summary of the exemplary amine-functionalized cycloalkenes synthesized.

TABLE 1

Overview of synthesized amine-functionalized cycloalkenes.

| Compound ID | IUPAC Name | Chemical Structure |
|---|---|---|
| M1 | (Z)-N-(cyclooct-4-en-1-ylmethyl)aniline | 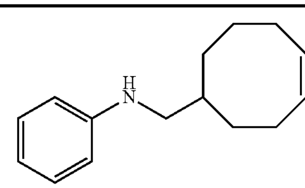 |

TABLE 1-continued

Overview of synthesized amine-functionalized cycloalkenes.

| Compound ID | IUPAC Name | Chemical Structure |
| --- | --- | --- |
| M2 | (Z)-N-(cyclooct-4-en-1-ylmethyl)-4-fluoroaniline | 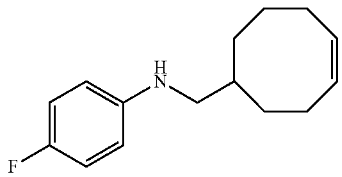 [SMILES: Fc1ccc(NCC2CC/C=C\CCC2)cc1] |
| M3 | (Z)-N-(cyclooct-4-en-1-ylmethyl)-4-bromoaniline | 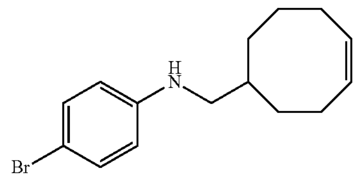 [SMILES: Brc1ccc(NCC2CC/C=C\CCC2)cc1] |
| M4 | (Z)-N-(cyclooct-4-en-1-ylmethyl)-4-methoxyaniline | 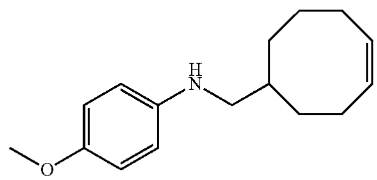 [SMILES: COc1ccc(NCC2CC/C=C\CCC2)cc1] |
| M5 | (Z)-N-(cyclooct-4-en-1-ylmethyl)-4-(methylthio)aniline | 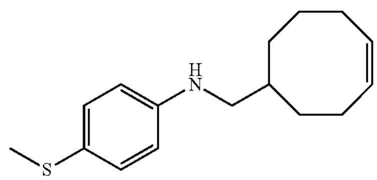 [SMILES: CSc1ccc(NCC2CC/C=C\CCC2)cc1] |
| M6 | (Z)-N-(cyclooct-4-en-1-ylmethyl)-cyclohexanamine | 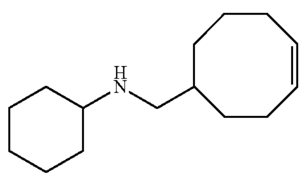 [SMILES: C1=C\CCC(CNC2CCCCC2)CCC/1] |

These monomers bearing pendant, secondary aryl amines were amenable to ROMP using Grubbs Catalyst 2nd Generation to obtain linear polymers.

4.3 Polymerization

Figure 3:
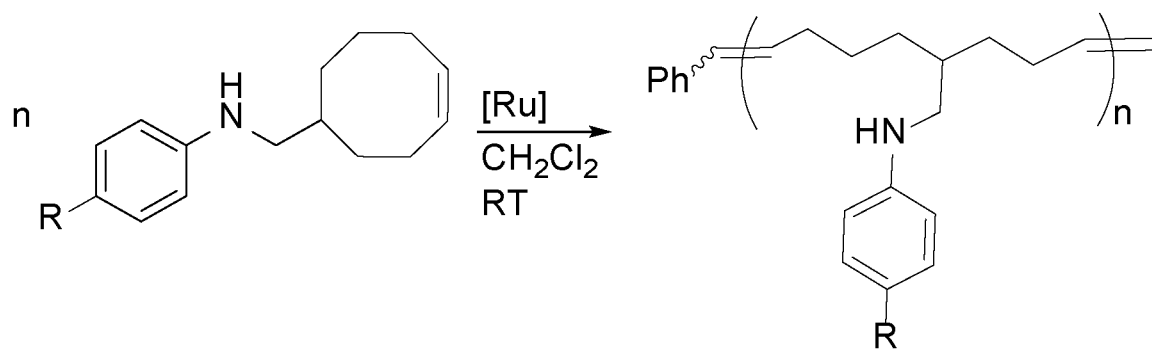
FIG. 3 is a diagram depicting a ring-opening metathesis polymerization (ROMP) to obtain amine-containing polycyclooctenes according to an embodiment of the disclosure

FIG. 3 depicts the general scheme for polymerization of hydroaminoalkylated cycloalkene monomers according to the present disclosure. Polymerization of amine-functionalized cycloalkene monomers M1, M2, M3, and M4 was completed using ring-opening metathesis polymerization (ROMP) using Grubbs Catalyst™ 2nd Generation. Generally, a solution of catalyst in $CH_2Cl_2$ was added to a solution of the monomer in $CH_2Cl_2$ with stirring. Reactions were performed on gram-scale quantities at room temperature to access high conversion of monomer. Reactions were allowed to proceed for a minimum 1 hr to ensure full conversion. Upon completion of the reaction the solution slowly goes light amber-yellow/green from the originally dark amber solution. Reactions were quenched via exposure to ambient atmosphere and drop-wise addition of an excess of ethyl vinyl ether (min. of 2 drops per mg of [Ru] catalyst), and left to stir for a minimum of thirty minutes, after which the solution slowly changes color to dark amber/black. The polymer was precipitated as a gum-like off-white solid via drop-wise addition to a stirring vortex of methanol (−35° C., and a minimum of 1 mL per mg polymer), which was notably different in physical appearance to that of non-functionalized poly(cyclooctene), which precipitated as a white, flocculent solid. Isolation was completed by decanting the supernatant and overnight drying of the collected material under high vacuum. All characterization was thereafter completed with the exception of GPC analysis, for which further purification was completed via two additional precipitations (using addition of a $CH_2Cl_2$ solution of the polymer into a large excess of methanol) followed by drying in a vacuum oven.

Figure 11A:
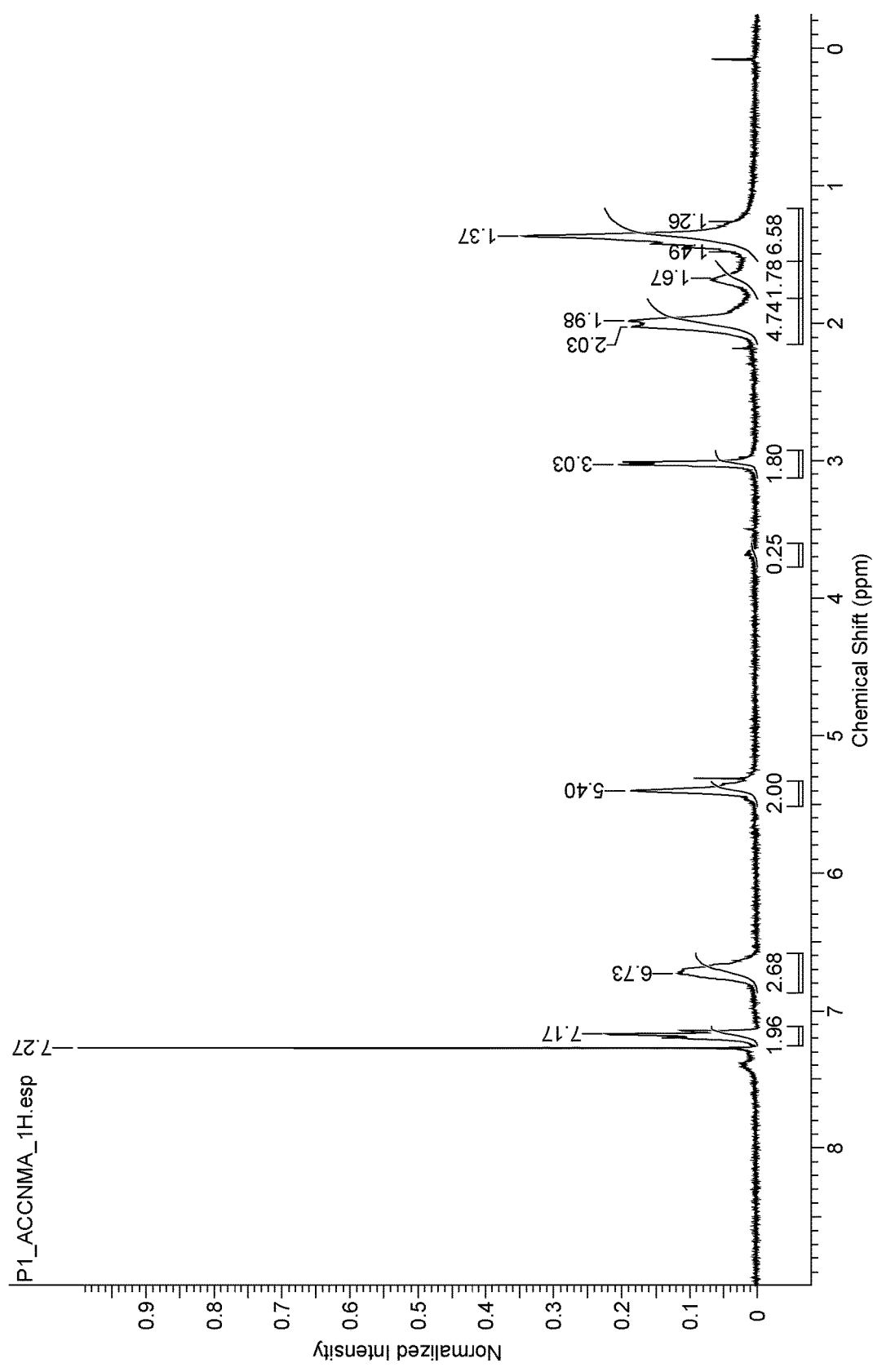
FIG. 11a is a $^1$H-NMR spectrum (300 MHz) of polymer "P1" of the present disclosure in CDCl$_3$ at 293 K.
Figure 11B:
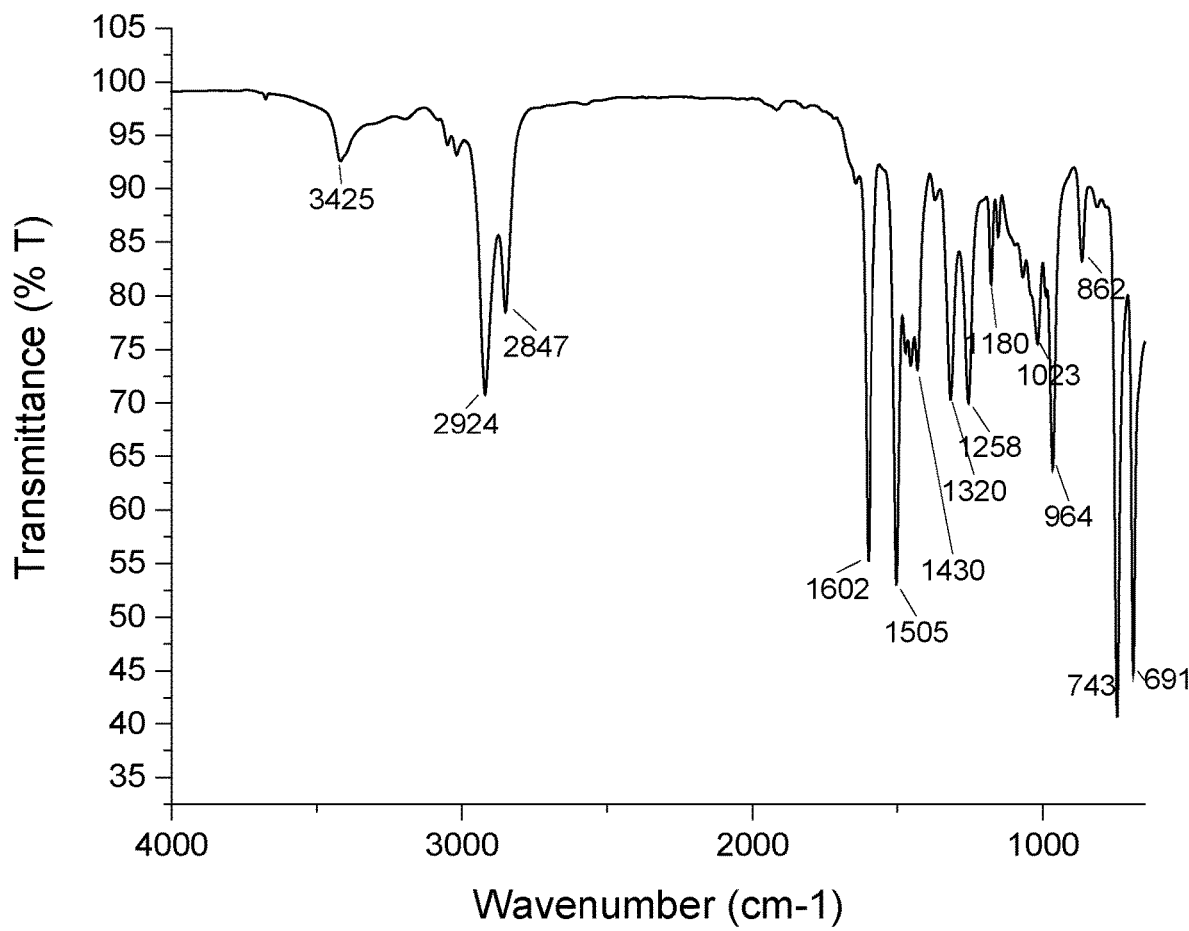
FIG. 11b is a solid state spectrum of polymer "P1" of the present disclosure in CDCl$_3$ at 293 K.

Poly(N-(cyclooct-4-en-1-ylmethyl)aniline) (polymer "P1"). Prepared as above to afford 0.602 g of an off-white gun-like solid (81%). $^1$H NMR (300 MHz, $CDCl_3$, FIG. 11a): δ 7.17 (m, 2H, 2×ArH), δ 6.73 (br s, 3H, 3×ArH), δ 5.40 (m, 2H, 2×RHC=CHR), δ 3.03 (d, 2H, $CH_2$), δ 2.00 (m, 4H, $CH_2$), δ 1.68 (br s, 1H, CH), δ 1.49-1.26 (m, 6H, $CH_2$) IR (neat oil, $cm^{-1}$, int, FIG. 11b): 3425br, 2924s, 2847sh, 1602 s, 1505s, 1430sh, 1320m, 1258m, 1180w, 1023w, 964m, 862w, 743s, 691s.

Figure 12A:
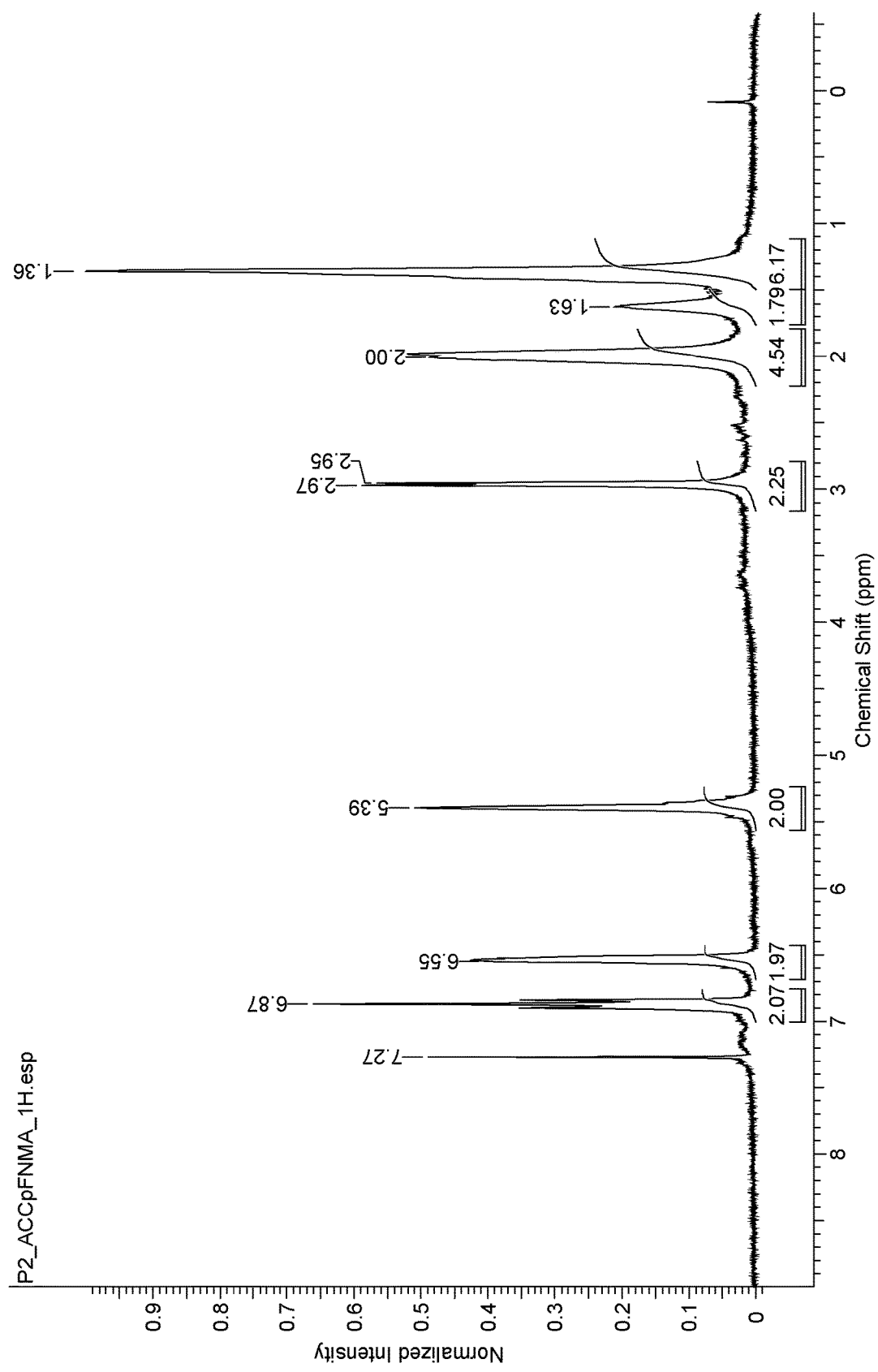
FIG. 12a is a $^1$H-NMR spectrum (300 MHz) of polymer "P2" of the present disclosure in CDCl$_3$ at 293 K.
Figure 12B:
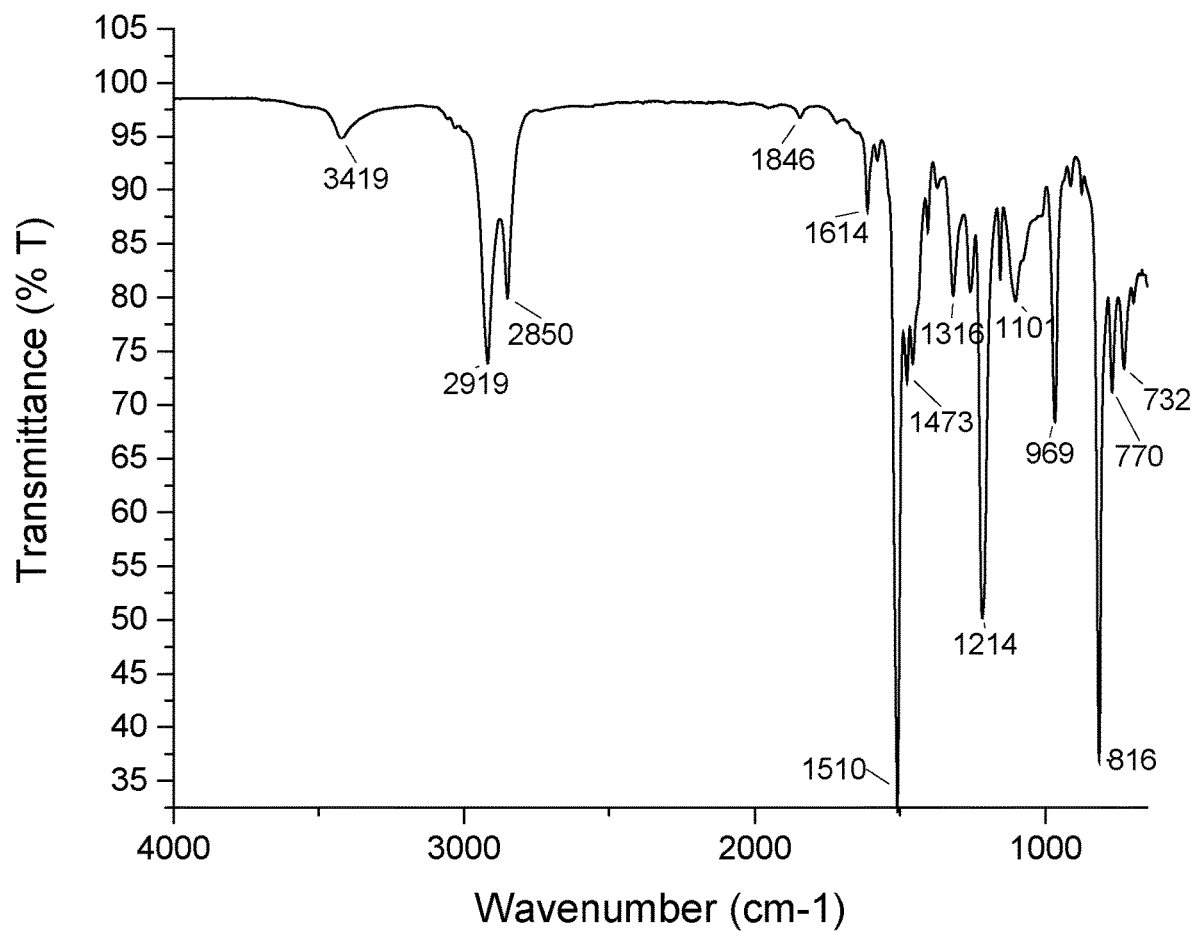
FIG. 12b is a solid state spectrum of polymer "P2" of the present disclosure in CDCl$_3$ at 293 K.
Figure 13A:
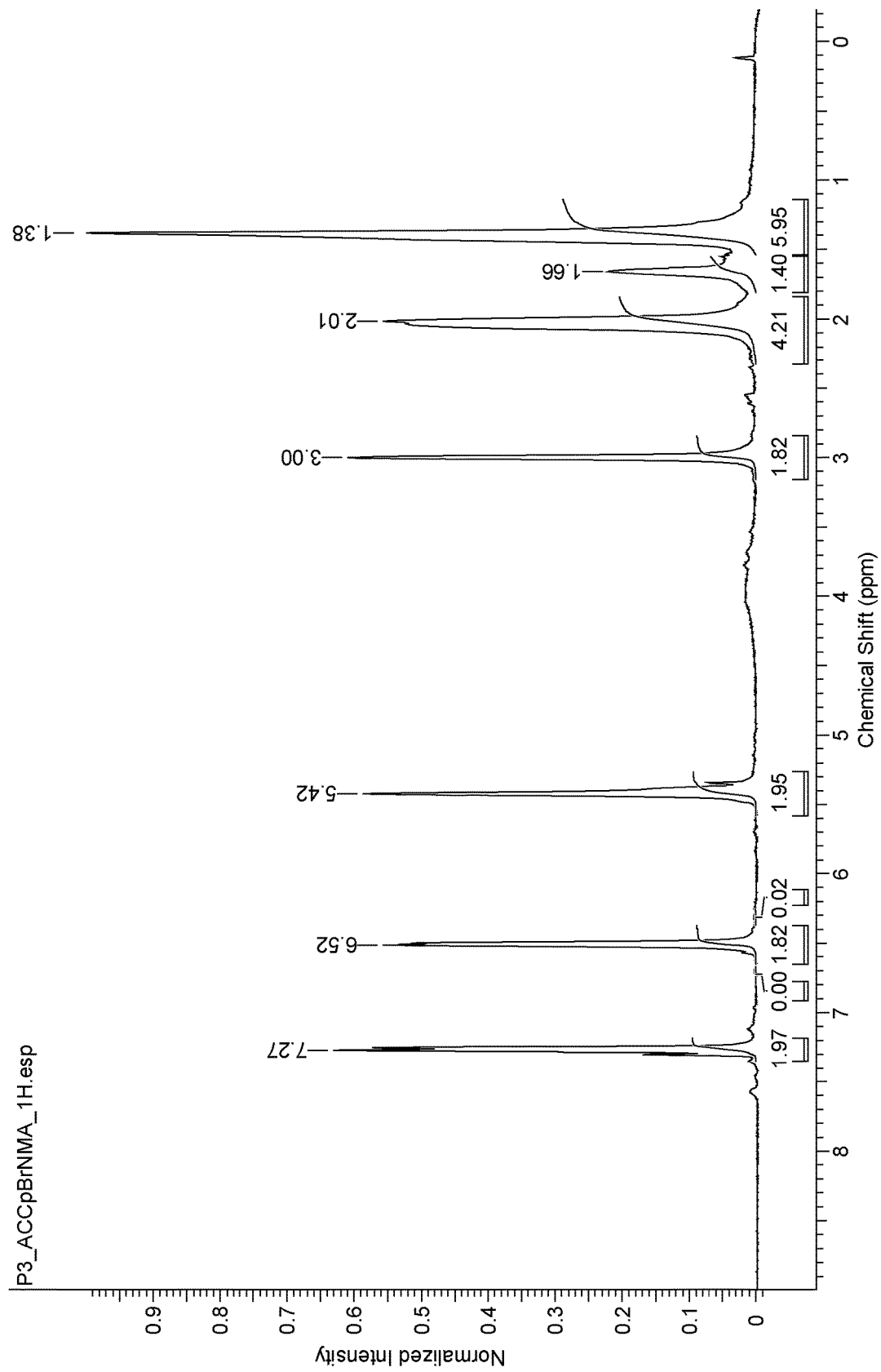
FIG. 13a is a $^1$H-NMR spectrum (300 MHz) of polymer "P3" of the present disclosure in CDCl$_3$ at 293 K.
Figure 13B:
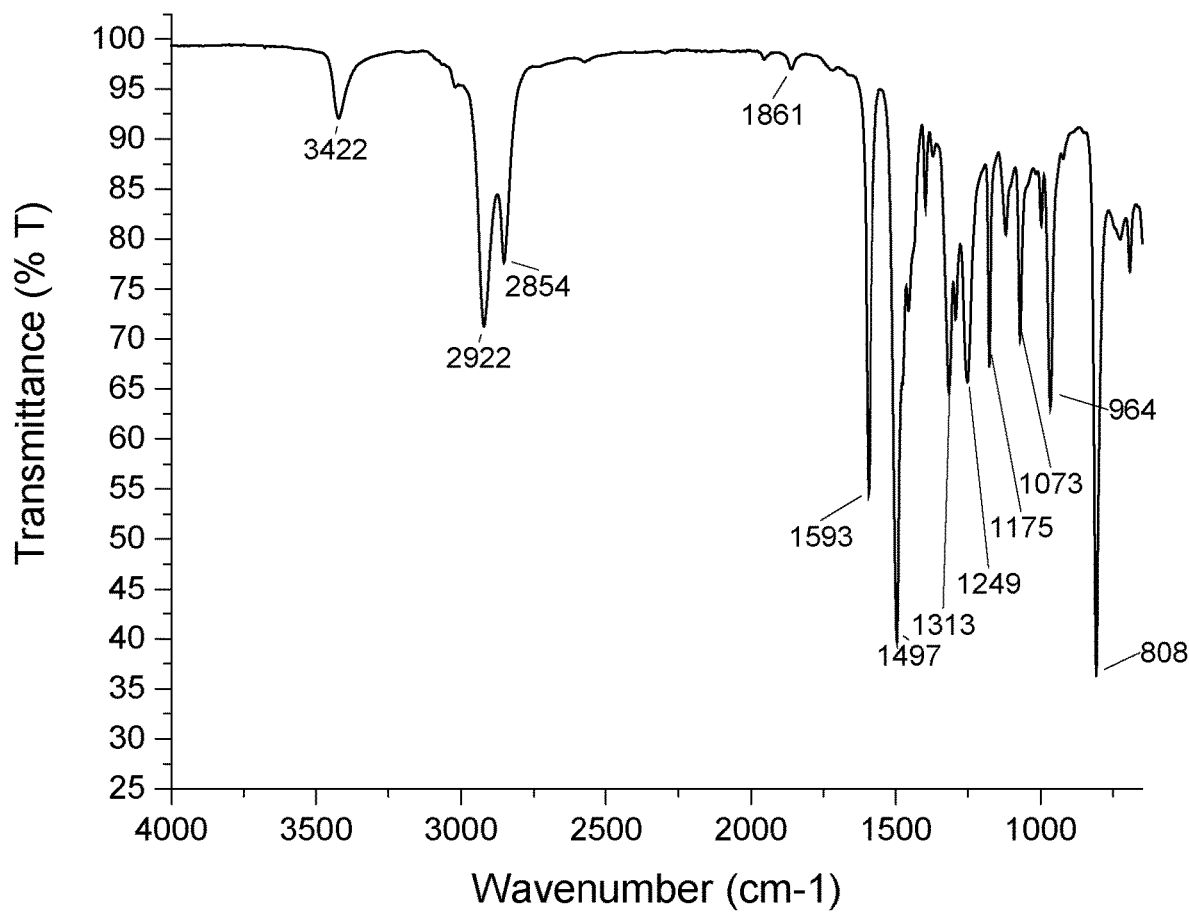
FIG. 13b is a solid state spectrum of polymer "P3" of the present disclosure in CDCl$_3$ at 293 K.

Poly(N-(cyclooct-4-en-1-ylmethyl)-4-fluoroaniline) (polymer "P2"). Prepared as above to afford 0.690 g of gummy, off-white solid (88%). %). $^{1}$H NMR (300 MHz, CDCl$_3$, FIG. 12a): δ 6.87 (m, 2H, 2×ArH), δ 6.55 (br s, 2H, 2×ArH), δ 5.39 (m, 2H, 2×RHC=CHR), δ 2.97 (d, 2H, CH$_2$), δ 2.00 (m, 4H, CH$_2$), δ 1.63 (br s, 1H, CH), δ 1.36 (br s, 6H, CH$_2$)$^{19}$F{1H} NMR (282 MHz, CDCl$_3$): δ −127.7 IR (neat oil, cm$^{-1}$, int, FIG. 12b): 3419br, 2919m, 2850sh, 1614w, 1510s, 1473sh, 1316w, 1214s, 1101w, 816s Poly(N-(cyclooct-4-en-1-ylmethyl)-4-bromoaniline) (polymer "P3"). Prepared as above to afford 0.592 g of gummy, off-white solid (94%). $^{1}$H NMR (400 MHz, CDCl$_3$, FIG. 13a): δ 7.27 (m, 2H, 2×ArH), δ 6.52 (br s, 2H, 2×ArH), δ 5.42 (m, 2H, 2×RHC=CHR), δ 3.00 (d, 2H, CH$_2$), δ 2.01 (br s, 4H, CH$_2$), δ 1.66 (br s, 1H, CH$_2$), δ 1.38 (br s, 6H, CH$_2$) IR (neat oil, cm$^{-1}$, int, FIG. 13b): 3422br, 2922s, 2854sh, 1593s, 1497s, 1313m, 1249m, 1175m, 1073m, 964m, 808s.

Figure 14A:
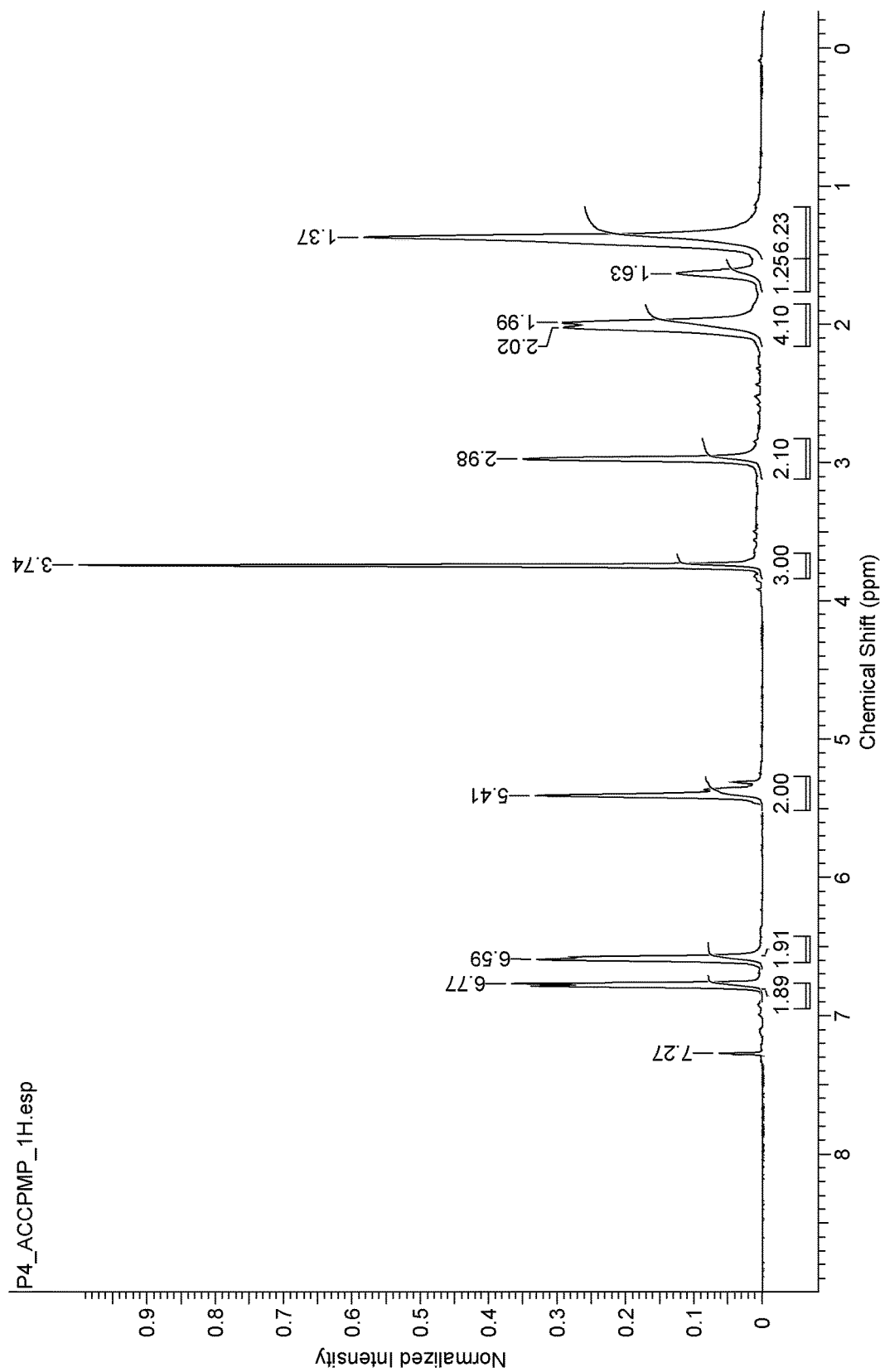
FIG. 14a is a $^1$H-NMR spectrum (300 MHz) of polymer "P4" of the present disclosure in CDCl$_3$ at 293 K.
Figure 14B:
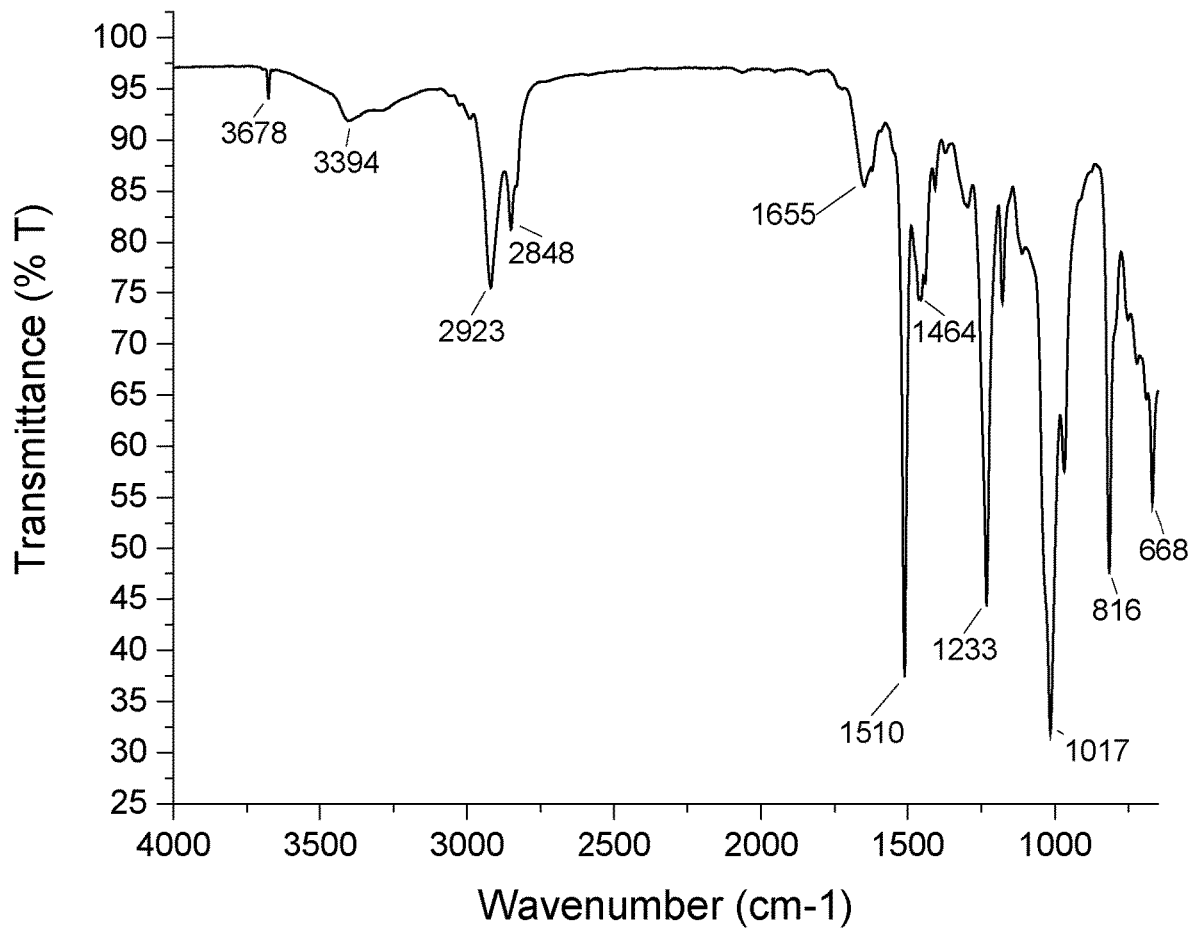
FIG. 14b is a solid state spectrum of polymer "P4" of the present disclosure in CDCl$_3$ at 293 K.

Poly(N-(cyclooct-4-en-1-ylmethyl)-4-methoxyaniline (polymer "P4"). Prepared as above to afford 0.541 g of gummy, off-white solid (88%). $^{1}$H NMR (400 MHz, CDCl$_3$, FIG. 14a): δ 6.78 (d, 2H, 2×ArH), δ 6.59 (br s, 2H, 2×ArH), δ 5.39 (m, 2H, 2×RHC=CHR), δ 3.74 (s, 3H, OCH$_3$), δ 2.98 (d, 2H, CH$_2$), δ 2.01 (br s, 4H, CH$_2$), δ 1.63 (br s, 1H, CH$_2$), δ 1.37 (br s, 6H, CH$_2$) IR (neat oil, cm$^{-1}$, int, FIG. 14b): 3394br, 2923s, 2848sh, 1655br, 1510s, 1464sh, 1233s, 1017s, 816s, 668m.

Poly(N-(oct-4-en-1-ylmethyl)-4-(methylthio)aniline (polymer "P5"). Prepared as above to afford a dark purple solid (70%). $^{1}$H NMR (300 MHz, CDCl$_3$): δ 7.22 (m, 2H, 2×ArH), δ 6.54 (m, 2H, 2×ArH), δ 5.40 (br s, 2H, 2×RHC=CHR), δ 3.69 (br s, 1H, NH), δ 2.99 (m, 2H, CH$_2$), δ 2.42 (m, 3H, CH$_3$), δ 1.99 (m, 4H), δ 1.77-1.19 (m, 7H) IR (neat oil, cm$^{-1}$, int): 3414br, 2917s, 2852m, 1597vs, 1500vs, 1474m, 1455m, 1435w, 1401w, 1312m, 1289m, 1250m, 1181m, 1101w, 966s, 812s, 735w.

Poly(N-(oct-4-en-1-ylmethyl)-cyclohexanamine (polymer "P6"). Prepared as above to afford a dark orange solid (42%). $^{1}$H NMR (300 MHz, C$_7$D$_8$): δ 5.53 (br s, 2H, 2×RHC=CHR), δ 2.55 (br s, 2H, CH$_2$), δ 2.37 (m, 1H, CH), δ 2.11 (br s, 4H, CH$_2$), δ 1.86-1.07 (m, 17H, CH, CH$_2$), δ 0.52 (br s, 1H, NH) IR (neat oil, cm$^{-1}$, int): 2921vs, 2851s, 1670w, 1449s, 1365w, 1347w, 1259w, 1241w, 1130m, 966vs, 922w, 888m, 845m, 845w, 786w, 723s.

Polymers P1 to P6 were obtained in high yield (>80%) regardless of the pendant secondary amine substituent. Analysis of chemical shifts in $^{1}$H NMR spectra showed broadened signals consistent with polymer formation. For example, for polymer P2 one major peak was observed in the $^{19}$F NMR spectrum; a broad singlet at δ −127.7 ppm, while for polymer P4 the methoxy substituent provided a diagnostic NMR signal, which was observed as a broad singlet (δ 3.74 ppm) in the $^{1}$H NMR spectrum; furthermore this peak integrated in a 3:2 ratio, when compared with the olefinic resonances at δ 5.41 ppm. In the case of M1, a crude reaction mixture from hydroaminoalkylation was found to be amenable to ROMP without purification by column chromatography, however the resulting material could, like P2 and P4, only be characterized by NMR and IR spectroscopy.

Table 2 provides a summary of the exemplary polymers synthesized.

TABLE 2

Overview of polymers synthesized.

| Compound ID | IUPAC Name | Chemical Structure |
|---|---|---|
| P1 | Poly(N-(oct-4-en-1-ylmethyl)aniline) | 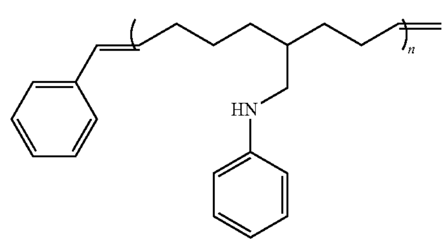 |
| P2 | Poly(N-(oct-4-en-1-ylmethyl)-4-fluoroaniline) | 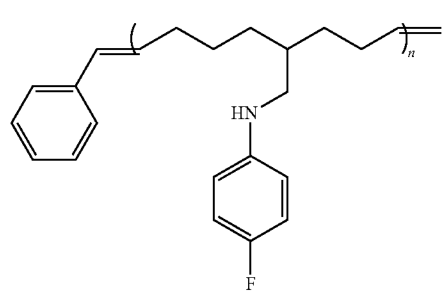 |

TABLE 2-continued

Overview of polymers synthesized.

| Compound ID | IUPAC Name | Chemical Structure |
|---|---|---|
| P3 | Poly(N-(oct-4-en-1-ylmethyl)-4-bromoaniline) | *[structure: polymer backbone with pendant CH2-NH-C6H4-Br group and phenyl-substituted alkene chain end]* |
| P4 | Poly(N-(oct-4-en-1-ylmethyl)-4-methoxyaniline) | *[structure: polymer backbone with pendant CH2-NH-C6H4-OCH3 group]* |
| P5 | Poly(N-(oct-4-en-1-ylmethyl)-4-(methylthio)aniline) | *[structure: polymer backbone with pendant CH2-NH-C6H4-SCH3 group]* |
| P6 | Poly(N-(oct-4-en-1-ylmethyl)-cyclohexanamine) | *[structure: polymer backbone with pendant CH2-NH-cyclohexyl group]* |

4.4 Hydrogenation

Hydrogenative reduction of the polymer backbone of polymer P1 was targeted in order to obtain a saturated polymer analogous to polyethylene. The reduction could be realized using tosyl hydrazine as a hydrogen source that selectively reduced the C=C double bond of polymer P1. Due to the pendant secondary amine, a basic work-up of the polymer was required.

Figure 15A:
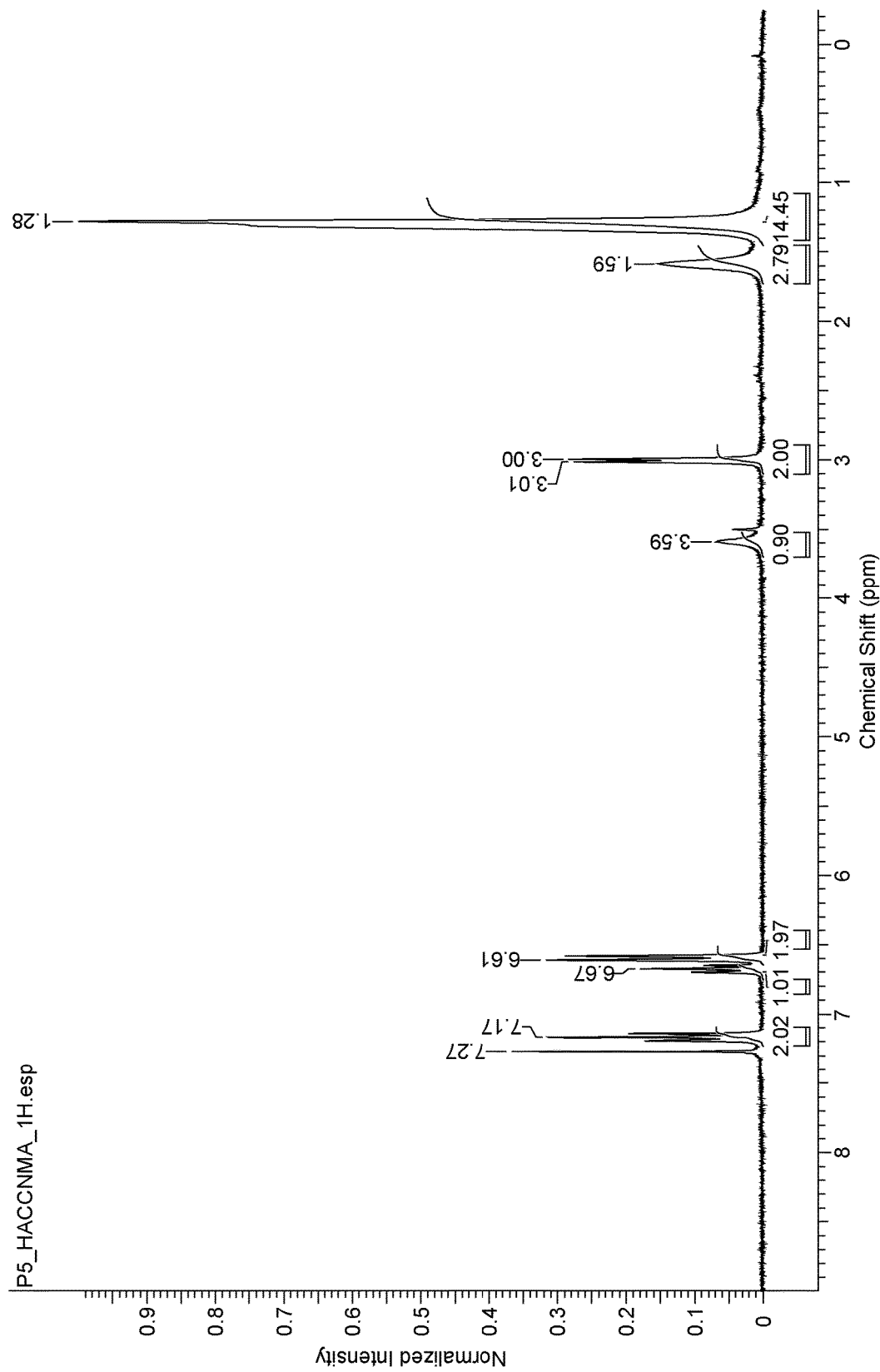
FIG. 15a is a $^1$H-NMR spectrum (300 MHz) of polymer "P1H" of the present disclosure in CDCl$_3$ at 293 K.
Figure 15B:
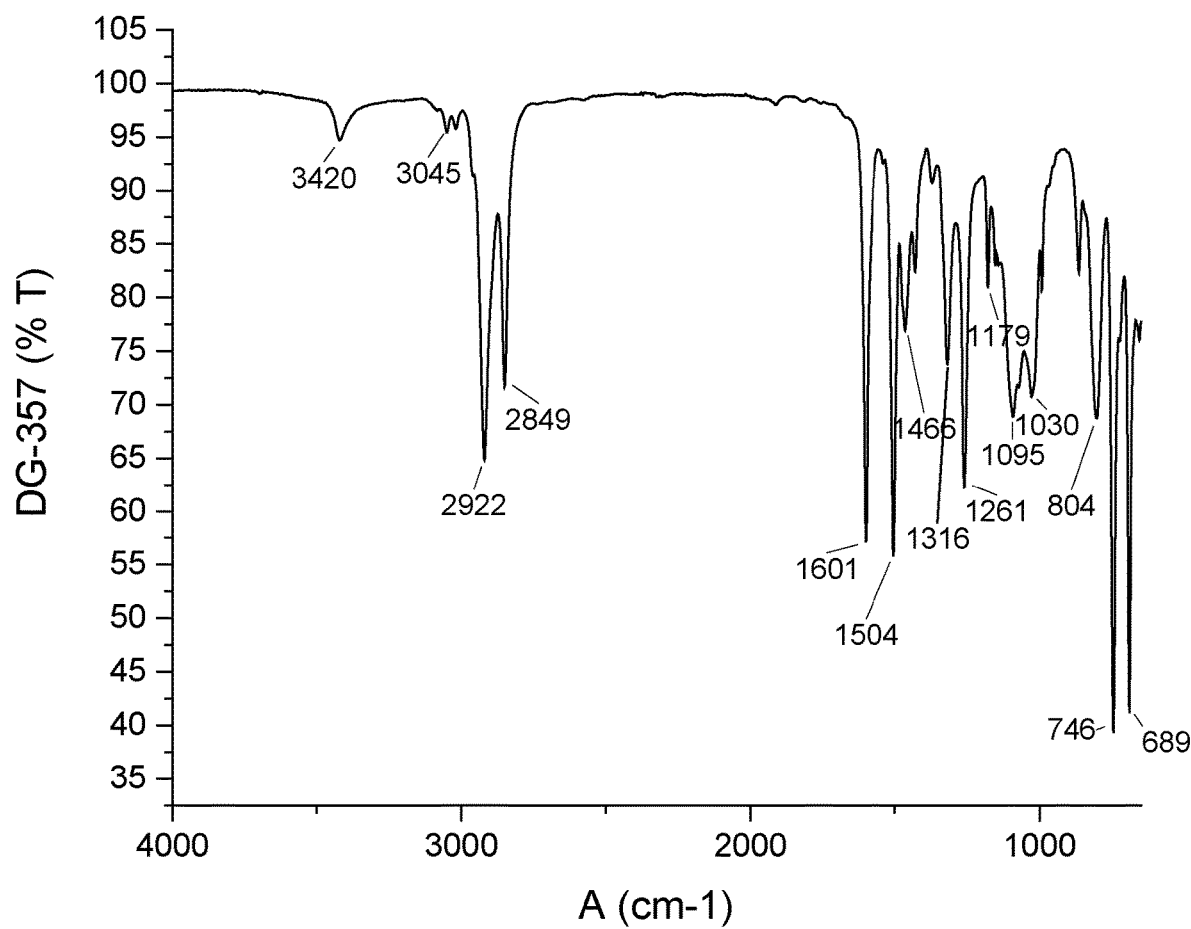
FIG. 15b is a solid state spectrum of polymer "P1H" of the present disclosure in CDCl$_3$ at 293 K.
Figure 16:
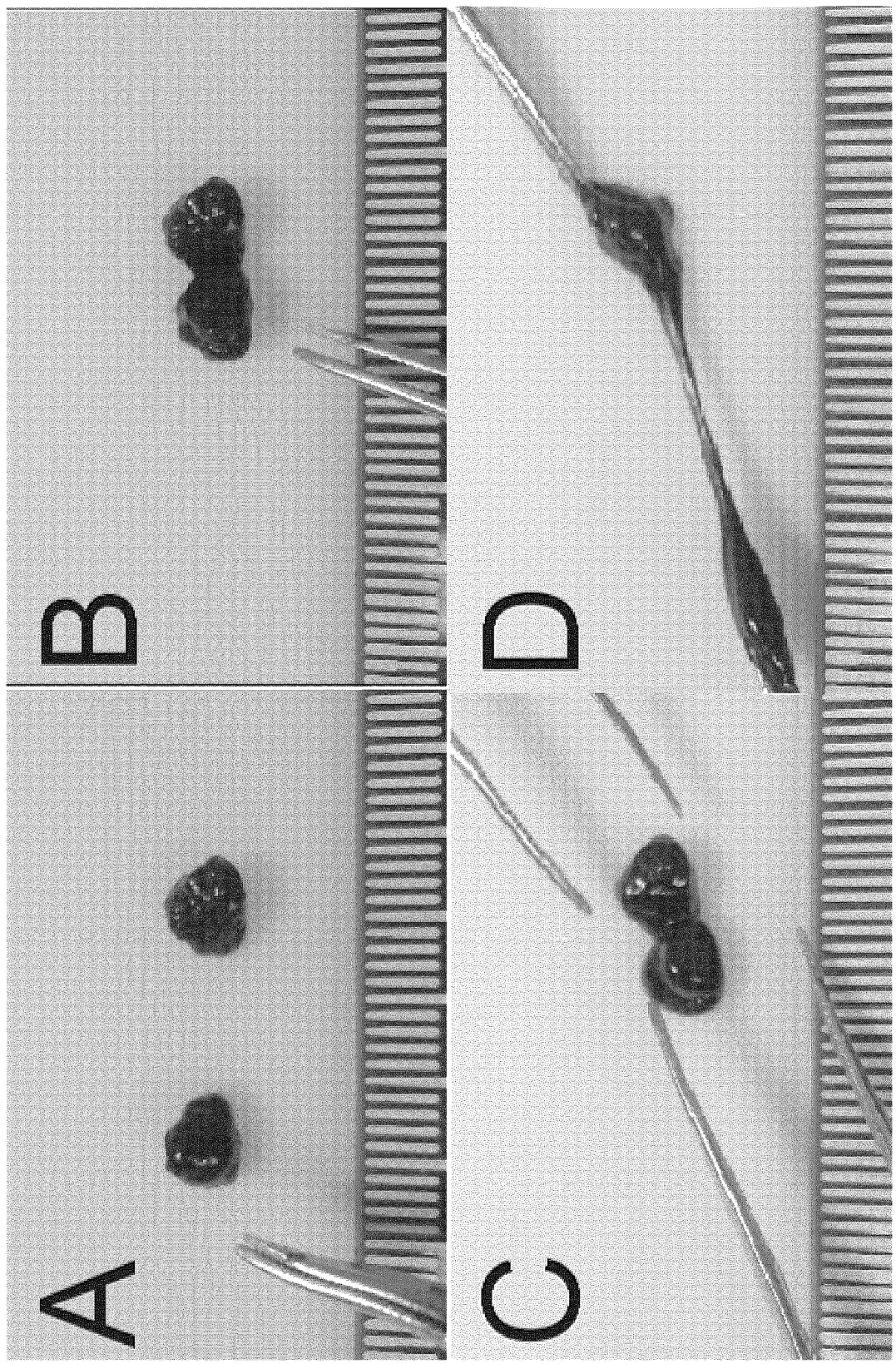
FIG. 16 is photographic images of macroscopic self-healing of polymer P1 spheres: (A) dried spheres on PTFE; (B) spheres brought just into contact; (C) and (D) after 24 hrs under ambient conditions (C), spheres no longer show discrete boundary when pulled apart (D).

Poly(N-(cyclooct-4-an-1-ylmethyl)aniline) (polymer "P1H"). P1 (480 mg, 2 mmol alkene) and p-toluenesulfonyl hydrazide (1.5 g, 8 mmol) in xylene (15 mL), along with a few mgs of 2,4,6-tri-tert-butyl phenol added as a radical sponge, were added to a 100 mL reaction vessel equipped with a Teflon capped-valve and side-arm and a Teflon-coated stir bar. The resulting heterogeneous mixture was filled with $N_2$, freeze-pump-thawed three times, then back-filled with $N_2$. The vessel was sealed and heated to 130° C. in an oil-bath for a minimum of 8 hours. After the duration of the reaction, a pale-yellow, clear solution was obtained. The vessel was opened and the mixture transferred to a separatory funnel, using ethyl acetate (50 mL) to quantitatively transfer. The organic layer was washed three times with 3 M NaOH, then once with brine, then reduced to 3 mL via rotary evaporation under reduced pressure. This residue was then added drop-wise to a large excess of vortexing methanol (−35° C., 250 mL) to afford the product as an off-white, gummy solid. After three excessive precipitations, 0.350 g of material was obtained (73.0%). $^1$H NMR (300 MHz, CDCl$_3$, FIG. 15a): δ 7.17 (m, 2H, 2×ArH), δ 6.69 (t, 1H, ArH), δ 6.63 (d, 2H, ArH), δ 3.01 (d, 2H, CH$_2$), δ 1.61 (br s, 1H, CH), δ 1.28 (m, 14H, CH$_2$) IR (neat oil, cm$^{-1}$, int, FIG. 15b): 3420br, 3045w, 2922s, 2849sh, 1601s, 1504s, 1466sh, 1316m, 1261m, 1095br, 1030br, 804s, 746s, 689s.

Table 3 provides a summary of the exemplary hydrogenated polymers that were synthesized.

TABLE 3

Overview of example compounds.

| Compound ID | IUPAC Name | Chemical Structure |
|---|---|---|
| P1H | Poly(N-(oct-4-an-1-ylmethyl)aniline) | 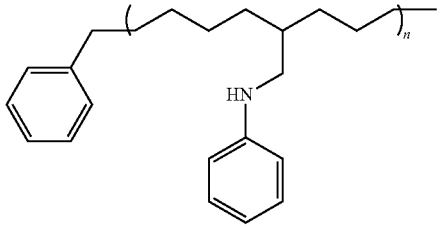 |
| P2H | Poly(N-(oct-4-an-1-ylmethyl)-4-fluoroaniline) | 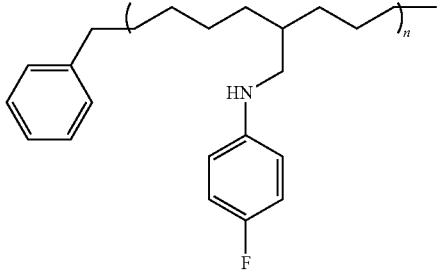 |
| P3H | Poly(N-(oct-4-an-1-ylmethyl)-4-bromoaniline) | 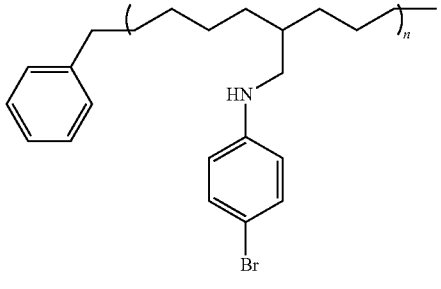 |
| P4H | Poly(N-(oct-4-an-1-ylmethyl)-4-methoxyaniline | 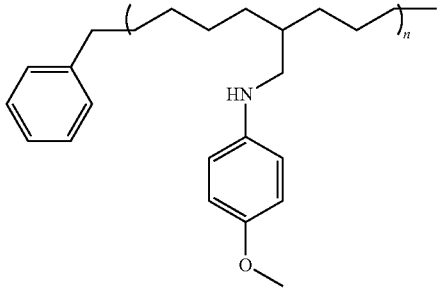 |
| P5H | Poly(N-(oct-4-an-1-ylmethyl)-4-(methylthio)aniline | 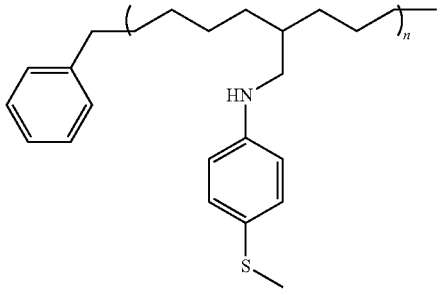 |

TABLE 3-continued

Overview of example compounds.

| Compound ID | IUPAC Name | Chemical Structure |
|---|---|---|
| P6H | Poly(N-(oct-4-an-1-ylmethyl)-cyclohexanamine | (structure shown) |

The secondary aryl amine and its substituents may be varied to tune hydrogen bonding interactions which may result in polymers displaying various physical properties, e.g. a liquid, gel-like, soft, or solid structure Example 2: NMR Polymerization Study The polymerization of M1 was monitored by NMR spectroscopy. To a sealed NMR tube was added the Grubbs initiator, 100 equivalents of M1 and ca. 1 mL deuterated chloroform. After 10 min, approximately 35% of the monomer had been consumed; after 30 minutes the reaction had exceeded 95% completion. In contrast to other amine-functionalized monomers which are incompatible with Grubbs initiators, the rapid conversion of M1 shows that aryl substituted secondary amines are amenable to ROMP. Notably, throughout the polymerization, the signal assigned to the benzylidene Ru=CHPh proton at 19.2 ppm remained present in the spectrum (Figure X), wherein this observation may suggest incomplete initiation of the catalyst and rates of propagation that are greater than rates of catalyst initiation.

To probe whether the chain termination took place upon reaction completion, an aliquot of ca. 25 equivalents of M2 was added long after monomer M1 had been fully consumed (12 hours). Upon addition of M2, rapid polymerization took place and no signals consistent with the internal alkene of M2 was observed after 30 minutes, while the overlapping alkene peaks of P1 and P2 suggest that polymerization is not self-terminating and the addition of a quenching reagent is required to complete the reaction. Furthermore, the $^{19}F$ NMR spectrum showed a single broad singlet consistent with ring-opened M2 polymeric material, corroborating the evidence present in the $^{1}H$ NMR spectrum.

4.4 Molecular Weight and Dispersity

Polymers that possessed solubility in tetrahydrafuran (THF) were subjected to analysis using gel-permeation chromatography (GPC) to probe polymer molecular weight and dispersity (Table 2). Experimental molecular weights did not correlate exactly to the predicted by monomer-to-initiator ratios ($M_{n,theo}$=[M]/[I]), while dispersity (Đ) values from 1.1 to 1.6 suggested that polymerization proceeded with only moderate control. As discussed previously, reaction monitoring suggested that rates of propagation were fast relative to initiation, resulting in larger than expected molecular weight and increased polymer dispersity. Notably, not all isolated polymers possessed solubility in THF for GPC analysis; for example, P4, with its hydrogen bonding methoxy substituent, could be characterized in chloroform by NMR spectroscopy but was not completely soluble in THF or chloroform. This observation may indicate that the formation of extensive hydrogen-bonding networks may result in lower solubility of the polymer, due to increased inter- and intra-molecular forces. P2 also showed this lack of solubility, presumably due to the strong H-bond accepting potential of the fluorine substituent.

TABLE 2

Experimental and theoretical molecular weight ($M_n$).

| Entry | Polymer | [Ru]/ mol % | Theo. $M_n$/ g · mol$^{-1}$ | Exp. $M_n{}^a$/ g · mol$^{-1}$ | Đ$^a$ |
|---|---|---|---|---|---|
| 2 | P1 | 0.5 | 43,000 | 82,970 | 1.32 |
| 3 | P1 | 1 | 21,500 | 18,100 | 1.40 |
| 5 | P2 | 1 | 23,400 | — | — |
| 6 | P3 | 1 | 29,600 | 35,080 | 1.65 |
| 7 | P4 | 1 | 24,700 | — | — |

$^a$Determined by Gel-permeation chromatography (GPC)

4.5 Thermal Stability

Thermal stabilities (weight losses) of the polymers were determined by employing dynamic TGA experiments. Each sample was pre-heated at 105° C. for 5 min then heated from 30° C. to 600° C. at a heating rate of 10° C./min under nitrogen and oxygen.

Figure 4A:
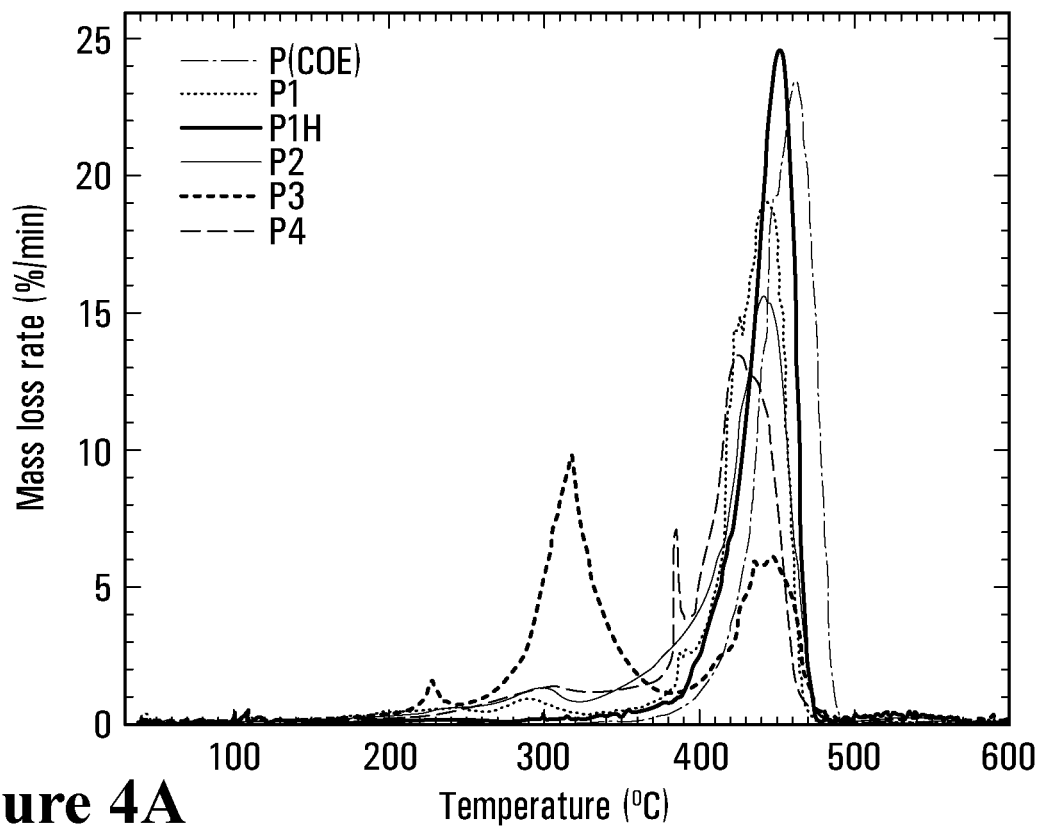
FIG. 4a is a graph of mass loss rate (%/min) as a function of temperature for five polymers of the present disclosure, i.e. "P1", "P2", "P3", "P4", and "P1H".
Figure 4B:
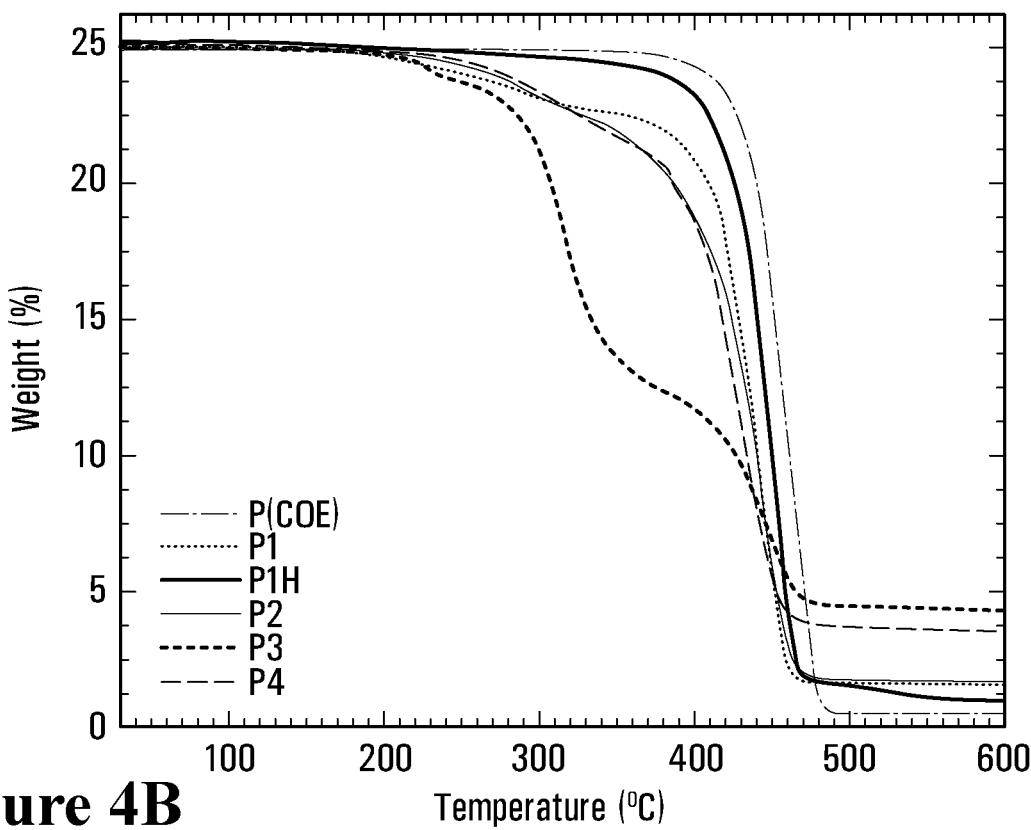
FIG. 4b is a graph of weight loss (%) as a function of temperature for five polymers of the present disclosure.

An average of three independent measurements was made. There was no difference in TGA curves for samples tested under nitrogen or oxygen atmosphere, indicating good thermo-oxidative stability. FIGS. 4a and 4b show selected weight loss curves and Table 4 summarizes 5% weight loss temperatures for tested polymers. Results demonstrate that P(Cyclooctene) is a thermally stable polymer with only one weight loss step at 415° C., which was assigned to the degradation of the polymer chain. Functionalized P1 shows a two-step weight loss. An initial weight loss at around 300° C. was assigned to the loss of the N-methyl aniline side group. The second thermal degradation around 420° C. refers to the degradation of the main polymer chain. In general, polymers follow free radical degradation mechanisms which are initiated by bond dissociation at the temperature of pyrolysis. By observing the polymer structure and bond strengths, a probable initial degradation mechanism for the poly(pendantamine) (PPA) polymers may be via side-group elimination.

Figure 5:
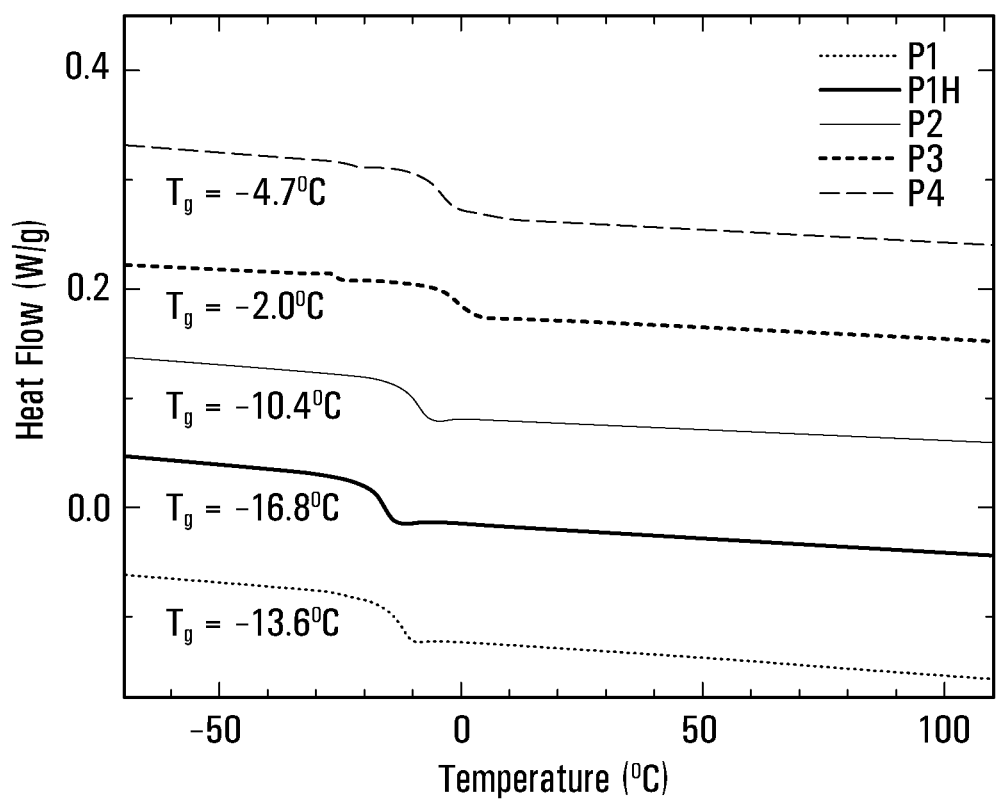
FIG. 5 are DSC thermograms of five polymers of the present disclosure.
Figure 6A:
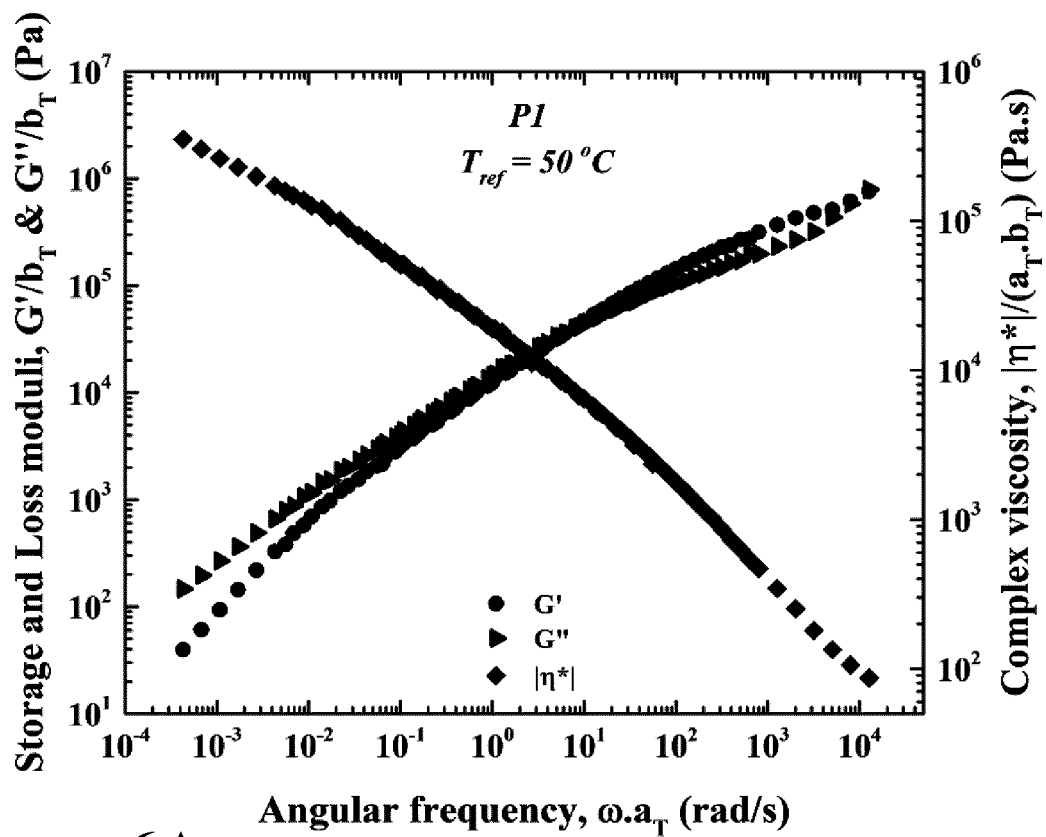
FIG. 6 shows master curves of the storage (G') and loss (G") moduli and complex viscosity (|η*|) (symbols) of (a) P1 at 50° C.; (b) P2 at 30°; (c) P3 at 50° C.; (d) P4 at 50° C.; (e) P1H at 50° C.
Figure 6B:
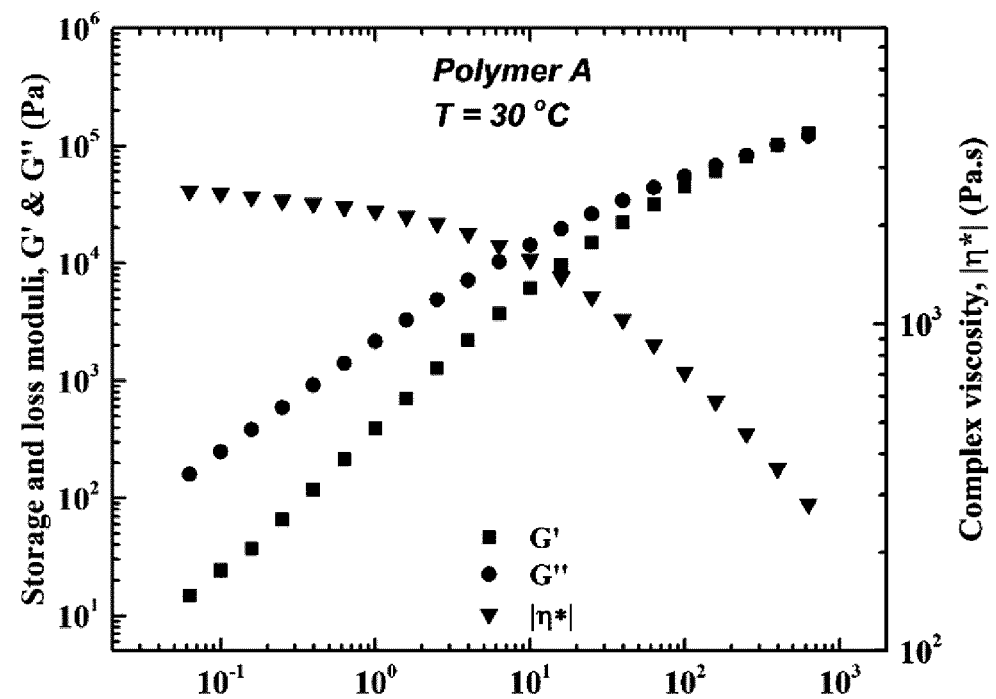
Figure 6C:
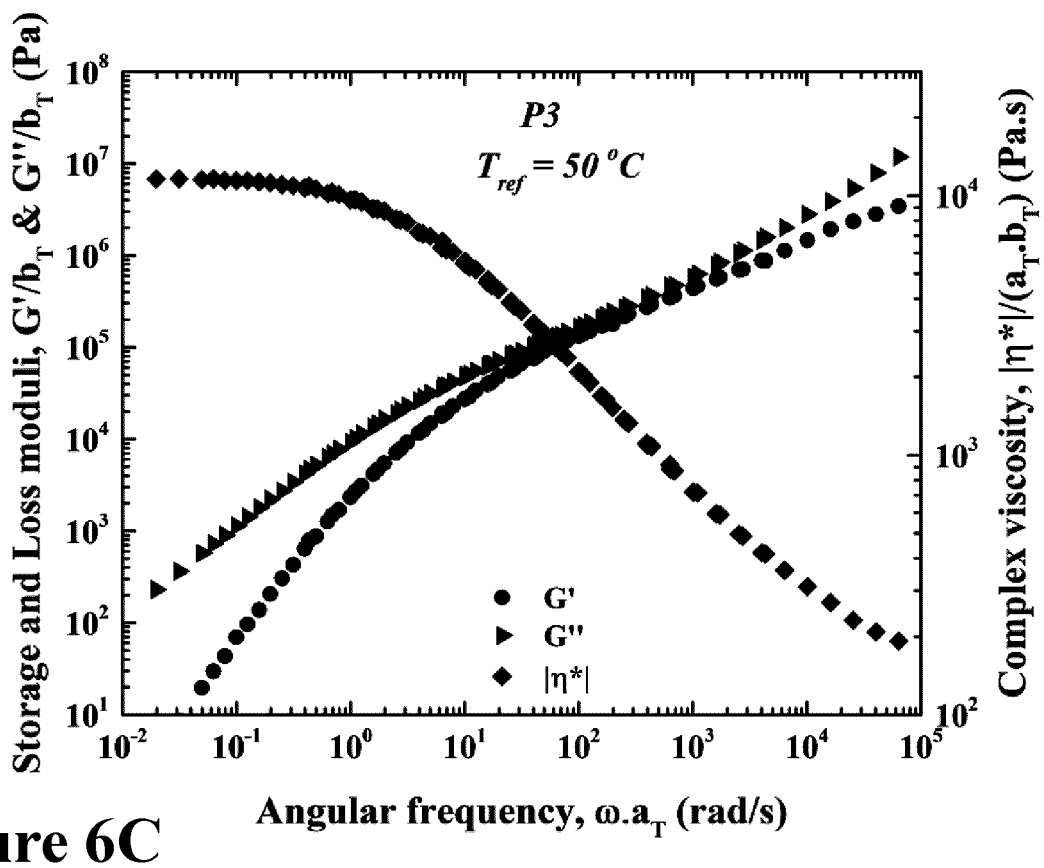
Figure 6D:
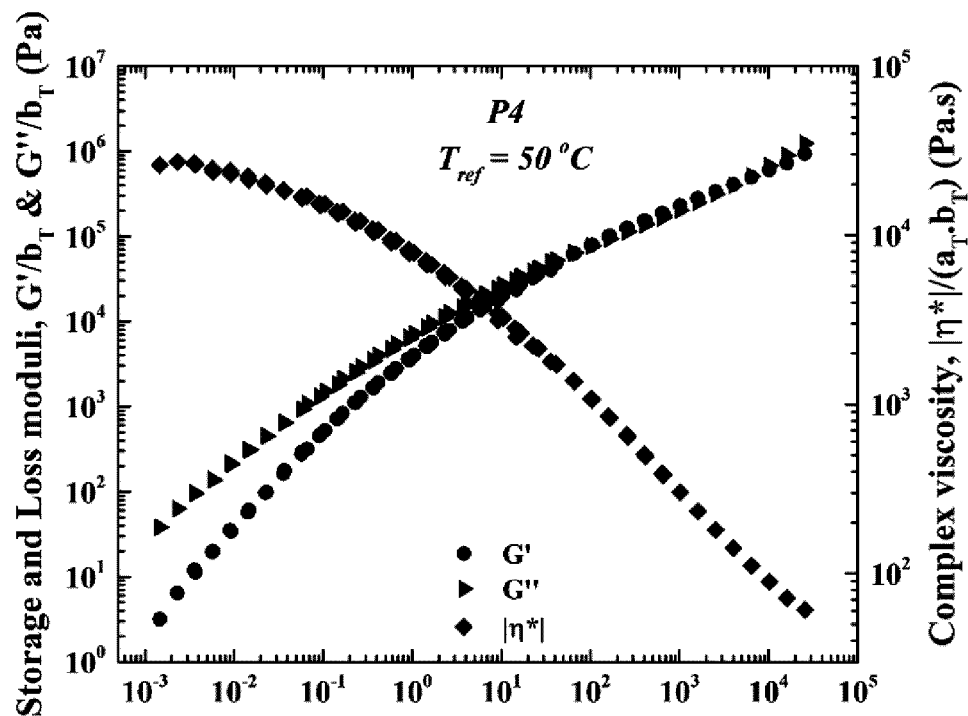
Figure 6E:
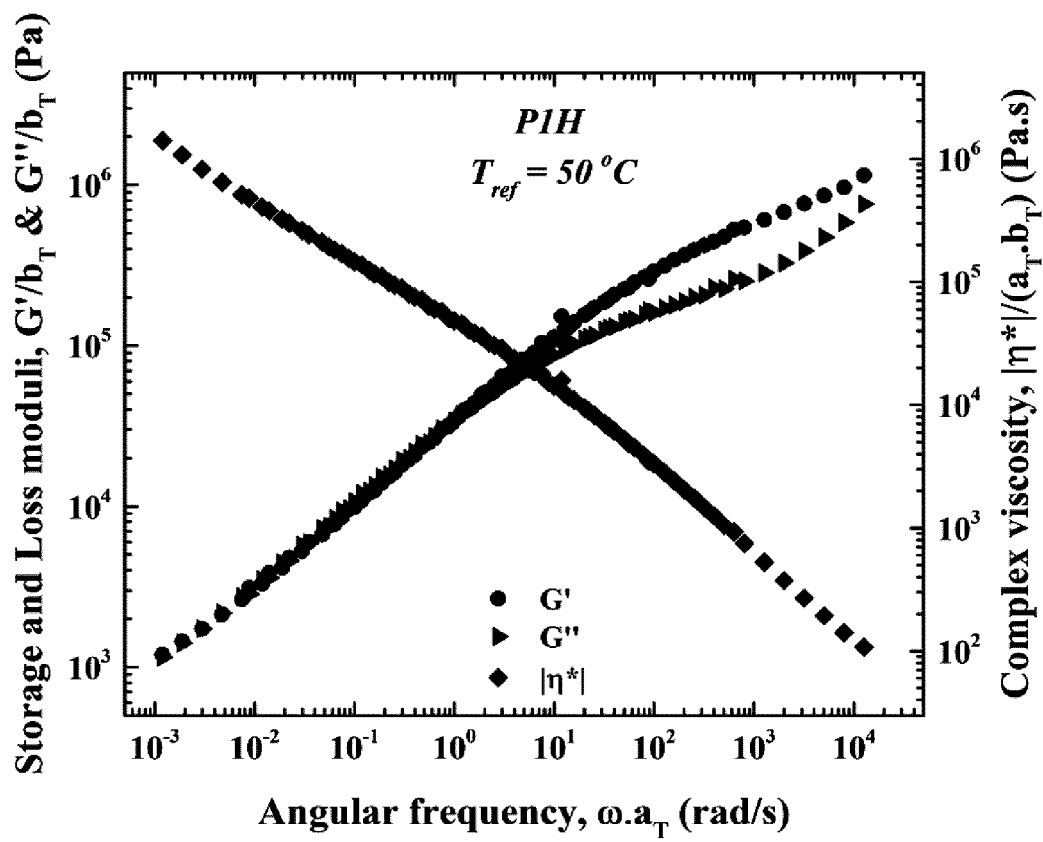

The derivative TGA, or DTG curves were useful for determination of the overlapping mass loss events, identification of minor mass loss steps, and finding the maxima of weight loss processes, wherein every peak in the TG curves may be an isolated event that may indicate the maximum rate of mass loss. Referring to FIG. 5, the thermograms obtained from differential scanning calorimetry (DSC) show behavior typical of amorphous polymers. The glass transition temperatures were attributed to chain transformation from glassy to rubbery regions and their values are summarized in Table 4 for each polymer.

TABLE 4

Thermal characterization by differential scanning calorimetry and thermogravimetric analysis.

| Polymers | $T_g$ (° C.) | $T_{5\%}$ (° C.) |
|---|---|---|
| P(cyclooctene) | — | 415 |
| P1 | −13.7 | 275 |
| P2 | −10.4 | 280 |
| P3 | −2.0 | 255 |
| P4 | −4.7 | 287 |
| P1H | −16.8 | 400 |

4.6 Rheology

Representative master curves of shifted storage and loss moduli and complex viscosity of various amine derivatives of poly(cyclooctene) as a function of shifted angular frequency are depicted in FIG. 6a to 6e. A plethora of distinctively different rheological behaviors was obtained, which may be attributed to the various hydrogen bonding environments promoted by the different aryl amines. Information obtained for P1, P1H pre-hydrogenation, P1H, and P3 is eported in Tables 5A to 5D below. P1 showed liquid-like behavior (G">G'), whereas, P3, and P4 exhibited the transition from liquid-like to solid-like behavior through gel-like behavior. P2 exhibited soft solid-like behavior (G'≥G"), which became more evident by introducing the polar F functional group that may also engage in hydrogen bonding interactions. Furthermore, the presence of strong F—H bonds may be responsible for formation of 3D network resulting in a material that behaves as viscoelastic solid with a higher melting temperature than the reference material. In comparing storage moduli for P1 and P2, the transition from liquid-like to solid-like behavior is evident. Strong physical crosslinking of P2 was observed during the fabrication/formation of film using solution casting. This may be explained by the alignment of polymer chains in solution allowing for easier formation of hydrogen bonds. P3 and P4 exhibited clear zero-shear viscosities which were higher than for P3. Bromine functionalized poly(cyclooctene) may form stronger hydrogen bonded structure due to possibly higher molecular weight.

TABLE 5A

Rheological behaviors of polymer P1.

Configuration Notes:
    Concentration Source: RI
    Flow Rate: 0.500 mL/min
    Light Scattering Instrument: miniDAWN TREOS
    Cell Type: Fused Silica
    Wavelength: 659.4 nm
    Calibration Constant: 4.8798 × 10⁻⁵ 1/(V cm)
    RI Instrument: Optilab rEX
    Viscometer: ViscoStar
    Dilution Factor: 0.4972
    Solvent: thf
    Temperature Correction Enabled: no
    Refractive Index: 1.402

TABLE 5A-continued

Rheological behaviors of polymer P1.

Processing   Collection Time: Tuesday Jun. 20, 2017 12:35:00 PM
    Pacific Daylight Time
    Processing Time: Wednesday Jun. 21, 2017 11:02:17 AM
    Pacific Daylight Time
    Peak settings:
    Peak Name Peak 1
    Peak Limits (min) 10.360-18.692
    Light Scattering Model Zimm
    Fit Degree 1
    dn/dc (mL/g) 0.1068
    A2 (mol mL/g$^2$) 0.000
    UV Ext. Coef. (mL/(mg cm)) 0.000
    Viscometry Model Huggins
    Huggins Equation Parameter 0
    Kraemers Equation Parameter 0
    Molar Mass & Radius from LS:
    Enabled Detectors: 1 2 3
    Results Fitting Procedure:

| Data | Fit Model | Degree | $R^2$ | Extrapolation |
|---|---|---|---|---|
| Molar Mass | None | n/a | n/a | none |
| Rms Radius | None | n/a | n/a | none |
| Mean Square Radius | None | n/a | n/a | none |
| Hydrodynamic Radius (Q) | None | n/a | n/a | none |

Results
    Peak Results

Peak 1
Hydrodynamic radius (v) moments (nm)

| Rh(v)n | 2.604 (±2.059%) |
|---|---|
| Rh(v)w | 3.097 (±1.947%) |
| Rh(v)z | 3.709 (±2.067%) |

Masses

| Calculated Mass (μg) | 243.98 |
|---|---|
| Mass Recovery (%) | 100.0 |
| Mass Fraction (%) | 100.0 |

Molar mass moments (g/mol)

| Mn | 1.810 × 10$^4$ (±4.998%) |
|---|---|
| Mp | 2.505 × 10$^4$ (±4.301%) |
| Mv | 2.355 × 10$^4$ (±0.234%) |
| Mw | 2.527 × 10$^4$ (±4.388%) |
| Mz | 3.526 × 10$^4$ (±9.764%) |

Polydispersity

| Mw/Mn | 1.397 (±6.651%) |
|---|---|
| Mz/Mn | 1.949 (±10.969%) | rms radius moments (nm)

| Rn | 2.7 (±2275.8%) |
|---|---|
| Rw | 7.6 (±273.0%) |
| Rz | 10.1 (±148.5%) |

Intrinsic viscosity moments (mL/g)

| [η]n | 6.663 (±3.679%) |
|---|---|
| [η]w | 8.11 (±3.49%) |
| [η]z | 9.881 (±4.059%) |
| Mark-Houwink-Sakurada | a: 0.595 (±0.459%) |
| Mark-Houwink-Sakurada | K: 2.041 × 10$^{-2}$ (±2.803%) mL/g |

TABLE 5B

Rheological behaviors of polymer P1H prior to hydrogentation.

Configuration Notes:
    Concentration Source: RI
    Flow Rate: 0.500 mL/min
    Light Scattering Instrument: miniDAWN TREOS
    Cell Type: Fused Silica TABLE 5B-continued Rheological behaviors of polymer P1H prior to hydrogenation.

| | | | | |
|---|---|---|---|---|
| Processing | Wavelength: 659.4 nm<br>Calibration Constant: 4.8798 × 10$^{-5}$ 1/(V cm)<br>RI Instrument: Optilab rEX<br>Viscometer: ViscoStar<br>Dilution Factor: 0.4972<br>Solvent: thf<br>Temperature Correction Enabled: no<br>Refractive Index: 1.402<br>Collection Time: Thursday Jul. 27, 2017 09:21:33 AM<br>Pacific Daylight Time<br>Processing Time: Thursday Aug. 10, 2017 11:29:41 AM<br>Pacific Daylight Time<br>Peak settings:<br>Peak Name Peak 1<br>Peak Limits (min) 10.273-15.431<br>Light Scattering Model Zimm<br>Fit Degree 1<br>dn/dc (mL/g) 0.1217<br>A2 (mol mL/g$^2$) 0.000<br>UV Ext. Coef. (mL/(mg cm)) 0.000<br>Viscometry Model Huggins<br>Huggins Equation Parameter 0<br>Kraemers Equation Parameter 0<br>Molar Mass & Radius from LS:<br>Enabled Detectors: 1 2 3<br>Results Fitting Procedure: | | | |

| Data | Fit Model | Degree | $R^2$ | Extrapolation |
|---|---|---|---|---|
| Molar Mass | None | n/a | n/a | none |
| Rms Radius | None | n/a | n/a | none |
| Mean Square Radius | None | n/a | n/a | none |
| Hydrodynamic Radius (Q) | None | n/a | n/a | none |

| | | |
|---|---|---|
| Results | Pe Peak Results | |
| | Peak 1 | |
| | Hydrodynamic radius (v) moments (nm) | |
| Rh(v)n | 6.465 (±0.962%) | |
| Rh(v)w | 7.437 (±0.918%) | |
| Rh(v)z | 9.278 (±1.010%) | |
| | Masses | |
| Calculated Mass (μg) | 147.97 | |
| Mass Recovery (%) | 100.0 | |
| Mass Fraction (%) | 100.0 | |
| | Molar mass moments (g/mol) | |
| Mn | 7.357 × 10$^4$ (±2.562%) | |
| Mp | 9.930 × 10$^4$ (±2.425%) | |
| Mv | 9.110 × 10$^4$ (±0.177/0) | |
| Mw | 9.831 × 10$^4$ (±2.461%) | |
| Mz | 1.587 × 10$^5$ (±5.461%) | |
| | Polydispersity | |
| Mw/Mn | 1.336 (±3.553%) | |
| Mz/Mn | 2.156 (±6.032%) | |
| | rms radius moments (nm) | |
| Rn | 21.4 (±21.5%) | |
| Rw | 21.7 (±20.7%) | |
| Rz | 22.3 (±19.2%) | |
| | Intrinsic viscosity moments (mL/g) | |
| [η]n | 24.537 (±1.116%) | |
| [η]w | 28.97 (±0.94%) | |
| [η]z | 37.624 (±1.610%) | |
| Mark-Houwink-Sakurada a: | 0.587 (±0.163%) | |
| Mark-Houwink-Sakurada K: | 3.619 × 10$^{-2}$ (±1.111%) mL/g | |

TABLE 5C

Rheological behaviors of polymer P1H.

| | |
|---|---|
| Configuration | Notes:<br>Concentration Source: RI<br>Flow Rate: 0.500 mL/min<br>Light Scattering Instrument: miniDAWN TREOS<br>Cell Type: Fused Silica<br>Wavelength: 659.4 nm<br>Calibration Constant: 4.8798 × 10$^{-5}$ 1/(V cm)<br>RI Instrument: Optilab rEX<br>Viscometer: ViscoStar<br>Dilution Factor: 0.4972<br>Solvent: thf<br>Temperature Correction Enabled: no<br>Refractive Index: 1.402 |
| Processing | Collection Time: Wednesday Aug. 16, 2017 01:48:03 PM<br>Pacific Daylight Time<br>Processing Time: Thursday Aug. 17, 2017 12:32:27 PM<br>Pacific Daylight Time<br>Peak settings:<br>Peak Name Peak 1<br>Peak Limits (min) 9.078-17.166<br>Light Scattering Model Zimm<br>Fit Degree 1<br>dn/dc (mL/g) 0.1182<br>A2 (mol mL/g$^2$) 0.000<br>UV Ext. Coef. (mL/(mg cm)) 0.000<br>Viscometry Model Huggins<br>Huggins Equation Parameter 0<br>Kraemers Equation Parameter 0<br>Molar Mass & Radius from LS:<br>Enabled Detectors: 1 2 3<br>Results Fitting Procedure: |

| Data | Fit Model | Degree | $R^2$ | Extrapolation |
|---|---|---|---|---|
| Molar Mass | None | n/a | n/a | none |
| Rms Radius | None | n/a | n/a | none |
| Mean Square Radius | None | n/a | n/a | none |
| Hydrodynamic Radius (Q) | None | n/a | n/a | none |

| | | |
|---|---|---|
| Results | Peak Results | |
| | Peak 1 | |
| | Hydrodynamic radius (v) moments (nm) | |
| Rh(v)n | 6.165 (±1.466%) | |
| Rh(v)w | 6.804 (±1.444%) | |
| Rh(v)z | 7.984 (±1.516%) | |
| | Masses | |
| Calculated Mass (μg) | 159.99 | |
| Mass Recovery (%) | 100.0 | |
| Mass Fraction (%) | 100.0 | |
| | Molar mass moments (g/mol) | |
| Mn | 7.123 × 10$^4$ (±3.741%) | |
| Mp | 8.224 × 10$^4$ (±3.418%) | |
| Mv | 8.257 × 10$^4$ (±0.218%) | |
| Mw | 8.710 × 10$^4$ (±3.581%) | |
| Mz | 1.201 × 10$^5$ (±8.008%) | |
| | Polydispersity | |
| Mw/Mn | 1.223 (±5.179%) | |
| Mz/Mn | 1.686 (±8.839%) | |
| | rms radius moments (nm) | |
| Rn | 23.5 (±23.9%) | |
| Rw | 23.2 (±23.9%) | |
| Rz | 23.1 (±23.6%) | |
| | Intrinsic viscosity moments (mL/g) | |
| [η]n | 21.831 (±1.685%) | |
| [η]w | 24.71 (±1.68%) | |
| [η]z | 29.566 (±2.407%) | |
| Mark-Houwink-Sakurada a: | 0.601 (±0.222%) | |
| Mark-Houwink-Sakurada K: | 2.989 × 10$^{-2}$ (±1.536%) mL/g | |

TABLE 5D

Rheological behaviors of polymer P3.

| | | | | | |
|---|---|---|---|---|---|
| Configuration | Notes: | | | | |
| | Concentration Source: RI | | | | |
| | Flow Rate: 0.500 mL/min | | | | |
| | Light Scattering Instrument: miniDAWN TREOS | | | | |
| | Cell Type: Fused Silica | | | | |
| | Wavelength: 659.4 nm | | | | |
| | Calibration Constant: $4.8798 \times 10^{-5}$ 1/(V cm) | | | | |
| | RI Instrument: Optilab rEX | | | | |
| | Viscometer: ViscoStar | | | | |
| | Dilution Factor: 0.4972 | | | | |
| | Solvent: thf | | | | |
| | Temperature Correction Enabled: no | | | | |
| | Refractive Index: 1.402 | | | | |
| Processing | Collection Time: Thursday Jul. 27, 2017 12:04:40 PM Pacific Daylight Time | | | | |
| | Processing Time: Thursday Aug. 10, 2017 11:22:31 AM Pacific Daylight Time | | | | |
| | Peak settings: | | | | |
| | Peak Name Peak 1 | | | | |
| | Peak Limits (min) 8.699-17.441 | | | | |
| | Light Scattering Model Zimm | | | | |
| | Fit Degree 1 | | | | |
| | dn/dc (mL/g) 0.1179 | | | | |
| | A2 (mol mL/g$^2$) 0.000 | | | | |
| | UV Ext. Coef. (mL/(mg cm)) 0.000 | | | | |
| | Viscometry Model Huggins | | | | |
| | Huggins Equation Parameter 0 | | | | |
| | Kraemers Equation Parameter 0 | | | | |
| | Molar Mass & Radius from LS: | | | | |
| | Enabled Detectors: 1 2 3 | | | | |
| | Results Fitting Procedure: | | | | |

| | Data | Fit Model | Degree | $R^2$ | Extrapolation |
|---|---|---|---|---|---|
| | Molar Mass | None | n/a | n/a | none |
| | Rms Radius | None | n/a | n/a | none |
| | Mean Square Radius | None | n/a | n/a | none |
| | Hydrodynamic Radius (Q) | None | n/a | n/a | none |
| Results | Pe Peak Results | | | | |

Peak 1
Hydrodynamic radius (v) moments (nm)

| | |
|---|---|
| Rh(v)n | 3.615 (±2.518%) |
| Rh(v)w | 4.737 (±1.844%) |
| Rh(v)z | 6.387 (±1.847%) |

Masses

| | |
|---|---|
| Calculated Mass (µg) | 133.00 |
| Mass Recovery (%) | 100.0 |
| Mass Fraction (%) | 100.0 |

Molar mass moments (g/mol)

| | |
|---|---|
| Mn | $3.508 \times 10^4$ (±2.050%) |
| Mp | $5.788 \times 10^4$ (±2.766%) |
| Mv | $5.136 \times 10^4$ (±0.167/0) |
| Mw | $5.802 \times 10^4$ (±2.577%) |
| Mz | $1.007 \times 10^5$ (±6.010%) |

Polydispersity

| | |
|---|---|
| Mw/Mn | 1.654 (±3.293%) |
| Mz/Mn | 2.870 (±6.350%) | rms radius moments (nm)

| | |
|---|---|
| Rn | n/a |
| Rw | 10.5 (±71.9%) |
| Rz | 15.7 (±35.9%) |

Intrinsic viscosity moments (mL/g)

| | |
|---|---|
| [η]n | 9.733 (±5.087%) |
| [η]w | 13.61 (±3.65%) |
| [η]z | 18.507 (±4.394%) |
| Mark-Houwink-Sakurada a: | 0.580 (±0.380%) |
| Mark-Houwink-Sakurada K: | $2.753 \times 10^{-2}$ (±2.463%) mL/g |

4.7 Self-Healing Properties

Figure 17:
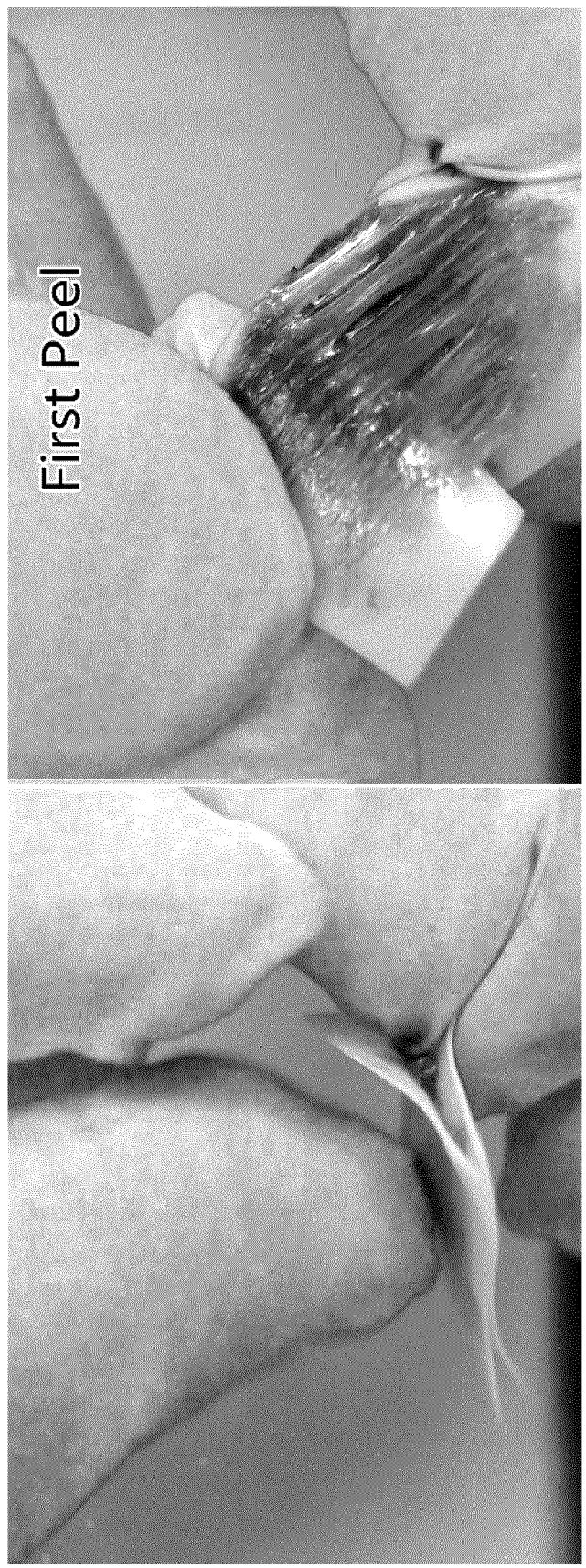
FIG. 17 is a photographic image depicting the adhesive properties of the polymer.

Referring to FIG. 17, polymers as disclosed herein exhibit self-healing properties. The self-healing properties of these polymers appears to be related to their ability to possess chain mobility as amorphous materials.

4.8 Copolymers

4.8.1 Copolymers with Cyclooctene

In an attempt to explore the extent to which the advantageous properties of these novel polymers could be retained with lower incorporations of amine in the polymer, the amine incorporation in the final polymer was reduced by adding excess equivalents of cyclooctene to the ROMP reaction. The ultimate goal is to maintain the desirable properties imparted by the amine functional group while lowering its incorporation in less expensive, less functionalized polyolefins.

Synthesis of polymer with reduced amine incorporation was conducted according to the following scheme.

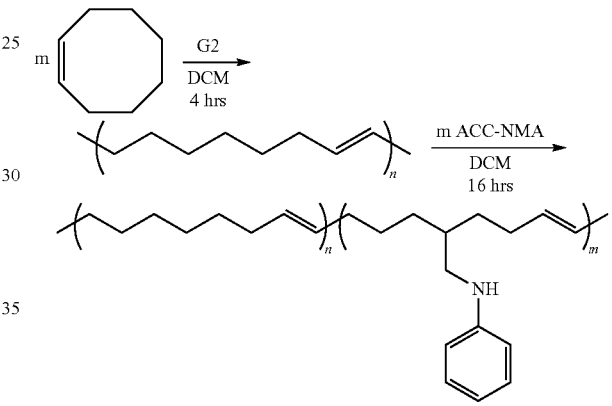

P(P1-co-cyclooctene) General preparation for a 1:1 by mol copolymer was prepared as follows: To a 20 mL scintillation vial was added the first monomer, eg. cyclooctene (51 mg, 0.4 mmol) and a solution of G2 (3.7 mg, 0.004 mmol) in THF (1 mL) with a stir bar. After reacting the first monomer at room temperature for the time required (eg. 4 hrs for cyclooctene), the second monomer, eg. M1 (100 mg, 0.4 mmol. 1:1 mol ratio with cyclooctene). After time required to react second monomer, the entire reaction was quenched and polymer isolated using standard practice with addition of ethyl vinyl ether and precipitation into methanol. $^1$H NMR (300 MHz, CDCl$_3$): δ 7.19 (m, 2H, 2×ArH), δ 6.71 (br s, 3H, 3×ArH), δ 5.40 (m, 4H, RHC=CHR), δ 3.03 (d, 2H, CH$_2$), δ 2.00 (m, 8H, CH$_2$), δ 1.68 (br s, 1H, CH), δ 1.49-1.26 (m, 14H, CH$_2$). The results of the synthesis are further reported in Table 6 below.

TABLE 6

| First monomer | Second monomer | Characterization |
|---|---|---|
| cyclooctene | M1 | $M_{n, calc}$ = 19,019; Đ = 1.48*. $^1$H NMR: 59/41 M1:M2 |
| cyclooctene | M1 | $M_{n, calc}$ = 36,951; Đ = 1.07*. $^1$H NMR: 57/43 M1:M2 |

$M_{n, calc}$ determined using molecular weight of quenched aliquot of P1 then relating MW of P2 by using integrations in $^1$H NMR spectrum.

4.8.2 Copolymers with Arylamine Substituted Norbornene Monomer Units

In contrast to the polymers disclosed and prepared herein, polymers formed from arylamine substituted norbornene monomers do not show self-healing behaviour. It was of interest to combine these monomers to explore whether this behavior could be tuned and allow for the preparation of materials with variable physical properties Co-polymers of the amine-functionalized cycloalkene monomers disclosed above and several arylamine substituted norbornene monomers including:

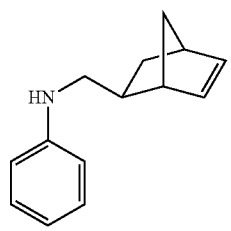

("ACN-1")

and

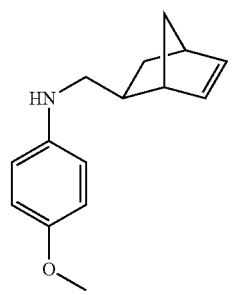

("ACN-4")

Monomers ACN-1 and ACN-4 can be prepared as disclosed by Perry et al. (Macromolecules, 49: 4423 to 4430).

A simultaneous addition of monomers was employed in the attempted formation of copolymers

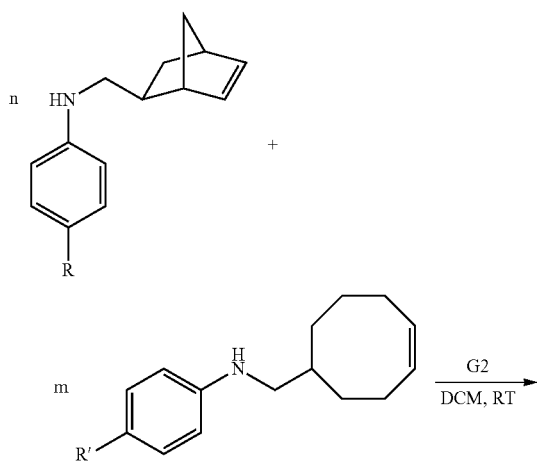

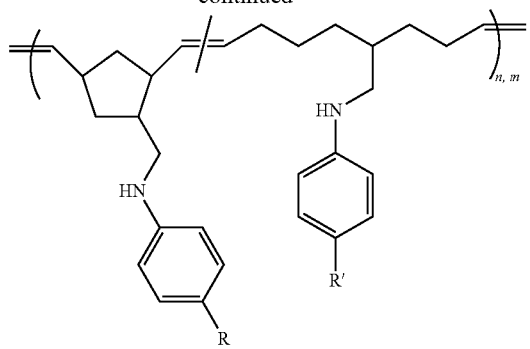

R/R' = H, F, Br, OMe

A series of different combinations of monomers with varying para R/R' substituents were co-polymerized via ROMP (50 equivalents of each monomer). Copolymers were prepared as in homopolymers using various stoichiometric amounts of the different monomers to give theoretical ratio in polymer product. A typical procedure is as follows:

P(ACN-1-co-P2)

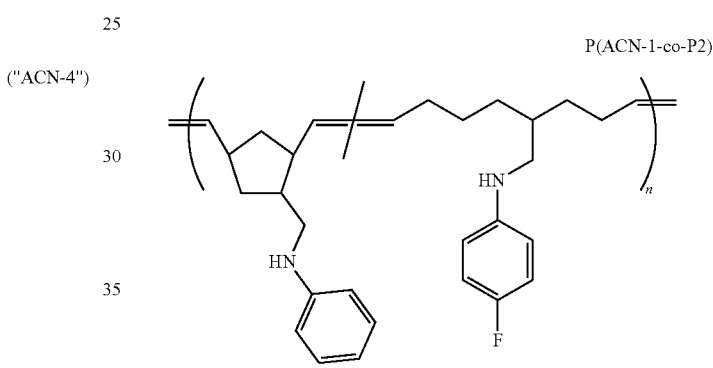

To a 20 mL scintillation vial was added ACN-1 (50 mg, 0.25 mmol) and polymer P2 (58 mg, 0.25 mmol) with ca. 1 mL $CH_2Cl_2$. To this solution was added a solution of Grubbs Catalyst™ 2nd Generation ("G2"; 4.2 mg, 0.005 mmol) in ca. 1 mL $CH_2Cl_2$. The reaction was stirred for 20 h at room temperature, during which the solution slowly goes brown-green from the initial amber color. The polymer was isolated using standard practice with addition of ethyl vinyl ether and precipitation into methanol; yields are quantitative with losses due to collection from precipitation. $^1$H NMR (300 MHz, $CDCl_3$): δ 7.16 (s, 2H, 2×ArH), δ 6.87 (m, 2H, 2×ArH), δ 6.75 (m, 3H, 3 ArH), δ 6.55 (br s, 2H, 2×ArH), δ 5.39-5.27 (m, 4H, 2×RHC=CHR), δ 3.05-2.97 (d, 4H, $CH_2$), δ 2.90 (s, 1H, CH), δ 2.53 (s, 1H, CH), δ 2.00-1.95 (m, 6H, $CH_2$), δ 1.65-1.63 (br s, 3H), δ 1.36 (br s, 6H, $CH_2$), δ 1.19 (s, 1H, CH).

Isolation of quenched reaction solutions by precipitation gave a material with physical properties that are intermediate to the respective homopolymers. Where homopolymers made from arylamine substituted norbornene monomers are stiff threads, and homopolymers as disclosed herein are sticky and tough gums, the copolymers aggregate and are tacky as in the latter, however with more pronounced stiffness. By $^1$H NMR spectroscopy, it was found that the resultant polymers had higher incorporations of the given ACN (52-74%). ACN-1 (R=H) and ACC-2 (R'=F) was chosen as a model system as both monomers were evenly incorporated (52:48 ACN:ACC). To ensure that a copolymer was formed, rather than two homopolymers, GPC analysis was performed on this sample; one peak was observed with reasonable agreement to the theoretical value ($M_{n,\ exp}$=18, 130 g·mol$^{-1}$,Đ=1.61, $M_{n,\ theo.}$=21,630 g·mol$^{-1}$).

Figure 18:
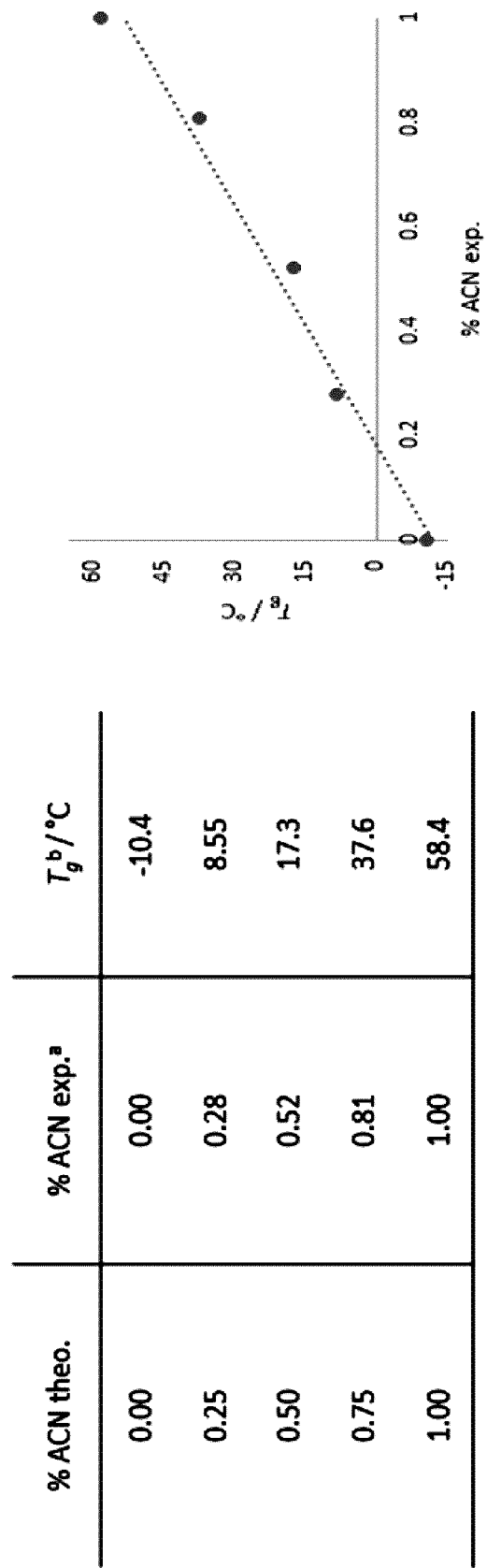
FIG. 18 is a graph showing the effect of the ratio of CAN-1 and P2 monomer ratio in copolymer on observed glass transition temperature.

To explore whether the thermal properties can be tuned based on the relative incorporation of monomers, three different ratios of the polymer P(ACN-1-co-P2) model system were prepared. The experimental ratios determined by $^1$H NMR spectroscopy are indicated in Table 7. The glass transition temperatures as determined by DSC are shown in Table 7 and FIG. 18. As indicated in FIG. 18, the glass transition could be tuned by adjusting the feed ratio of both monomers. The observation of a single glass transition in each sample is also indicative of copolymer synthesis in which both blocks possess miscibility.

TABLE 7

Ratios of monomer in co-polymer.

| % ACN theo. | % ACN exp.$^a$ | $T_g^{\ b}$/° C. |
|---|---|---|
| 0.00 | 0.00 | −10.4 |
| 0.25 | 0.28 | 8.55 |
| 0.50 | 0.52 | 17.3 |
| 0.75 | 0.81 | 37.6 |
| 1.00 | 1.00 | 58.4 |

$^a$Calculated by $^1$H NMR spectroscopy
$^b$Determined by DSC

Figure 19:
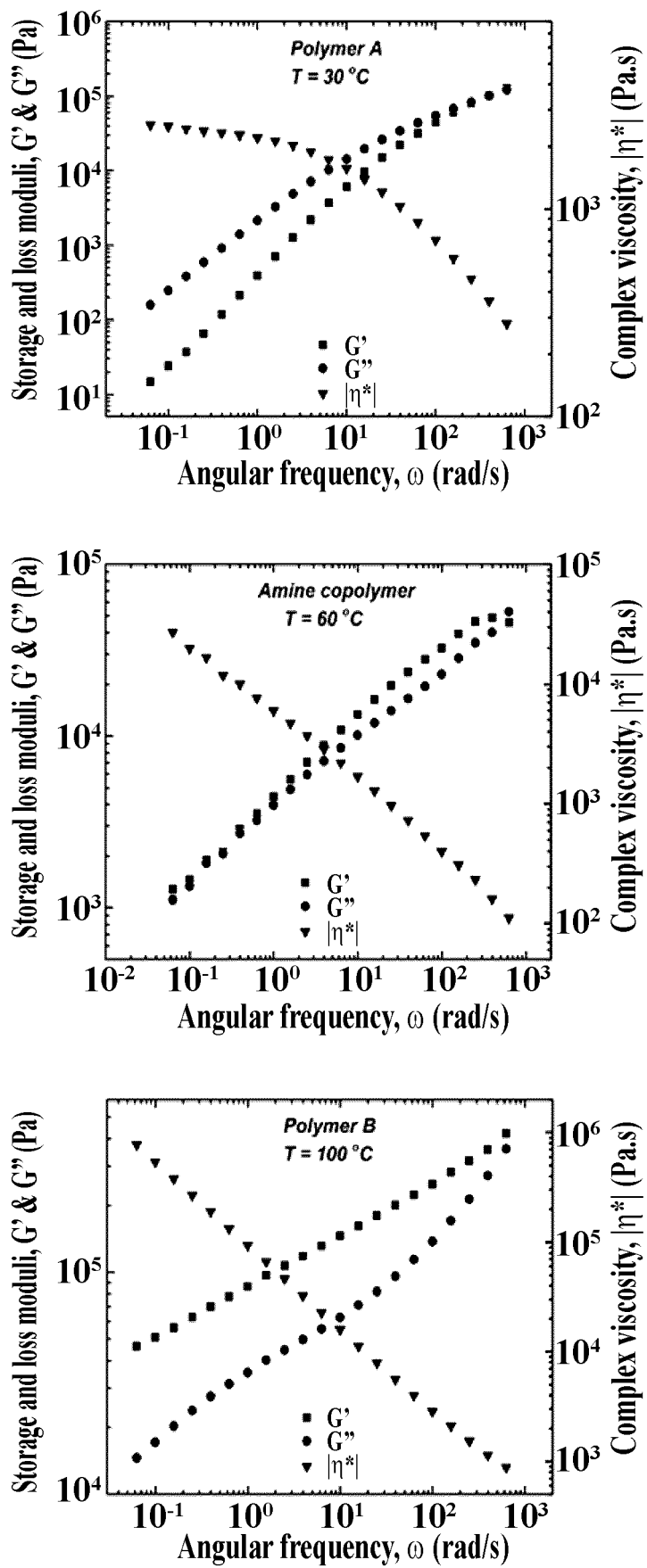
FIG. 19 shows master curves of the storage (G') and loss (G") moduli and complex viscosity (|η*|) (symbols) of polymer P2 at 50° C., co-polymer P(ACN-1-co-P2) at 50° C., and homopolymer of ACN-1 at 50° C.

The effects of these varied ratios on viscoelasticity was examined. Referring to FIG. 19, melt rheology was conducted on the model copolymer with equal incorporation of ACN-1 and M2 segments. The P(ACN-1-co-P2) copolymer demonstrates rheological characteristics that are intermediate to the two pure homopolymers. Polymer P2 shows that loss modulus is dominant over the entire frequency range, suggesting liquid-like behavior. Storage modulus predominates in P(ACN-1) as a soft-solid material. In the copolymer, storage and loss moduli are roughly equivalent at low frequency; at higher frequencies storage modulus is dominant, with a cross-over point at the terminal zone. This observed rheological behavior also suggests a copolymer with miscible domains.

Qualitative healing tests were performed to explore the effect of varying the glass transition temperature ($T_g$). It was hypothesized that all samples that had a glass transition below room temperature would demonstrate self-healing. Of the three copolymers, only the sample with 3:1 M2:ACN-1 ratio ($T_g$=8.6° C.) demonstrated healing within 24 hours. The sample with 1:1 M2:ACN-1 ($T_g$=17.3° C.) did not demonstrate healing at the ambient conditions. These results suggest that tuning the thermal behavior may allow tuning of healing time depending on the needs of the material.

While specific embodiments of the invention have been described and illustrated, such embodiments should be considered illustrative of the invention only and not as limiting the invention as construed in accordance with the accompanying claims. Many adaptations and modifications may be made within the scope of the invention in accordance with the common general knowledge of those skilled in this art. Such modifications include the substitution of known equivalents for any aspect of the invention in order to achieve the same result in substantially the same way.

What is claimed is:

1. An amine-functionalized compound of Formula 2:

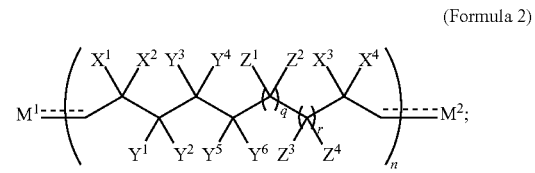

(Formula 2)

wherein ------- is a single bond or a double bond;
wherein each of $M^1$ and $M^2$ independently is —OH, a substituted or unsubstituted $C_{1-15}$ alkyl, a substituted or unsubstituted aromatic cycle, a substituted or unsubstituted heterocycle, or a functional end-group suitable for ring opening metathesis polymerization;
wherein each $X^1$, $X^2$, $X^3$, and $X^4$ is independently H or $CH_3$;
wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$ and the remainder of $Y^1$, $Y^2$, $Y^3$, $Y^4$, $Y^5$, $Y^6$, $Z^1$, $Z^2$, $Z^3$, and $Z^4$ are independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R'';
wherein each of R' and R'' is independently H, a substituted or unsubstituted linear or cyclic alkyl or alkenyl, a substituted or unsubstituted aryl, a substituted or unsubstituted heterocycle, or an amine-compatible protection group;
wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group provided that at least one of $R^3$ and $R^4$ is not H, or wherein $R^3$ and $R^4$ are linked to form a cyclic moiety, or wherein one of $R^3$ and $R^4$ is linked with one of $R^1$ and $R^2$ to form a cyclic moiety;
wherein r=0 or 1 and q=0 or 1, wherein r+q=0, 1, or 2; and
wherein n is a natural number greater than 2,
wherein the repeat units in the parenthesis in Formula 2 are connected in a head to head fashion, head to tail fashion, tail to tail fashion, or any combination thereof.

2. The amine-functionalized compound of claim 1, wherein each of $X^1$, $X^2$, $X^3$, and $X^4$ is H.

3. The amine-functionalized compound of claim 1, wherein each of $R^1$ and $R^2$ is H.

4. The amine-functionalized compound of claim 1, wherein one of $R^3$ and $R^4$ is H.

5. The amine-functionalized compound of claim 1, wherein the compound is a polyalkane of Formula 5:

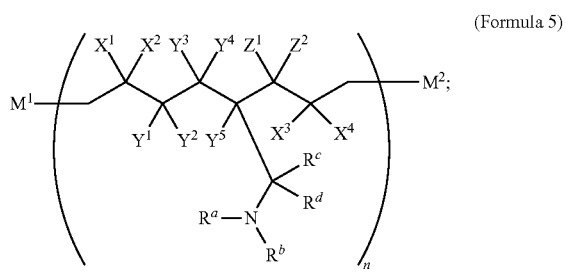

(Formula 5)

wherein each of $M^1$ and $M^2$ is independently —OH, a substituted or unsubstituted $C_{1-15}$ alkyl, a substituted or unsubstituted aromatic cycle, a substituted or unsubstituted heterocycle, or a functional end-group suitable for ring opening metathesis polymerization;

wherein each of $X^1$, $X^2$, $X^3$, and $X^4$ is independently H or $CH_3$;

wherein each of $Y^1$, $Y^2$, $Y^3$, $Y^4$, $Y^5$, $Z^1$, and $Z^2$ is independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R";

wherein each of R' and R" is independently H, a substituted or unsubstituted linear or cyclic alkyl or alkenyl, a substituted or unsubstituted aryl, a substituted or unsubstituted heterocycle, or an amine-compatible protection group;

wherein each of $R^a$, $R^b$, $R^c$, and $R^d$ is independently H, a substituted or unsubstituted linear or cyclic alkyl or alkenyl, a substituted or unsubstituted aryl, a substituted or unsubstituted heterocycle, or an amine-compatible protection group provided that at least one of $R^a$ and $R^b$ is not H, or wherein $R^b$ and $R^a$ are linked to form a cyclic moiety, or wherein one of $R^a$ and $R^b$ is linked with one of $R^c$ and $R^d$ to form a cyclic moiety;

wherein n is a natural number greater than 2; and wherein the repeat units in the parenthesis are connected in a head to head fashion, a head to tail fashion, a tail to tail fashion, or any combination thereof.

6. The polyalkane of claim 5, wherein each of $X^1$, $X^2$, $X^3$, and $X^4$ is H.

7. The polyalkane of claim 5, wherein each of $R^c$ and $R^d$ is H.

8. The polyalkane of claim 5, wherein one of $R^b$ and $R^a$ is H.

9. The amine-functionalized compound of claim 1, wherein  is a single bond.

10. A polymer comprising monomer units of the formulae:

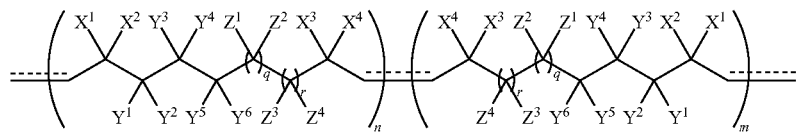

wherein  is a single bond or a double bond;

wherein each $X^1$, $X^2$, $X^3$, and $X^4$ is independently H or $CH_3$;

wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$ and the remainder of $Y^1$, $Y^2$, $Y^3$, $Y^4$, $Y^5$, $Y^6$, $Z^1$, $Z^2$, $Z^3$, and $Z^4$ are independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R";

wherein each of R' and R" is independently H, a substituted or unsubstituted linear or cyclic alkyl or alkenyl, a substituted or unsubstituted aryl, a substituted or unsubstituted heterocycle, or an amine-compatible protection group;

wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group provided that at least one of $R^3$ and $R^4$ is not H, or wherein $R^3$ and $R^4$ are linked to form a cyclic moiety, or wherein one of $R^3$ and $R^4$ is linked with one of $R^1$ and $R^2$ to form a cyclic moiety;

wherein in each monomer unit, r=0 or 1 and q=0 or 1, wherein in each monomer unit r+q=0, 1, or 2;

wherein n and m are natural numbers;

wherein n is greater than 2;

and wherein the repeat units in the parenthesis are connected in a head to head fashion, a head to tail fashion, a tail to tail fashion, or any combination thereof.

11. The polymer of claim 10, wherein each of $X^1$, $X^2$, $X^3$, and $X^4$ is H.

12. The polymer of claim 10, wherein each of $R^1$ and $R^2$ is H.

13. The polymer of claim 10, wherein one of $R^3$ and $R^4$ is H.

14. The polymer of claim 10 that is an amine functionalized polyalkene or polyalkane, wherein the polyalkene or polyalkane comprises:

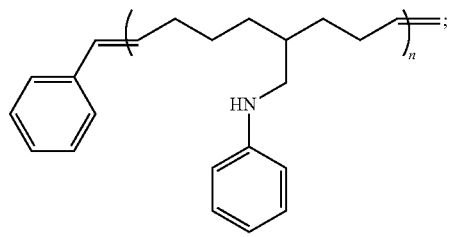

-continued

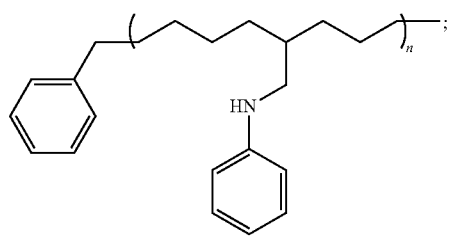

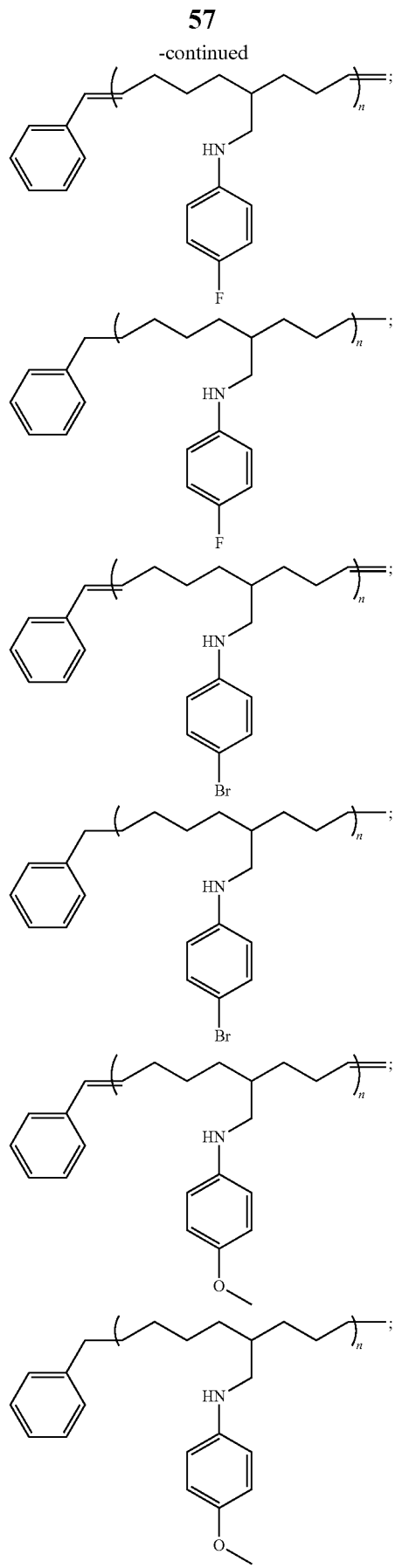

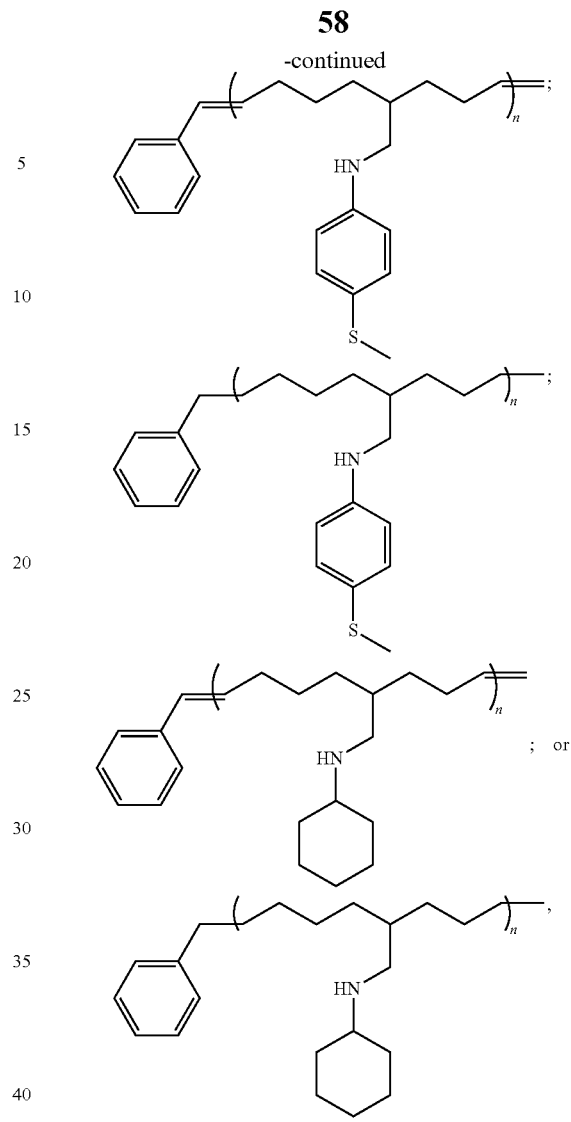

wherein n is a natural number greater than 2.

15. The polymer of claim 10, wherein ------- is a single bond.

16. A polymer comprising monomer units of the formulae:

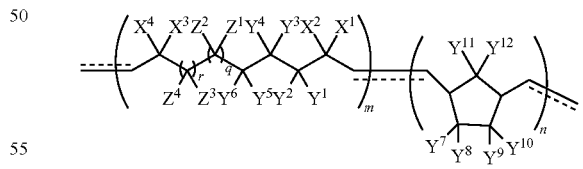

wherein ------- is a single bond or a double bond;
wherein each $X^1$, $X^2$, $X^3$, and $X^4$ is independently H or $CH_3$;
wherein at least one of $Y^1$, $Y^2$, $Y^3$, $Y^4$, $Y^5$, $Y^6$, $Z^1$, $Z^2$, $Z^3$, and $Z^4$ is —$CR^1R^2$—$NR^3R^4$ and the remainder of $Y^1$, $Y^2$, $Y^3$, $Y^4$, $Y^5$, $Y^6$, $Z^1$, $Z^2$, $Z^3$, and $Z^4$ are independently H, a substituted or unsubstituted linear or cyclic alkyl or alkenyl, a substituted or unsubstituted aryl, a substituted or unsubstituted heterocycle, an amine-compatible protection group, —C(=O)R', or —C(OR')R";

wherein each of R' and R" is independently H, a substituted or unsubstituted linear or cyclic alkyl or alkenyl, a substituted or unsubstituted aryl, a substituted or unsubstituted heterocycle, or an amine-compatible protection group;

wherein each of $R^1$, $R^2$, $R^3$ and $R^4$ is independently H, a substituted or unsubstituted linear or cyclic alkyl or alkenyl, a substituted or unsubstituted aryl, a substituted or unsubstituted heterocycle, or an amine-compatible protection group provided that at least one of $R^3$ and $R^4$ is not H, or wherein $R^3$ and $R^4$ are linked to form a cyclic moiety, or wherein one of $R^3$ and $R^4$ is linked with one of $R^1$ and $R^2$ to form a cyclic moiety;

wherein r=0 or 1 and q=0 or 1, wherein r+q=0, 1, or 2;

wherein n and m are natural numbers;

wherein n is greater than 2; and wherein the repeat units in the parenthesis are connected in a head to head fashion, a head to tail fashion, a tail to tail fashion, or any combination thereof.

17. The polymer of claim 16, wherein each of $X^1$, $X^2$, $X^3$, and $X^4$ is H.

18. The polymer of claim 16, wherein each of $R^1$ and $R^2$ is H.

19. The polymer of claim 16, wherein one of $R^3$ and $R^4$ is H.

20. The polymer of claim 16, wherein ------- is a single bond.

* * * * *